US005629172A

United States Patent [19]
Mascarenhas et al.

[11] Patent Number: 5,629,172
[45] Date of Patent: May 13, 1997

[54] EXPRESSION OF FUSION POLYPEPTIDES TRANSPORTED OUT OF THE CYTOPLASM WITHOUT LEADER SEQUENCES

[75] Inventors: Desmond Mascarenhas; Yang Zhang, both of Sunnyvale; Pamela S. Olson, Cupertino; David R. Olsen, Menlo Park; Pedro A. Cohen, San Francisco, all of Calif.

[73] Assignee: Celtrix Pharmaceuticals, Inc., Santa Clara, Calif.

[21] Appl. No.: 284,784

[22] Filed: Aug. 2, 1994

Related U.S. Application Data

[63] Continuation-in-part of Ser. No. 100,744, Aug. 2, 1993.

[51] Int. Cl.$^6$ ............................ C12N 1/19; C12N 15/62; C07K 14/00
[52] U.S. Cl. ................... 435/64.7; 435/69.1; 435/252.3; 435/320.1; 530/315; 536/23.4
[58] Field of Search ........................ 435/69.7, 252.3, 435/320.1; 530/350, 23.4

[56] References Cited

U.S. PATENT DOCUMENTS

| | | | |
|---|---|---|---|
| 4,595,658 | 6/1986 | Zinder et al. | 435/68 |
| 4,801,536 | 1/1989 | Stahl et al. | 435/60 |
| 5,084,384 | 1/1992 | Wong et al. | 435/64.4 |
| 5,143,830 | 9/1992 | Holland et al. | 435/69.7 |

FOREIGN PATENT DOCUMENTS

| | | |
|---|---|---|
| WO88/02406 | 4/1987 | WIPO . |
| WO89/09829 | 10/1989 | WIPO . |
| WO89/12678 | 12/1989 | WIPO . |
| WO91/11454 | 8/1991 | WIPO . |
| WO92/13955 | 8/1992 | WIPO . |

OTHER PUBLICATIONS

Williams, D.C. et al., "Cytoplasmic inclusion bodies in *Escherichia coli* producing biosynthetic human insulin proteins" *Science* (1992) 215:687–689.

Schoner, R.G. et al., "Isolation and purification of protein granules from *Escherichia coli* cells overproducing bovine growth hormone" *Bio/Technology* (Feb. 1985) pp. 151–154.

Goeddel, D.V. et al., "Expression in *Escherichia coli* of chemically synthesized genes for human insulin" *Proc. Natl. Acad. Sci. USA* (1979) 76(1):106–110.

Furman, T.C. et al., "Recombinant human insulin-like growth factor II expressed in *Escherichia coli*" *Bio/Technology* (Oct. 1987) 5:1047–1051.

di Guan, C. et al., "Vectors that facilitate the expression and purification of foreign peptides in *Escherichia coli* by fusion to maltose-binding protein" *Gene* (1988) 67:21–30.

Johnson, K.S. et al., "Vaccination against ovine cysticercosis using a defined recombinant antigen" *Nature* (1989) 338:585–587.

Miller, H.I. et al., "Cloning and expression of a yeast ubiquitin-protein cleaving activity in *Escherichia coli*" *Bio/Technology* (1989) 7:698–704.

LaVallie, E.R. et al., "A thioredoxin gene fusion expression system that circumvents inclusion body formation in the *E. coli* cytoplasm" *Bio/Technology* (1993) 11:187–193.

Schulz, M-F. et al., "Increased expression in *escherichia coli* of a synthetic gene encoding human somatomedin C after gene duplication and fusion" *J. Bacteriol.* (Dec. 1987) pp. 5385–5392.

Tobias, J.W., et al., "Cloning and functional analysis of ubiquitin-specific protease gene UPB1 of *saccharomyces cerevisiae*" *J. Biol. Chem.* (1991) 266(18):12021–12028.

Pugsley, A., "The complete general secretory pathway in gram-negative bacteria" *Microbiol. Rev.* (Mar. 1993) pp. 50–108.

Jacobson, G.R., et al., "Properties of a major protein released from *Escherichia coli*" *Biochem.* (1976) 15(11):2298–2302.

Joseph–Liauzun, E. et al., "Human recombinant interleukin-1β isolated from *Escherichia coli* by simple osmotic shock" *Gene* (1990) 86:291–295.

Nagahari, K., et al., "Secretion into the culture medium of a foreign gene product from *Escherichia coli*: Use of the *ompF* gene for secretion of β-endorphin" *EMBO J.* (1985) 4(13a):3589–3592.

Kato, C. et al., "Construction of an excretion vector and extracellular production of human growth hormone from *Estherichia coli*" *Gene* (1987) 54:197–202.

Holland, IB et al., "Haemolysin secretion from *E. coli*" *Biochimie* (1990) 72:131–141.

Bardwell, J.C.A. et al., "Identification of a protein required for disulfide bond formation in vivo" *Cell* (1991) 67:581–589.

Bayer, M.E., "Response of cell walls of *Escherichia coli* to a sudden reduction of the environmental osmotic pressure" *J. Bacteriol.* (Mar. 1967) pp. 1104–1112.

Chang, A.C.Y. et al., "Construction and characterization of amplifiable multicopy DNA cloning vehicles derived from the P15A cryptic miniplasmid" *J. Bacteriol.* (1978) pp. 1141–1156.

Cooper, D.N.W. et al., "Evidence for export of a muscle lectin from cytosol to extracellular matrix and for a novel secretory mechanism" *J. Cell Biol.* (1990) 110:1681–1691.

(List continued on next page.)

*Primary Examiner*—John Ulm
*Attorney, Agent, or Firm*—Morrison & Foerster

[57] ABSTRACT

The invention is directed to the use of a fusion partner that does not contain a leader sequence, as a means to increase the solubility and activity of recombinant polypeptides by facilitating the expression of fusion proteins, which are then transported out of the cytoplasm. The invention includes a nucleic acid encoding a fusion polypeptide comprising a mature interleukin-1-like polypeptide or a leader-deleted-translocating polypeptide, and a polypeptide of interest; as well as host cells comprising such nucleic acids, and fusion proteins so encoded. The invention also encompasses methods of using such nucleic acids to produce recombinant fusion polypeptides, mature polypeptides of interest, and purified compositions thereof.

23 Claims, 40 Drawing Sheets

OTHER PUBLICATIONS

Eisenberg, S.P. et al., "Primary structure and functional expression from complementary DNA of a human interleukin-1 receptor antagonist" *Nature* (1990) 343:341-346.

Eisenberg, S.P. et al., "Interleukin 1 receptor antagonist is a member of the interleukin 1 gene family: Evolution of a cytokine control mechanism" *Proc. Natl. Acad. Sci. USA* (1991) 88:5232-5236.

Engler, D.A. et al., "Cloning of authentic human epidermal growth factor as a bacterial secretory protein and its initial structure-function analysis by site-directed mutagenesis" *J. Biol. Chem.* (1988) 263(25):12384-12390.

Habazetti, J. et al., "Structure of hisactophilin is similar to interleukin-1β and fibroblast growth factor" *Nature* (1992) 359:855-858.

Hsiung, H.M. et al., "High level expression, efficient secretion and folding of human growth hormone in *Escherichia coli*" *Bio/Technology* (1986) 4:991-995.

Kamitani, S. et al., "Identification and characterization of an *Escherichia coli* gene required for the formation of correctly folded alkaline phosphatase, a periplasmic enzyme" *Embo J.* (1992) 11:57-62.

Kellenberger, E., "The 'bayer bridges' confronted with results from improved electron microscopy methods" *Mol. Microbiol.* (1990) 4(5):697-705.

Lunn, C.A. et al., "Localization of thioredoxin from *Escherichia coli* in an osmotically sensitive compartment" *J. Biol. Chem.* (1982) 257(19):11424-11430.

McDonald, N.Q. et al., "A structural superfamily of growth factors containing a cystine knot motif" *Cell* (1993) 73:421-424.

Muesch, A. et al., "A novel pathway for secretory proteins?" *TIBS 15* (Mar. 1990) pp. 86-88.

Peek, J.A. et al., "Characterization of a periplasmic thiol:disulfide interchange protein required for the functional maturation of secreted virulence factors of *Vibrio cholerae*" *Proc. Natl. Acad. Sc. USA* (1992) 89:6210-6214.

Priestle, J.P. et al., "Crystallographic refinement of interleukin 1β at 2.0 Å resolution" *Proc. Natl. Acad. Sci. USA* (1989) 86:9667-9671.

Rubartelli, A. et al., "A novel secretory pathway for interleukin-1β, a protein lacking a signal sequence" *Embo J.* (1990) 9(5):1503-1510.

Rubartelli, A. et al., "Secretion of thioredoxin by normal and neoplastic cells through a leaderless secretory pathway" *J. Biol. Chem.* (1992) 267(34):24161-24164.

Singer, I.I. et al., "Interleukin 1β is localized in the cytoplasmic ground substance but is largely absent from the golgi apparatus and plasma membranes of stimulated human monocytes" *J. Exp. Med.* (1988) 167:389-407.

Studier, F.W. et al., "Use of bacteriophage T7 RNA polymerase to direct selective high-level expression of cloned genes" *J. Mol. Biol.* (1986) 189:113-130.

Squires, C.H. et al., "Production and characterization of human basic fibroblast growth factor from *Escherichia coli*" *J. Biol. Chem.* (1988) 263(31):16297-16302.

Sutcliffe, J.G., "Nucleotide sequence of the ampicillin resistance gene of *Escherichia coli* plasmid pBR322" *Proc. Natl. Acad. Sci. USA* (1978) 75(8):3737-3741.

von Heijne, G. "A new method for predicting signal sequence cleavage sites" *Nucleic Acids Res.* (1986) 14(11):4683-4690.

Young, P. et al., "Modularity of protein function: chimeric interleukin 1βs containing specific protease inhibitor loops retain function of both molecules" *Biochem.* (1993) 32:5327-5331.

Zhang, J. et al., "Three-dimensional structure of human basic fibroblast growth factor, a structural homolog of interleukin 1β" *Proc. Natl. Acad. Sci. USA* (1991) 88:3446-3450.

Zhu, X. et al., "Three-dimensional structures of acidic and basic fibroblast growth factors" *Science* (1991) 251:90-94.

```
(1)dsbA:  (19)AQYEDGK---QYTTLE---KP-VAGAP FEE-VL
(2)IL1b:      APVR----SLNCTLRDSQQKSLVMSGP YELKAL
(3)IL1a:      APF-SFLSNVKYNFMRIIKYEFILNDA IRANDQ
(4)FGFb:  (14)GHFKDPK-RLYC-KNGG--F-FLRIHP -DGRV-
(5)FGFa:  ( 5)GNYKKPK-LLYCS-NGG--Y-FLRILP -DGTV- (1)  HISDNVKKKLPEGVKMTKYHVNF-MGGDL-GKDLTQAWAVAM-
(2)  HLQ---------GQDM-EQQVVFSMSF-VQGEESNDKIPVAL-
(3)  YLTAAAL------HNL-DEAVKFDMGA-YKSSKDDAKITVIL-
(4)  ---DGVREK-------SDPHIKLQ----LQAEE---RGVVSIK
(5)  ---DGTKDR-------SDQHIQLQ----LCAESI---GEVYIK (1)  AL----------GVEDKVTVPLFEGV--QKTQTIRSASDIRDVF
(2)  GLKEKNLYLSCVLKDDKPTLQL-ESVD-PKNYPKKKM-EKRFVF
(3)  RISKTQLYVTAQD-EDQPVLLK-EMPEIPKTIT--GS-ETNLLF
(4)  GV-CANRYL--AMKED---GRLLAS---------KCVTDECFFF
(5)  ST-ETGQFL--AMDTD---GLLYGS------QTP---NEECLFL (1)  INAGI--KGEEYDAA KYQLNPQGMDTS---NMDVF-V------
(2)  NKIEINNKL-EFESA --QFPNWYISTSQAENMPVF-LGGTKGG
(3)  FWETHGTKN-YFTSV --AHPNLFIATKQ--DYWVC-L--AGGP
(4)  ERLESNNYN-TYRSR KY--TSWYVALKRTGQ---YKLGSKTGP
(5)  ERLEENHYN-TYISK KHAEKHWFVGLKKNGR---SKLGPRTHF (1)  QQYAD-TVKYL--SEKK
(2)  QDITDFTMQFV----SS
(3)  PSITDFQILEN----QA
(4)  GQKA---ILFLPMSAKS
(5)  GQKA---ILFLPLPVSS
```

FIG. 1

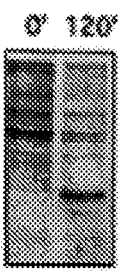 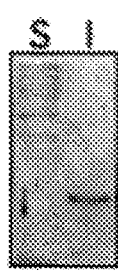  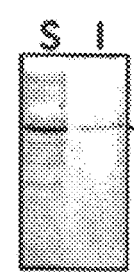
FIG. 7A  FIG. 7B      FIG. 7C  FIG. 7D
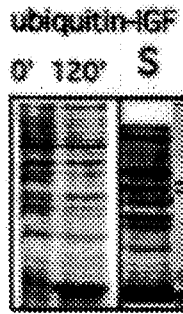 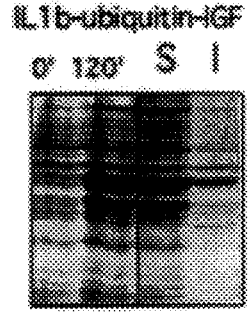 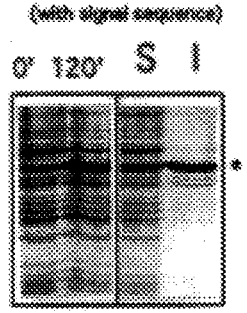 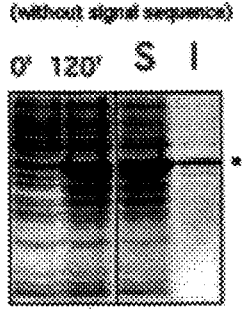
FIG. 8A  FIG. 8B  FIG. 8C  FIG. 8D

```
ATGAAAAAGA TTTGGCTGGC GCTGGCTGGT TTAGTTTTAG    40
CGTTTAGCGC ATCGGCGGCG CAGTATGAAG ATGGTAAACA    80
GTACACTACC CTGGAAAAAC CGGTAGCTGG CGCGCCGCAA   120
GTGCTGGAGT TTTTCTCTTT CTTCTGCCCG CACTGCTATC   160
AGTTTGAAGA AGTTCTGCAT ATTTCTGATA ATGTGAAGAA   200
AAAACTGCCG GAAGGCGTGA AGATGACTAA ATACCACGTC   240
AACTTCATGG GTGGTGACCT GGGCAAAGAT CTGACTCAGG   280
CATGGGCTGT GGCGATGGCG CTGGGCGTGG AAGACAAAGT   320
GACTGTTCCG CTGTTTGAAG GCGTACAGAA AACCCAGACC   360
ATTCGTTCTG CTTCTGATAT CCGCGATGTA TTTATCAACG   400
CAGGTATTAA AGGTGAAGAG TACGACGCGG CGTGGAACAG   440
CTTCGTGGTG AAATCTCTGG TCGCTCAGCA GGAAAAAGCT   480
GCAGCTGACG TGCAATTGCG TGGCGTTCCG GCGATGTTTG   520
TTAACGGTAA ATATCAGCTG AATCCGCAGG GTATGGATAC   560
CAGCAATATG GATGTTTTTG TTCAGCAGTA TGCTGATACA   600
GTGAAATATC TGTCCGAGAA AAAACATCAT CACCATCATC   640
ACAGCATGGG TTCTCTGAAA CCTATCTTTG ACGCTCAGAA   680
GATTGAGTGG CGTCATAGCA TGCACCGCGG TCTCGAGTAA   720
```

FIGURE 20

| | | | | |
|---|---|---|---|---|
| ATGGCGCAGT | ATGAAGATGG | TAAACAGTAC | ACTACCCTGG | 40 |
| AAAAACCGGT | AGCTGGCGCG | CCGCAAGTGC | TGGAGTTTTT | 80 |
| CTCTTTCTTC | TGCCCGCACT | GCTATCAGTT | TGAAGAAGTT | 120 |
| CTGCATATTT | CTGATAATGT | GAAGAAAAAA | CTGCCGGAAG | 160 |
| GCGTGAAGAT | GACTAAATAC | CACGTCAACT | TCATGGGTGG | 200 |
| TGACCTGGGC | AAAGATCTGA | CTCAGGCATG | GCTGTGGCG | 240 |
| ATGGCGCTGG | GCGTGGAAGA | CAAAGTGACT | GTTCCGCTGT | 280 |
| TGAAGGCGT | ACAGAAAACC | CAGACCATTC | GTTCTGCTTC | 320 |
| TGATATCCGC | GATGTATTTA | TCAACGCAGG | TATTAAAGGT | 360 |
| GAAGAGTACG | ACGCGGCGTG | GAACAGCTTC | GTGGTGAAAT | 400 |
| CTCTGGTCGC | TCAGCAGGAA | AAAGCTGCAG | CTGACGTGCA | 440 |
| ATTGCGTGGC | GTTCCGGCGA | TGTTTGTTAA | CGGTAAATAT | 480 |
| CAGCTGAATC | CGCAGGGTAT | GGATACCAGC | AATATGGATG | 520 |
| TTTTTGTTCA | GCAGTATGCT | GATACAGTGA | AATATCTGTC | 560 |
| CGAGAAAAAA | CATCATCACC | ATCATCACAG | CATGGGTTCT | 600 |
| CTGAAACCTA | TCTTTGACGC | TCAGAAGATT | GAGTGGCGTC | 640 |
| ATAGCATGCA | CCGCGGTCTC | GAGTAA | | 666 |

FIGURE 21

```
ATGGCGCAGT ATGAAGATGG TAAACAGTAC ACTACCCTGG   40
AAAAACCGGT AGCTGGCGCG CCGCAAGTGC TGGAGTTTTT   80
CTCTTTCTTC TGCCCGCACT GCTATCAGTT TGAAGAAGTT  120
CTGCATATTT CTGATAATGT GAAGAAAAA CTGCCGGAAG  160
GCGTGAAGAT GACTAAATAC CACGTCAACT TCATGGGTGG  200
TGACCTGGGC AAAGATCTGA CTCAGGCATG GGCTGTGGCG  240
ATGGCGCTGG GCGTGGAAGA CAAAGTGACT GTTCCGCTGT  280
TTGAAGGCGT ACAGAAAACC CAGACCATTC GTTCTGCTTC  320
TGATATCCGC GATGTATTTA TCAACGCAGG TATTAAAGGT  360
GAAGAGTACG ACGCGGCGTG GAACAGCTTC GTGGTGAAAT  400
CTCTGGTCGC TCAGCAGGAA AAAGCTGCAG CTGACGTGCA  440
ATTGCGTGGC GTTCCGGCGA TGTTTGTTAA CGGTAAATAT  480
CAGCTGAATC CGCAGGGTAT GGATACCAGC AATATGGATG  520
TTTTTGTTCA GCAGTATGCT GATACAGTGA AATATCTGTC  560
CGAGAAAAAA CATCATCACC ATCATCACAG CATGCCCGGC  600
AAGCAGCTAG AAGACGGTAG AACGCTGTCT GATTACAACA  640
TTCAGAAGGA GTCCACCTTA CATCTTGTGC TAAGGCTCCG  680
CGGTGGTGGT CCGGAAACCC TGTGCGGTGC TGAACTGGTT  720
GACGCTCTTC AGTTCGTTTG CGGTGACCGT GGTTTCTACT  760
TCAACAAACC GACCGGTTAC GGTTCCTCCT CCCGTCGTGC  800
TCCGCAGACC GGTATCGTTG ACGAATGCTG CTTCCGGTCC  840
TGCGACCTGC GTCGTCTGGA AATGTACTGC GCTCCGCTGA  880
AACCGGCTAA ATCCGCTTAA                        900
```

FIGURE 22

```
ATGGCGCAGT ATGAAGATGG TAAACAGTAC ACTACCCTGG    40
AAAAACCGGT AGCTGGCGCG CCGCAAGTGC TGGAGTTTTT    80
CTCTTTCTTC TGCCCGCACT GCTATCAGTT TGAAGAAGTT   120
CTGCATATTT CTGATAATGT GAAGAAAAA CTGCCGGAAG    160
GCGTGAAGAT GACTAAATAC CACGTCAACT TCATGGGTGG   200
TGACCTGGGC AAAGATCTGA CTCAGGCATG GCTGTGGCG    240
ATGGCGCTGG GCGTGGAAGA CAAAGTGACT GTTCCGCTGT   280
TTGAAGGCGT ACAGAAACC CAGACCATTC GTTCTGCTTC    320
TGATATCCGC GATGTATTTA TCAACGCAGG TATTAAAGGT   360
GAAGAGTACG ACGCGGCGTG GAACAGCTTC GTGGTGAAAT   400
CTCTGGTCGC TCAGCAGGAA AAAGCTGCAG CTGACGTGCA   440
ATTGCGTGGC GTTCCGGCGA TGTTTGTTAA CGGTAAATAT   480
CAGCTGAATC CGCAGGGTAT GGATACCAGC AATATGGATG   520
TTTTTGTTCA GCAGTATGCT GATACAGTGA AATATCTGTC   560
CGAGAAAAAA CATCATCACC ATCATCACAG CATGCAGATT   600
TTCGTCAAGA CTTTGACCGG TAAAACCATA ACATTGGAAG   640
TTGAACCTTC CGATACCATC GAGAACGTTA AGGCGAAAAT   680
TCAAGACAAG GAAGGTATCC CTCCAGATCA ACAAAGATTG   720
ATCTTTGCCG GCAAGCAGCT AGAAGACGGT AGAACGCTGT   760
CTGATTACAA CATTCAGAAG GAGTCCACCT TACATCTTGT   800
GCTAAGGCTC CGCGGTGGTG GTCCGGAAAC CCTGTGCGGT   840
GCTGAACTGG TTGACGCTCT TCAGTTCGTT TGCGGTGACC   880
GTGGTTTCTA CTTCAACAAA CCGACCGGTT ACGGTTCCTC   920
CTCCCGTCGT GCTCCGCAGA CCGGTATCGT TGACGAATGC   960
TGCTTCCGGT CCTGCGACCT GCGTCGTCTG GAAATGTACT  1000
GCGCTCCGCT GAAACCGGCT AAATCCGCTT AA          1032
```

FIGURE 23

| | | | | |
|---|---|---|---|---|
| ATGAAAAAGA | TTTGGCTGGC | GCTGGCTGGT | TTAGTTTTAG | 40 |
| CGTTTAGCGC | ATCGGCGGCG | CAGTATGAAG | ATGGTAAACA | 80 |
| GTACACTACC | CTGGAAAAAC | CGGTAGCTGG | CGCGCCGCAA | 120 |
| GTGCTGGAGT | TTTTCTCTTT | CTTCTGCCCG | CACTGCTATC | 160 |
| AGTTTGAAGA | AGTTCTGCAT | ATTTCTGATA | ATGTGAAGAA | 200 |
| AAAACTGCCG | GAAGGCGTGA | AGATGACTAA | ATACCACGTC | 240 |
| AACTTCATGG | GTGGTGACCT | GGGCAAAGAT | CTGACTCAGG | 280 |
| CATGGGCTGT | GGCGATGGCG | CTGGGCGTGG | AAGACAAAGT | 320 |
| GACTGTTCCG | CTGTTTGAAG | GCGTACAGAA | AACCCAGACC | 360 |
| ATTCGTTCTG | CTTCTGATAT | CCGCGATGTA | TTTATCAACG | 400 |
| CAGGTATTAA | AGGTGAAGAG | TACGACGCGG | CGTGGAACAG | 440 |
| CTTCGTGGTG | AAATCTCTGG | TCGCTCAGCA | GGAAAAAGCT | 480 |
| GCAGCTGACG | TGCAATTGCG | TGGCGTTCCG | GCGATGTTTG | 520 |
| TTAACGGTAA | ATATCAGCTG | AATCCGCAGG | GTATGGATAC | 560 |
| CAGCAATATG | GATGTTTTTG | TTCAGCAGTA | TGCTGATACA | 600 |
| GTGAAATATC | TGTCCGAGAA | AAAATAA | | 627 |

FIGURE 24

```
ATGGCTGATG ACGCGGCAAT TCAACAAACG TTAGCCAAAA    40
TGGGCATCAA AAGCAGCGAT ATTCAGCCCG CGCCTGTAGC    80
TGGCATGAAG ACAGTTCTGA CTAACAGCGG CGTGTTGTAC   120
ATCACCGATG ATGGTAAACA TATCATTCAG GGGCCAATGT   160
ATGACGTTAG TGGCACGGCT CCGGTCAATG TCACCAATAA   200
GATGCTGTTA AAGCAGTTGA ATGCGCTTGA AAAAGAGATG   240
ATCGTTTATA AAGCGCCGCA GGAAAAACAC GTCATCACCG   280
TGTTTACTGA TATTACCGGT AGCGGTTCTG GTAAACTGCA   320
TGAGCAAATG GCAGACTACA ACGCGCTGGG GATCACCGTG   360
CGTTATCTTG CTTTCCCGCG CCAGGGGCTG ACAGCGATG    400
CAGAGAAAGA AATGAAAGCT ATCTGGTGTG CGAAAGATAA   440
AAACAAAGCG TTTGATGATG TGATGGCAGG TAAAAGCGTC   480
GCACCAGCCA GTTGCGACGT GGATATTGCC GACCATTACG   520
CACTTGGCGT CCAGCTTGGC GTTAGCGGTA CTCCGGCAGT   560
TGTGCTGAGC AATGGCACAC TTGTTCCGGG TTACCAGCCG   600
AAAGAGATGA AAGAATTCCT CGACGAACAC CAAAAAATGA   640
CCAGCGGTAA ATCTGGTGGT AGCATGC                 667
```

FIGURE 25

```
ATGGCGCAGT ATGAAGATGG TAAACAGTAC ACTACCCTGG    40
AAAAACCGGT AGCTGGCGCG CCGCAAGTGC TGGAGTTTTT    80
CTCTTTCTTC TGCCCGCACT GCTATCAGTT TGAAGAAGTT   120
CTGCATATTT CTGATAATGT GAAGAAAAA CTGCCGGAAG    160
GCGTGAAGAT GACTAAATAC CACGTCAACT TCATGGGTGG   200
TGACCTGGGC AAAGATCTGA CTCAGGCATG GCTGTGGCG    240
ATGGCGCTGG GCGTGGAAGA CAAAGTGACT GTTCCGCTGT   280
TTGAAGGCGT ACAGAAAACC CAGACCATTC GTTCTGCTTC   320
TGATATCCGC GATGTATTTA TCAACGCAGG TATTAAAGGT   360
GAAGAGTACG ACGCGGCGTG GAACAGCTTC GTGGTGAAAT   400
CTCTGGTCGC TCAGCAGGAA AAAGCTGCAG CTGACGTGCA   440
ATTGCGTGGC GTTCCGGCGA TGTTTGTTAA CGGTAAATAT   480
CAGCTGAATC CGCAGGGTAT GGATACCAGC AATATGGATG   520
TTTTTGTTCA GCAGTATGCT GATACAGTGA AATATCTGTC   560
CGAGAAAAAA TAA                                573
```

FIGURE 26

| | | | | |
|---|---|---|---|---|
| ATGGCGCAGT | ATGAAGATGG | TAAACAGTAC | ACTACCCTGG | 40 |
| AAAAACCGGT | AGCTGGCGCG | CCGCAAGTGC | TGGAGTTTTT | 80 |
| CTCTTTCTTC | TGCCCGCACT | GCTATCAGTT | TGAAGAAGTT | 120 |
| CTGCATATTT | CTGATAATGT | GAAGAAAAA | CTGCCGGAAG | 160 |
| GCGTGAAGAT | GACTAAATAC | CACGTCAACT | TCATGGGTGG | 200 |
| TGACCTGGGC | AAAGATCTGA | CTCAGGCATG | GGCTGTGGCG | 240 |
| ATGGCGCTGG | GCGTGGAAGA | CAAAGTGACT | GTTCCGCTGT | 280 |
| TGAAGGCGT | ACAGAAAACC | CAGACCATTC | GTTCTGCTTC | 320 |
| TGATATCCGC | GATGTATTTA | TCAACGCAGG | TATTAAAGGT | 360 |
| GAAGAGTACG | ACGCGGCGTG | GAACAGCTTC | GTGGTGAAAT | 400 |
| CTCTGGTCGC | TCAGCAGGAA | AAAGCTGCAG | CTGACGTGCA | 440 |
| ATTGCGTGGC | GTTCCGGCGA | TGTTTGTTAA | CGGTAAATAT | 480 |
| CAGCTGAATC | CGCAGGGTAT | GGATACCAGC | AATATGGATG | 520 |
| TTTTTGTTCA | GCAGTATGCT | GATACAGTGA | AATATCTGTC | 560 |
| CGAGAAAAAA | CATCATCACC | ATCATCACAG | CATGCCCGGG | 600 |
| CTCGAGTAAG | CTTATGCAT | | | 619 |

FIGURE 27

```
ATGGCGCAGT ATGAAGATGG TAAACAGTAC ACTACCCTGG    40
AAAAACCGGT AGCTGGCGCG CCTTCTGGTT CTTTCATGGG    80
TGGTGACCTG GGCAAAGATC TGACTCAGGC ATGGGCTGTG   120
GCGATGGCGC TGGGCGTGGA AGACAAAGTG ACTGTTCCGC   160
TGTTTGAAGG CGTACAGAAA ACCCAGACCA TTCGTTCTGC   200
TTCTGATATC CGCGATGTAT TTATCAACGC AGGTATTAAA   240
GGTGAAGAGT ACGACGCGGC GTGGAACAGC TTCGTGGTGA   280
AATCTCTGGT CGCTCAGCAG GAAAAAGCTG CAGCTGACGT   320
GCAATTGCGT GGCGTTCCGG CGATGTTTGT TAACGGTAAA   360
TATCAGCTGA ATCCGCAGGG TATGGATACC AGCAATATGG   400
ATGTTTTTGT TCAGCAGTAT GCTGATACAG TGAAATATCT   440
GTCCGAGAAA AAATAA                              456
```

FIGURE 28

```
ATGGCGCAGT ATGAAGATGG TAAACAGTAC ACTACCCTGG    40
AAAAACCGGT AGCTGGCGCG CCGCAAGTGC TGGAGTTTTT    80
CTCTTTCTTC TGCCCGCACT GCTATCAGTT TGAAGAAGTT   120
CTGCATATTT CTGATAATGT GAAGAAAAA CTGCCGGAAG   160
GCGTGAAGAT GACTAAATAC CACGTCAACT TCATGGGTGG   200
TGACCTGGGC AAAGATCTGA CTCAGGCATG GGCTGTGGCG   240
ATGGCGCTGG GCGTGGAAGA CAAAGTGACT GTTCCGCTGT   280
TTGAAGGCGT ACAGAAAACC CAGACCATTC GTTCTGCTTC   320
TGATATCCGC GATGTATTTA TCAACGCAGG TATTAAAGGT   360
GAAGAGTACG ACGCGGCGTG GAACAGCTTC GTGGTGAAAT   400
CTCTGGTCGC TCAGCAGGAA AAAGCTGCAG CTGACGTGCA   440
ATTGCGTGGC GTTCCGGCGA TGTTTGTTAA CGGTAAATAT   480
CAGCTGAATC CGCAGGGTAT GGATACCAGC AATATGGATG   520
TTTTTGTTCA GCAGTATGCT GATACAGTGA AATATCTGTC   560
CGAGAAAAAA CATCATCACC ATCATCACAG CATGCAGATT   600
TTCGTCAAGA CTTTGACCGG TAAAACCATA ACATTGGAAG   640
TTGAATCTTC CGATACCATC GACAACGTTA AGTCGAAAAT   680
TCAAGACAAG GAAGGTATCC CTCCAGATCA ACAAAGATTG   720
ATCTTTGCCG GTAAGCAGCT AGAAGACGGT AGAACGCTGT   760
CTGATTACAA CATTCAGAAG GAGTCCACCT TACATCTTGT   800
GCTAAGGCTC CGCGGTGGTG GTCCGGAAAC CCTGTGCGGT   840
GCTGAACTGG TTGACGCTCT GCAGTTCGTT TGCGGTGACC   880
GTGGTTTCTA CTTCAACAAA CCGACCGGTT ACGGTTCCTC   920
CTCCCGTCGT GCTCCGCAGA CCGGTATCGT TGACGAATGC   960
TGCTTCCGGT CCTGCGACCT GCGTCGTCTG GAAATGTACT  1000
GCGCTCCGCT GAAACCGGCT AAATCCGCTT AA          1032
```

FIGURE 29

```
ATGGCTGATG ACGCGGCAAT TCAACAAACG TTAGCCAAAA    40
TGGGCATCAA AAGCAGCGAT ATTCAGCCCG CGCCTGTAGC    80
TGGCATGAAG ACAGTTCTGA CTAACAGCGG CGTGTTGTAC   120
ATCACCGATG ATGGTAAACA TATCATTCAG GGGCCAATGT   160
ATGACGTTAG TGGCACGGCT CCGGTCAATG TCACCAATAA   200
GATGCTGTTA AAGCAGTTGA ATGCGCTTGA AAAAGAGATG   240
ATCGTTTATA AAGCGCCGCA GGAAAAACAC GTCATCACCG   280
TGTTTACTGA TATTACCTGT GGTTACTGCC ACAAACTGCA   320
TGAGCAAATG GCAGACTACA ACGCGCTGGG GATCACCGTG   360
CGTTATCTTG CTTTCCGCG CCAGGGGCTG GACAGCGATG   400
CAGAGAAAGA AATGAAAGCT ATCTGGTGTG CGAAAGATAA   440
AAACAAAGCG TTTGATGATG TGATGGCAGG TAAAAGCGTC   480
GCACCAGCCA GTTGCGACGT GGATATTGCC GACCATTACG   520
CACTTGGCGT CCAGCTTGGC GTTAGCGGTA CTCCGGCAGT   560
TGTGCTGAGC AATGGCACAC TTGTTCCGGG TTACCAGCCG   600
AAAGAGATGA AGAATTCCT CGACGAACAC CAAAAAATGA   640
CCAGCGGTAA ATCTGGTGGT AGCATGCAGA TTTTCGTCAA   680
GACTTTGACC GGTAAAACCA TAACATTGGA AGTTGAACCT   720
TCCGATACCA TCGAGAACGT TAAGGCGAAA ATTCAAGACA   760
AGGAAGGTAT CCCTCCAGAT CAACAAAGAT TGATCTTTGC   800
CGGCAAGCAG CTAGAAGACG GTAGAACGCT GTCTGATTAC   840
AACATTCAGA AGGAGTCCAC CTTACATCTT GTGCTAAGGC   880
TCCGCGGTGG TGGTCCGGAA ACCCTGTGCG GTGCTGAACT   920
GGTTGACGCT CTTCAGTTCG TTTGCGGTGA CCGTGGTTTC   960
TACTTCAACA AACCGACCGG TTACGGTTCC TCCTCCCGTC  1000
GTGCTCCGCA GACCGGTATC GTTGACGAAT GCTGCTTCCG  1040
GTCCTGCGAC CTGCGTCGTC TGGAAATGTA CTGCGCTCCG  1080
CTGAAACCGG CTAAATCCGC TTAA                   1104
```

FIGURE 30

```
ATGGCTGATG ACGCGGCAAT TCAACAAACG TTAGCCAAAA     40
TGGGCATCAA AAGCAGCGAT ATTCAGCCCG CGCCTGTAGC     80
TGGCATGAAG ACAGTTCTGA CTAACAGCGG CGTGTTGTAC    120
ATCACCGATG ATGGTAAACA TATCATTCAG GGGCCAATGT    160
ATGACGTTAG TGGCACGGCT CCGGTCAATG TCACCAATAA    200
GATGCTGTTA AAGCAGTTGA ATGCGCTTGA AAAAGAGATG    240
ATCGTTTATA AAGCGCCGCA GGAAAAACAC GTCATCACCG    280
TGTTTACTGA TATTACCGGT AGCGGTTCTG GTAAACTGCA    320
TGAGCAAATG GCAGACTACA ACGCGCTGGG GATCACCGTG    360
CGTTATCTTG CTTTCCCGCG CCAGGGGCTG ACAGCGATG     400
CAGAGAAAGA AATGAAAGCT ATCTGGTGTG CGAAAGATAA    440
AAACAAAGCG TTTGATGATG TGATGGCAGG TAAAAGCGTC    480
GCACCAGCCA GTTGCGACGT GGATATTGCC GACCATTACG    520
CACTTGGCGT CCAGCTTGGC GTTAGCGGTA CTCCGGCAGT    560
TGTGCTGAGC AATGGCACAC TTGTTCCGGG TTACCAGCCG    600
AAAGAGATGA AGAATTCCT CGACGAACAC CAAAAAATGA     640
CCAGCGGTAA ATCTGGTGGT AGCATGCACC GCGGTGGTGG    680
TCCGGAAACC CTGTGCGGTG CTGAACTGGT TGACGCTCTT    720
CAGTTCGTTT GCGGTGACCG TGGTTTCTAC TTCAACAAAC    760
CGACCGGTTA CGGTTCCTCC TCCCGTCGTG CTCCGCAGAC    800
CGGTATCGTT GACGAATGCT GCTTCCGGTC CTGCGACCTG    840
CGTCGTCTGG AAATGTACTG CGCTCCGCTG AAACCGGCTA    880
AATCCGCTTA A                                   891
```

FIGURE 31

```
ATGGCTGATG ACGCGGCAAT TCAACAAACG TTAGCCAAAA   40
TGGGCATCAA AAGCAGCGAT ATTCAGCCCG CGCCTGTAGC   80
TGGCATGAAG ACAGTTCTGA CTAACAGCGG CGTGTTGTAC  120
ATCACCGATG ATGGTAAACA TATCATTCAG GGGCCAATGT  160
ATGACGTTAG TGGCACGGCT CCGGTCAATG TCACCAATAA  200
GATGCTGTTA AAGCAGTTGA ATGCGCTTGA AAAAGAGATG  240
ATCGTTTATA AAGCGCCGCA GGAAAAACAC GTCATCACCG  280
TGTTTACTGA TATTACCTGT GGTTACTGCC ACAAACTGCA  320
TGAGCAAATG GCAGACTACA ACGCGCTGGG GATCACCGTG  360
CGTTATCTTG CTTTCCCGCG CCAGGGGCTG ACAGCGATG   400
CAGAGAAAGA AATGAAAGCT ATCTGGTGTG CGAAAGATAA  440
AAACAAAGCG TTTGATGATG TGATGGCAGG TAAAAGCGTC  480
GCACCAGCCA GTTGCGACGT GGATATTGCC GACCATTACG  520
CACTTGGCGT CCAGCTTGGC GTTAGCGGTA CTCCGGCAGT  560
TGTGCTGAGC AATGGCACAC TTGTTCCGGG TTACCAGCCG  600
AAAGAGATGA AGAATTCCT  CGACGAACAC CAAAAAATGA  640
CCAGCGGTAA ATCTGGTGGT AGCATGCACC GCGGTGGTGG  680
TCCGGAAACC CTGTGCGGTG CTGAACTGGT TGACGCTCTT  720
CAGTTCGTTT GCGGTGACCG TGGTTTCTAC TTCAACAAAC  760
CGACCGGTTA CGGTTCCTCC TCCCGTCGTG CTCCGCAGAC  800
CGGTATCGTT GACGAATGCT GCTTCCGGTC CTGCGACCTG  840
CGTCGTCTGG AAATGTACTG CGCTCCGCTG AAACCGGCTA  880
AATCCGCTTA A                                 891
```

FIGURE 32

```
ATGGCTGATG ACGCGGCAAT TCAACAAACG TTAGCCAAAA    40
TGGGCATCAA AAGCAGCGAT ATTCAGCCCG CGCCTGTAGC    80
TGGCATGAAG ACAGTTCTGA CTAACAGCGG CGTGTTGTAC   120
ATCACCGATG ATGGTAAACA TATCATTCAG GGGCCAATGT   160
ATGACGTTAG TGGCACGGCT CCGGTCAATG TCACCAATAA   200
GATGCTGTTA AAGCAGTTGA ATGCGCTTGA AAAAGAGATG   240
ATCGTTTATA AAGCGCCGCA GGAAAAACAC GTCATCACCG   280
TGTTTACTGA TATTACCTGT GGTTACTGCC ACAAACTGCA   320
TGAGCAAATG GCAGACTACA ACGCGCTGGG GATCACCGTG   360
CGTTATCTTG CTTTCCCGCG CCAGGGGCTG GACAGCGATG   400
CAGAGAAAGA AATGAAAGCT ATCTGGTGTG CGAAAGATAA   440
AAACAAAGCG TTTGATGATG TGATGGCAGG TAAAAGCGTC   480
GCACCAGCCA GTTGCGACGT GGATATTGCC GACCATTACG   520
CACTTGGCGT CCAGCTTGGC GTTAGCGGTA CTCCGGCAGT   560
TGTGCTGAGC AATGGCACAC TTGTTCCGGG TTACCAGCCG   600
AAAGAGATGA AGAATTCCT CGACGAACAC CAAAAAATGA   640
CCAGCGGTAA ATCTGGTGGT AGCATGC                 667
```

FIGURE 33

```
ATGGCACCTG TACGATCACT GAACTGCACG CTCCGGGACT    40
CACAGCAAAA AAGCTTGGTG ATGTCTGGTC CATATGAACT    80
GAAAGCTCTC CACCTCCAGG GACAGGATAT GGAGCAACAA   120
GTGGTGTTCT CCATGTCCTT TGTACAAGGA GAAGAAAGTA   160
ATGACAAAAT ACCTGTGGCC TTGGGCCTCA AGGAAAAGAA   200
TCTGTACCTG TCCTGCGTGT TGAAAGATGA TAAGCCCACT   240
CTACAGCTGG AGAGTGTAGA TCCCAAAAAT TACCCAAAGA   280
AGAAGATGGA AAAGCGATTT GTCTTCAACA AGATAGAAAT   320
CAATAACAAG CTGGAATTTG AGTCTGCCCA GTTCCCCAAC   360
TGGTACATCA GCACCTCTCA AGCAGAAAAC ATGCCCGTCT   400
TCCTGGGAGG GACCAAAGGC GGCCAGGATA TAACTGACTT   440
CACCATGCAA TTTGTGTCTT CCGACCGCGG TGGCATGCAC   480
CGCGGTGGTG GTCCGGAAAC CCTGTGCGGT GCTGAACTGG   520
TTGACGCTCT GCAGTTCGTT TGCGGTGACC GTGGTTTCTA   560
CTTCAACAAA CCGACCGGTT ACGGTTCCTC CTCCCGTCGT   600
GCTCCGCAGA CCGGTATCGT TGACGAATGC TGCTTCCGGT   640
CCTGCGACCT GCGTCGTCTG GAAATGTACT GCGCTCCGCT   680
GAAACCGGCT AAATCCGCTT AA                      702
```

FIGURE 34

```
ATGGCACCTG TACGATCACT GAACTGCACG CTCCGGGACT      40
CACAGCAAAA AAGCTTGGTG ATGTCTGGTC CATATGAACT      80
GAAAGCTCTC CACCTCCAGG GACAGGATAT GGAGCAACAA     120
GTGGTGTTCT CCATGTCCTT TGTACAAGGA GAAGAAAGTA     160
ATGACAAAAT ACCTGTGGCC TTGGGCCTCA AGGAAAAGAA     200
TCTGTACCTG TCCTGCGTGT TGAAAGATGA TAAGCCCACT     240
CTACAGCTGG AGAGTGTAGA TCCCAAAAAT TACCCAAAGA     280
AGAAGATGGA AAAGCGATTT GTCTTCAACA AGATAGAAAT     320
CAATAACAAG CTGGAATTTG AGTCTGCCCA GTTCCCCAAC     360
TGGTACATCA GCACCTCTCA AGCAGAAAAC ATGCCCGTCT     400
TCCTGGGAGG GACCAAAGGC GGCCAGGATA TAACTGACTT     440
CACCATGCAA TTTGTGTCTT CCTAA                     465
```

FIGURE 35

```
ATGGCACCTG TACGATCACT GAACTGCACG CTCCGGGACT    40
CACAGCAAAA AAGCTTGGTG ATGTCTGGTC CATATGAACT    80
GAAAGCTCTC CACCTCCAGG GACAGGATAT GGAGCAACAA   120
GTGGTGTTCT CCATGTCCTT TGTACAAGGA GAAGAAAGTA   160
ATGACAAAAT ACCTGTGGCC TTGGGCCTCA AGGAAAAGAA   200
TCTGTACCTG TCCTGCGTGT TGAAAGATGA TAAGCCCACT   240
CTACAGCTGG AGAGTGTAGA TCCCAAAAAT TACCCAAAGA   280
AGAAGATGGA AAAGCGATTT GTCTTCAACA AGATAGAAAT   320
CAATAACAAG CTGGAATTTG AGTCTGCCCA GTTCCCCAAC   360
TGGTACATCA GCACCTCTCA AGCAGAAAAC ATGCCCGTCT   400
TCCTGGAGG GACCAAAGGC GGCCAGGATA TAACTGACTT   440
CACCATGCAA TTTGTGTCTT CCGACCGCGG TGGCATGC    478
```

FIGURE 36

```
ATGGCACCTG  TACGATCACT  GAACTGCACG  CTCGGGGACT    40
CACAGCAAAA  AAGCTTGGTG  ATGTCTGGTC  CATATGAACT    80
GAAAGCTCTC  CACCTCCAGG  ACAGGATAT   GGAGCAACAA   120
GTGGTGTTCT  CCATGTCCTT  TGTACAAGGA  GAAGAAAGTA   160
ATGACAAAAT  ACCTGTGGCC  TTGGGCCTCA  AGGAAAAGAA   200
TCTGTACCTG  TCCTGCGTGT  TGAAGATGA   TAAGCCCACT   240
CTACAGCTGG  AGAGTGTAGA  TCCCAAAAAT  TACCCAAAGA   280
AGAAGATGGA  AAAGCGATTT  GTCTTCAACA  AGATAGAAAT   320
CAATAACAAG  CTGGAATTTG  AGTCTGCCCA  GTTCCCCAAC   360
TGGTACATCA  GCACCTCTCA  AGCAGAAAAC  ATGCCCGTCT   400
TCCTGGGAGG  GACCAAAGGC  GGCCAGGATA  TAACTGACTT   440
CACCATGCAA  TTTGTGTCTT  CCAGCATGC                469
```

FIGURE 37

| | | | | |
|---|---|---|---|---|
| ATGCGGCCGT | CTGGGAGAAA | ATCCAGCAAG | ATGCAAGCCT | 40 |
| TCAGAATCTG | GGATGTTAAC | CAGAAGACCT | TCTATCTGAG | 80 |
| GAACAACCAA | CTAGTTGCTG | GATACTTGCA | AGGACCAAAT | 120 |
| GTCAATTTAG | AAGAAAAGAT | AGATGTGGTA | CCCATTGAGC | 160 |
| CTCATGCTCT | GTTCTTGGGA | ATCCATGGAG | GGAAGATGTG | 200 |
| CCTGTCCTGT | GTCAAGTCTG | GTGATGAGAC | CAGACTCCAG | 240 |
| CTGGAGGCAG | TTAACATCAC | TGACCTGAGC | GAGAACAGAA | 280 |
| AGCAGGACAA | GCGCTTCGCC | TTCATCCGCT | CAGACAGTGG | 320 |
| CCCCACCACC | AGTTTTGAGT | CTGCCGCCTG | CCCCGGTTGG | 360 |
| TTCCTCTGCA | CAGCGATGGA | AGCTGACCAG | CCCGTCAGCC | 400 |
| TCACCAATAT | GCCTGACGAA | GGCGTCATGG | TCACCAAATT | 440 |
| CTACTTCCAG | GAGGACGAGT | CTGGTTCTGG | TGACGATGAC | 480 |
| GATAAGAGCA | TGCACCGCGG | TGGTGGTCCG | GAAACCCTGT | 520 |
| GCGGTGCTGA | ACTGGTTGAC | GCTCTTCAGT | TCGTTTGCGG | 560 |
| TGACCGTGGT | TTCTACTTCA | ACAAACCGAC | CGGTTACGGT | 600 |
| TCCTCCTCCC | GTCGTGCTCC | GCAGACCGGT | ATCGTTGACG | 640 |
| AATGCTGCTT | CCGGTCCTGC | GACCTGCGTC | GTCTGGAAAT | 680 |
| GTACTGCGCT | CCGCTGAAAC | CGGCTAAATC | CGCTTAA | 717 |

FIGURE 38

| | | | | |
|---|---|---|---|---|
| ATGCGGCCGT | CTGGGAGAAA | ATCCAGCAAG | ATGCAAGCCT | 40 |
| TCAGAATCTG | GGATGTTAAC | CAGAAGACCT | TCTATCTGAG | 80 |
| GAACAACCAA | CTAGTTGCTG | GATACTTGCA | AGGACCAAAT | 120 |
| GTCAATTTAG | AAGAAAGAT | AGATGTGGTA | CCCATTGAGC | 160 |
| CTCATGCTCT | GTTCTTGGGA | ATCCATGGAG | GGAAGATGTG | 200 |
| CCTGTCCTGT | GTCAAGTCTG | GTGATGAGAC | CAGACTCCAG | 240 |
| CTGGAGGCAG | TTAACATCAC | TGACCTGAGC | GAGAACAGAA | 280 |
| AGCAGGACAA | GCGCTTCGCC | TTCATCCGCT | CAGACAGTGG | 320 |
| CCCCACCACC | AGTTTTGAGT | CTGCCGCCTG | CCCCGGTTGG | 360 |
| TTCCTCTGCA | CAGCGATGGA | AGCTGACCAG | CCCGTCAGCC | 400 |
| TCACCAATAT | GCCTGACGAA | GGCGTCATGG | TCACCAAATT | 440 |
| CTACTTCCAG | GAGGACGAGT | AAGTACTTGC | TAAAATGTAC | 480 |
| CCTAGGCCTC | CCGGGCTCGA | GTAAGCTTAT | GCAT | 514 |

FIGURE 39

```
ATGGCACCTG TACGATCACT GAACTGCACG CTCCGGGACT    40
CACAGCAAAA AAGCTTGGTG ATGTCTGGTC CATATGAACT    80
GAAAGCTCTC CACCTCCAGG GACAGGATAT GGAGCAACAA   120
GTGGTGTTCT CCATGTCCTT TGTACAAGGA GAAGAAAGTA   160
ATGACAAAAT ACCTGTGGCC TTGGGCCTCA AGGAAAAGAA   200
TCTGTACCTG TCCTGCGTGT TGAAAGATGA TAAGCCCACT   240
CTACAGCTGG AGAGTGTAGA TCCCAAAAAT TACCCAAAGA   280
AGAAGATGGA AAAGCGATTT GTCTTCAACA AGATAGAAAT   320
CAATAACAAG CTGGAATTTG AGTCTGCCCA GTTCCCCAAC   360
TGGTACATCA GCACCTCTCA AGCAGAAAAC ATGCCCGTCT   400
TCCTGGGAGG GACCAAAGGC GGCCAGGATA TAACTGACTT   440
CACCATGCAA TTTGTGTCTT CCGACCGCGG TGGCATGCAG   480
ATTTTCGTCA AGACTTTGAC CGGTAAAACC ATAACATTGG   520
AAGTTGAATC TTCCGATACC ATCGACAACG TTAAGTCGAA   560
AATTCAAGAC AAGGAAGGTA TCCCTCCAGA TCAACAAAGA   600
TTGATCTTTG CCGGTAAGCA GCTAGAAGAC GGTAGAACGC   640
TGTCTGATTA CAACATTCAG AAGGAGTCCA CCTTACATCT   680
TGTGCTAAGG CTCCGCGGTG GTGGTCCGGA AACCCTGTGC   720
GGTGCTGAAC TGGTTGACGC TCTGCAGTTC GTTTGCGGTG   760
ACCGTGGTTT CTACTTCAAC AAACCGACCG GTTACGGTTC   800
CTCCTCCCGT CGTGCTCCGC AGACCGGTAT CGTTGACGAA   840
TGCTGCTTCC GGTCCTGCGA CCTGCGTCGT CTGGAAATGT   880
ACTGCGCTCC GCTGAAACCG CTAAATCCG CTTAA         915
```

FIGURE 40

```
ATGGCGCAGT ATGAAGATGG TAAACAGTAC ACTACCCTGG    40
AAAAACCGGT AGCTGGCGCG CCTTCTGGTT CTTTCATGGG    80
TGGTGACCTG GGCAAAGATC TGACTCAGGC ATGGGCTGTG   120
GCGATGGCGC TGGGCGTGGA AGACAAAGTG ACTGTTCCGC   160
TGTTTGAAGG CGTACAGAAA ACCAGACCA TTCGTTCTGC    200
TTCTGATATC CGCGATGTAT TTATCAACGC AGGTATTAAA   240
GGTGAAGAGT ACGACGCGGC GTGGAACAGC TTCGTGGTGA   280
AATCTCTGGT CGCTCAGCAG GAAAAAGCTG CAGCTGACGT   320
GCAATTGCGT GGCGTTCCGG CGATGTTTGT TAACGGTAAA   360
TATCAGCTGA ATCCGCAGGG TATGGATACC AGCAATATGG   400
ATGTTTTTGT TCAGCAGTAT GCTGATACAG TGAAATATCT   440
GTCCGAGAAA AAACATCATC ACCATCATCA CAGCATGCCC   480
GGCAAGCAGC TAGAAGACGG TAGAACGCTG TCTGATTACA   520
ACATTCAGAA GGAGTCCACC TTACATCTTG TGCTAAGGCT   560
CCGCGGTGGT GGTCCGGAAA CCCTGTGCGG TGCTGAACTG   600
GTTGACGCTC TTCAGTTCGT TTGCGGTGAC CGTGGTTTCT   640
ACTTCAACAA ACCGACCGGT TACGGTTCCT CCTCCCGTCG   680
TGCTCCGCAG ACCGGTATCG TTGACGAATG CTGCTTCCGG   720
TCCTGCGACC TGCGTCGTCT GGAAATGTAC TGCGCTCCGC   760
TGAAACCGGC TAAATCCGCT TAA                     783
```

FIGURE 41

```
ATGGCGCAGT ATGAAGATGG TAAACAGTAC ACTACCCTGG    40
AAAAACCGGT AGCTGGCGCG CCTTCTGGTT CTTTCATGGG    80
TGGTGACCTG GGCAAAGATC TGACTCAGGC ATGGGCTGTG   120
GCGATGGCGC TGGGCGTGGA AGACAAAGTG ACTGTTCCGC   160
TGTTTGAAGG CGTACAGAAA ACCCAGACCA TTCGTTCTGC   200
TTCTGATATC CGCGATGTAT TTATCAACGC AGGTATTAAA   240
GGTGAAGAGT ACGACGCGGC GTGGAACAGC TTCGTGGTGA   280
AATCTCTGGT CGCTCAGCAG GAAAAAGCTG CAGCTGACGT   320
GCAATTGCGT GGCGTTCCGG CGATGTTTGT TAACGGTAAA   360
TATCAGCTGA ATCCGCAGGG TATGGATACC AGCAATATGG   400
ATGTTTTTGT TCAGCAGTAT GCTGATACAG TGAAATATCT   440
GTCCGAGAAA AAACATCATC ACCATCATCA CAGCATGCAG   480
ATTTTCGTCA AGACTTTGAC CGGTAAAACC ATAACATTGG   520
AAGTTGAACC TTCCGATACC ATCGAGAACG TTAAGGCGAA   560
AATTCAAGAC AAGGAAGGTA TCCCTCCAGA TCAACAAAGA   600
TTGATCTTTG CCGGCAAGCA GCTAGAAGAC GGTAGAACGC   640
TGTCTGATTA CAACATTCAG AAGGAGTCCA CCTTACATCT   680
TGTGCTAAGG CTCCGCGGTG GTGGTCCGGA AACCCTGTGC   720
GGTGCTGAAC TGGTTGACGC TCTTCAGTTC GTTTGCGGTG   760
ACCGTGGTTT CTACTTCAAC AAACCGACCG GTTACGGTTC   800
CTCCTCCCGT CGTGCTCCGC AGACCGGTAT CGTTGACGAA   840
TGCTGCTTCC GGTCCTGCGA CCTGCGTCGT CTGGAAATGT   880
ACTGCGCTCC GCTGAAACCG GCTAAATCCG CTTAA        915
```

FIGURE 42

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
        ( A ) LENGTH: 142 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Ala Gln Tyr Glu Asp Gly Lys Gln Tyr Thr Thr Leu Glu Lys Pro Val
 1               5                  10                  15

Ala Gly Ala Pro Phe Glu Glu Val Leu His Ile Ser Asp Asn Val Lys
            20                  25                  30

Lys Lys Leu Pro Glu Gly Val Lys Met Thr Lys Tyr His Val Asn Phe
         35                  40                  45

Met Gly Gly Asp Leu Gly Lys Asp Leu Thr Gln Ala Trp Ala Val Ala
     50                  55                  60

Met Ala Leu Gly Val Glu Asp Lys Val Thr Val Pro Leu Phe Glu Gly
 65                  70                  75                  80

Val Gln Lys Thr Gln Thr Ile Arg Ser Ala Ser Asp Ile Arg Asp Val
                 85                  90                  95

Phe Ile Asn Ala Gly Ile Lys Gly Glu Glu Tyr Asp Ala Ala Lys Tyr
            100                 105                 110

Gln Leu Asn Pro Gln Gly Met Asp Thr Ser Asn Met Asp Val Phe Val
         115                 120                 125

Gln Gln Tyr Ala Asp Thr Val Lys Tyr Leu Ser Glu Lys Lys
     130                 135                 140
```

( 2 ) INFORMATION FOR SEQ ID NO:2:

( i ) SEQUENCE CHARACTERISTICS:
        ( A ) LENGTH: 153 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Ala Pro Val Arg Ser Leu Asn Cys Thr Leu Arg Asp Ser Gln Gln Lys
 1               5                  10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
         35                  40                  45

Gly Glu Glu Ser Asn Asp Lys Ile Pro Val Ala Leu Gly Leu Lys Glu
     50                  55                  60

Lys Asn Leu Tyr Leu Ser Cys Val Leu Lys Asp Asp Lys Pro Thr Leu
 65                  70                  75                  80

Gln Leu Glu Ser Val Asp Pro Lys Asn Tyr Pro Lys Lys Lys Met Glu
                 85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
         115                 120                 125

Asn Met Pro Val Phe Leu Gly Gly Thr Lys Gly Gly Gln Asp Ile Thr
     130                 135                 140

Asp Phe Thr Met Gln Phe Val Ser Ser
 145                 150
```

( 2 ) INFORMATION FOR SEQ ID NO:3:

( i ) SEQUENCE CHARACTERISTICS:
      ( A ) LENGTH: 153 amino acids
      ( B ) TYPE: amino acid
      ( C ) STRANDEDNESS: single
      ( D ) TOPOLOGY: linear ( x i ) SEQUENCE DESCRIPTION: SEQ ID NO:3:

```
Ala Pro Phe Ser Phe Leu Ser Asn Val Lys Tyr Asn Phe Met Arg Ile
 1               5                  10                  15

Ile Lys Tyr Glu Phe Ile Leu Asn Asp Ala Ile Arg Ala Asn Asp Gln
             20                  25                  30

Tyr Leu Thr Ala Ala Ala Leu His Asn Leu Asp Glu Ala Val Lys Phe
         35              40                  45

Asp Met Gly Ala Tyr Lys Ser Ser Lys Asp Asp Ala Lys Ile Thr Val
     50              55                  60

Ile Leu Arg Ile Ser Lys Thr Gln Leu Tyr Val Thr Ala Gln Asp Glu
65              70                  75                  80

Asp Gln Pro Val Leu Leu Lys Glu Met Pro Glu Ile Pro Lys Thr Ile
                 85                  90                  95

Thr Gly Ser Glu Thr Asn Leu Leu Phe Phe Trp Glu Thr His Gly Thr
             100                 105                 110

Lys Asn Tyr Phe Thr Ser Val Ala His Pro Asn Leu Phe Ile Ala Thr
         115                 120                 125

Lys Gln Asp Tyr Trp Val Cys Leu Ala Gly Gly Pro Ser Ile Thr
    130                 135                 140

Asp Phe Gln Ile Leu Glu Asn Gln Ala
145                 150
```

( 2 ) INFORMATION FOR SEQ ID NO:4:

( i ) SEQUENCE CHARACTERISTICS:
      ( A ) LENGTH: 132 amino acids
      ( B ) TYPE: amino acid
      ( C ) STRANDEDNESS: single
      ( D ) TOPOLOGY: linear ( x i ) SEQUENCE DESCRIPTION: SEQ ID NO:4:

```
Gly His Phe Lys Asp Pro Lys Arg Leu Tyr Cys Lys Asn Gly Gly Phe
 1               5                  10                  15

Phe Leu Arg Ile His Pro Asp Gly Arg Val Asp Gly Val Arg Glu Lys
             20                  25                  30

Ser Asp Pro His Ile Lys Leu Gln Leu Gln Ala Glu Glu Arg Gly Val
         35                  40                  45

Val Ser Ile Lys Gly Val Cys Ala Asn Arg Tyr Leu Ala Met Lys Glu
     50              55                  60

Asp Gly Arg Leu Leu Ala Ser Lys Cys Val Thr Asp Glu Cys Phe Phe
65              70                  75                  80

Phe Glu Arg Leu Glu Ser Asn Asn Tyr Asn Thr Tyr Arg Ser Arg Lys
                 85                  90                  95

Tyr Thr Ser Trp Tyr Val Ala Leu Lys Arg Thr Gly Gln Tyr Lys Leu
             100                 105                 110

Gly Ser Lys Thr Gly Pro Gly Gln Lys Ala Ile Leu Phe Leu Pro Met
         115                 120                 125

Ser Ala Lys Ser
    130
```

( 2 ) INFORMATION FOR SEQ ID NO:5:

( i ) SEQUENCE CHARACTERISTICS:
  ( A ) LENGTH: 134 amino acids
  ( B ) TYPE: amino acid
  ( C ) STRANDEDNESS: single
  ( D ) TOPOLOGY: linear ( x i ) SEQUENCE DESCRIPTION: SEQ ID NO:5:

```
Gly Asn Tyr Lys Lys Pro Lys Leu Leu Tyr Cys Ser Asn Gly Gly Tyr
 1               5                      10                  15

Phe Leu Arg Ile Leu Pro Asp Gly Thr Val Asp Gly Thr Lys Asp Arg
            20              25                      30

Ser Asp Gln His Ile Gln Leu Gln Leu Cys Ala Glu Ser Ile Gly Glu
        35                  40                  45

Val Tyr Ile Lys Ser Thr Glu Thr Gly Gln Phe Leu Ala Met Asp Thr
    50                  55                      60

Asp Gly Leu Leu Tyr Gly Ser Gln Thr Pro Asn Glu Glu Cys Leu Phe
65                  70                  75                    80

Leu Glu Arg Leu Glu Glu Asn His Tyr Asn Thr Tyr Ile Ser Lys Lys
                85                  90                  95

His Ala Glu Lys His Trp Phe Val Gly Leu Lys Lys Asn Gly Arg Ser
            100             105                 110

Lys Leu Gly Pro Arg Thr His Phe Gly Gln Lys Ala Ile Leu Phe Leu
        115                 120                 125

Pro Leu Pro Val Ser Ser
        130
```

( 2 ) INFORMATION FOR SEQ ID NO:6:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( x i ) SEQUENCE DESCRIPTION: SEQ ID NO:6:

```
Asp Arg Gly Gly
 1
```

( 2 ) INFORMATION FOR SEQ ID NO:7:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:7:

```
His His His His His His Ser
 1               5
```

( 2 ) INFORMATION FOR SEQ ID NO:8:

( i ) SEQUENCE CHARACTERISTICS:
    ( A ) LENGTH: 69 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

```
GGATCCCGTG GAGGATTAAA CCATGGATGC ATAAGCTTCG AATTCTGCCA GGCATGCAAG    60
CTCAGATCC                                                            69
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Gly  Pro  Glu  Thr  Leu  Xaa  Gly  Ala  Glu  Leu
1                  5                        10
```

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

```
Gly  Pro  Glu  Thr  Leu  Xaa  Gly  Ala
1                  5
```

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:11:

```
Asp  Arg  Gly  Asp  Pro  His  His  His  His  His  His  Glu
1                  5                        10
```

( 2 ) INFORMATION FOR SEQ ID NO:12:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

```
Asp  Pro  His  His  His  His  His  His  Glu
1                  5
```

( 2 ) INFORMATION FOR SEQ ID NO:13:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
GGTGGATCCG ATCGTGGAGG ATGATTAAAT GGCTGATGAC GCGGCAATTC AACAAAC          57
```

( 2 ) INFORMATION FOR SEQ ID NO:14:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
GGGAAGCTTA CTCGAGCATG CTACCACCAG ATTTACCGCT GGTCATTTTT TGG              53
```

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
ACCTGTGGTT ACTGCCACAA A                                              21
```

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
ACCGGTAGCG GTTCTGGTAA A                                              21
```

( 2 ) INFORMATION FOR SEQ ID NO:17:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
GCGCGCCTTC TGGTTCTTTC ATGGGTGGTG ACCTGGGCAA AGATCT                   46
```

( 2 ) INFORMATION FOR SEQ ID NO:18:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
CATCATCACC ATCATCACAG CATGCCCGGG CTCGAGTAAG CTTATGCAT                49
```

( 2 ) INFORMATION FOR SEQ ID NO:19:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
GCATGGGTTC TCTGAAACCT ATCTTTGACG CTCAGAAGAT TGAGTGGCGT CATAGCATGC    60

ACCGCGGTCT CGAG                                                      74
```

( 2 ) INFORMATION FOR SEQ ID NO:20:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
GGCGGGCATG CACGGTTCAA GTACTAAACC TTACAGAGGA                          40
```

( 2 ) INFORMATION FOR SEQ ID NO:21:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
GGGGAATTCA  TGCATTATAT  TGTTTTTTCT  TTACGACGAC  GATTCGAAAC  CCAGTTTTTG      60
A                                                                           61
```

( 2 ) INFORMATION FOR SEQ ID NO:22:

( i ) SEQUENCE CHARACTERISTICS:
        ( A ) LENGTH: 720 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
ATGAAAAAGA  TTTGGCTGGC  GCTGGCTGGT  TTAGTTTTAG  CGTTTAGCGC  ATCGGCGGCG      60
CAGTATGAAG  ATGGTAAACA  GTACACTACC  CTGGAAAAAC  CGGTAGCTGG  CGCGCCGCAA     120
GTGCTGGAGT  TTTTCTCTTT  CTTCTGCCCG  CACTGCTATC  AGTTTGAAGA  AGTTCTGCAT     180
ATTTCTGATA  ATGTGAAGAA  AAAACTGCCG  GAAGGCGTGA  AGATGACTAA  ATACCACGTC     240
AACTTCATGG  GTGGTGACCT  GGGCAAAGAT  CTGACTCAGG  CATGGGCTGT  GGCGATGGCG     300
CTGGGCGTGG  AAGACAAAGT  GACTGTTCCG  CTGTTTGAAG  GCGTACAGAA  AACCCAGACC     360
ATTCGTTCTG  CTTCTGATAT  CCGCGATGTA  TTTATCAACG  CAGGTATTAA  AGGTGAAGAG     420
TACGACGCGG  CGTGGAACAG  CTTCGTGGTG  AAATCTCTGG  TCGCTCAGCA  GGAAAAAGCT     480
GCAGCTGACG  TGCAATTGCG  TGGCGTTCCG  GCGATGTTTG  TTAACGGTAA  ATATCAGCTG     540
AATCCGCAGG  GTATGGATAC  CAGCAATATG  GATGTTTTTG  TTCAGCAGTA  TGCTGATACA     600
GTGAAATATC  TGTCCGAGAA  AAAACATCAT  CACCATCATC  ACAGCATGGG  TTCTCTGAAA     660
CCTATCTTTG  ACGCTCAGAA  GATTGAGTGG  CGTCATAGCA  TGCACCGCGG  TCTCGAGTAA     720
```

( 2 ) INFORMATION FOR SEQ ID NO:23:

( i ) SEQUENCE CHARACTERISTICS:
        ( A ) LENGTH: 666 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
ATGGCGCAGT  ATGAAGATGG  TAAACAGTAC  ACTACCCTGG  AAAAACCGGT  AGCTGGCGCG      60
CCGCAAGTGC  TGGAGTTTTT  CTCTTTCTTC  TGCCCGCACT  GCTATCAGTT  TGAAGAAGTT     120
CTGCATATTT  CTGATAATGT  GAAGAAAAAA  CTGCCGGAAG  GCGTGAAGAT  GACTAAATAC     180
CACGTCAACT  TCATGGGTGG  TGACCTGGGC  AAAGATCTGA  CTCAGGCATG  GGCTGTGGCG     240
ATGGCGCTGG  GCGTGGAAGA  CAAAGTGACT  GTTCCGCTGT  TTGAAGGCGT  ACAGAAAACC     300
CAGACCATTC  GTTCTGCTTC  TGATATCCGC  GATGTATTTA  TCAACGCAGG  TATTAAAGGT     360
GAAGAGTACG  ACGCGGCGTG  GAACAGCTTC  GTGGTGAAAT  CTCTGGTCGC  TCAGCAGGAA     420
AAAGCTGCAG  CTGACGTGCA  ATTGCGTGGC  GTTCCGGCGA  TGTTTGTTAA  CGGTAAATAT     480
CAGCTGAATC  CGCAGGGTAT  GGATACCAGC  AATATGGATG  TTTTGTTCA  GCAGTATGCT     540
```

| GATACAGTGA | AATATCTGTC | CGAGAAAAAA | CATCATCACC | ATCATCACAG | CATGGGTTCT | 600 |
| CTGAAACCTA | TCTTTGACGC | TCAGAAGATT | GAGTGGCGTC | ATAGCATGCA | CCGCGGTCTC | 660 |
| GAGTAA | | | | | | 666 |

( 2 ) INFORMATION FOR SEQ ID NO:24:

( i ) SEQUENCE CHARACTERISTICS:
        ( A ) LENGTH: 900 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

| ATGGCGCAGT | ATGAAGATGG | TAAACAGTAC | ACTACCCTGG | AAAAACCGGT | AGCTGGCGCG | 60 |
| CCGCAAGTGC | TGGAGTTTTT | CTCTTTCTTC | TGCCCGCACT | GCTATCAGTT | TGAAGAAGTT | 120 |
| CTGCATATTT | CTGATAATGT | GAAGAAAAAA | CTGCCGGAAG | GCGTGAAGAT | GACTAAATAC | 180 |
| CACGTCAACT | TCATGGGTGG | TGACCTGGGC | AAAGATCTGA | CTCAGGCATG | GGCTGTGGCG | 240 |
| ATGGCGCTGG | GCGTGGAAGA | CAAAGTGACT | GTTCCGCTGT | TGAAGGCGT | ACAGAAACC | 300 |
| CAGACCATTC | GTTCTGCTTC | TGATATCCGC | GATGTATTTA | TCAACGCAGG | TATTAAGGT | 360 |
| GAAGAGTACG | ACGCGGCGTG | GAACAGCTTC | GTGGTGAAAT | CTCTGGTCGC | TCAGCAGGAA | 420 |
| AAAGCTGCAG | CTGACGTGCA | ATTGCGTGGC | GTTCCGGCGA | TGTTTGTTAA | CGGTAAATAT | 480 |
| CAGCTGAATC | CGCAGGGTAT | GGATACCAGC | AATATGGATG | TTTTGTTCA | GCAGTATGCT | 540 |
| GATACAGTGA | AATATCTGTC | CGAGAAAAAA | CATCATCACC | ATCATCACAG | CATGCCCGGC | 600 |
| AAGCAGCTAG | AAGACGGTAG | AACGCTGTCT | GATTACAACA | TTCAGAAGGA | GTCCACCTTA | 660 |
| CATCTTGTGC | TAAGGCTCCG | CGGTGGTGGT | CCGGAAACCC | TGTGCGGTGC | TGAACTGGTT | 720 |
| GACGCTCTTC | AGTTCGTTTG | CGGTGACCGT | GGTTTCTACT | TCAACAAACC | GACCGGTTAC | 780 |
| GGTTCCTCCT | CCCGTCGTGC | TCCGCAGACC | GGTATCGTTG | ACGAATGCTG | CTTCCGGTCC | 840 |
| TGCGACCTGC | GTCGTCTGGA | AATGTACTGC | GCTCCGCTGA | AACCGGCTAA | ATCCGCTTAA | 900 |

( 2 ) INFORMATION FOR SEQ ID NO:25:

( i ) SEQUENCE CHARACTERISTICS:
        ( A ) LENGTH: 1032 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

| ATGGCGCAGT | ATGAAGATGG | TAAACAGTAC | ACTACCCTGG | AAAAACCGGT | AGCTGGCGCG | 60 |
| CCGCAAGTGC | TGGAGTTTTT | CTCTTTCTTC | TGCCCGCACT | GCTATCAGTT | TGAAGAAGTT | 120 |
| CTGCATATTT | CTGATAATGT | GAAGAAAAAA | CTGCCGGAAG | GCGTGAAGAT | GACTAAATAC | 180 |
| CACGTCAACT | TCATGGGTGG | TGACCTGGGC | AAAGATCTGA | CTCAGGCATG | GGCTGTGGCG | 240 |
| ATGGCGCTGG | GCGTGGAAGA | CAAAGTGACT | GTTCCGCTGT | TGAAGGCGT | ACAGAAACC | 300 |
| CAGACCATTC | GTTCTGCTTC | TGATATCCGC | GATGTATTTA | TCAACGCAGG | TATTAAGGT | 360 |
| GAAGAGTACG | ACGCGGCGTG | GAACAGCTTC | GTGGTGAAAT | CTCTGGTCGC | TCAGCAGGAA | 420 |
| AAAGCTGCAG | CTGACGTGCA | ATTGCGTGGC | GTTCCGGCGA | TGTTTGTTAA | CGGTAAATAT | 480 |
| CAGCTGAATC | CGCAGGGTAT | GGATACCAGC | AATATGGATG | TTTTGTTCA | GCAGTATGCT | 540 |
| GATACAGTGA | AATATCTGTC | CGAGAAAAAA | CATCATCACC | ATCATCACAG | CATGCAGATT | 600 |
| TTCGTCAAGA | CTTTGACCGG | TAAAACCATA | ACATTGGAAG | TTGAACCTTC | CGATACCATC | 660 |

```
GAGAACGTTA  AGGCGAAAAT  TCAAGACAAG  GAAGGTATCC  CTCCAGATCA  ACAAAGATTG      720

ATCTTTGCCG  GCAAGCAGCT  AGAAGACGGT  AGAACGCTGT  CTGATTACAA  CATTCAGAAG      780

GAGTCCACCT  TACATCTTGT  GCTAAGGCTC  CGCGGTGGTG  GTCCGGAAAC  CCTGTGCGGT      840

GCTGAACTGG  TTGACGCTCT  TCAGTTCGTT  TGCGGTGACC  GTGGTTTCTA  CTTCAACAAA      900

CCGACCGGTT  ACGGTTCCTC  CTCCCGTCGT  GCTCCGCAGA  CCGGTATCGT  TGACGAATGC      960

TGCTTCCGGT  CCTGCGACCT  GCGTCGTCTG  GAAATGTACT  GCGCTCCGCT  GAAACCGGCT     1020

AAATCCGCTT  AA                                                             1032
```

( 2 ) INFORMATION FOR SEQ ID NO:26:

( i ) SEQUENCE CHARACTERISTICS:
        ( A ) LENGTH: 627 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
ATGAAAAAGA  TTTGGCTGGC  GCTGGCTGGT  TTAGTTTTAG  CGTTTAGCGC  ATCGGCGGCG       60

CAGTATGAAG  ATGGTAAACA  GTACACTACC  CTGGAAAAAC  CGGTAGCTGG  CGCGCCGCAA      120

GTGCTGGAGT  TTTTCTCTTT  CTTCTGCCCG  CACTGCTATC  AGTTTGAAGA  AGTTCTGCAT      180

ATTTCTGATA  ATGTGAAGAA  AAAACTGCCG  GAAGGCGTGA  AGATGACTAA  ATACCACGTC      240

AACTTCATGG  GTGGTGACCT  GGGCAAAGAT  CTGACTCAGG  CATGGGCTGT  GGCGATGGCG      300

CTGGGCGTGG  AAGACAAAGT  GACTGTTCCG  CTGTTTGAAG  GCGTACAGAA  AACCCAGACC      360

ATTCGTTCTG  CTTCTGATAT  CCGCGATGTA  TTTATCAACG  CAGGTATTAA  AGGTGAAGAG      420

TACGACGCGG  CGTGGAACAG  CTTCGTGGTG  AAATCTCTGG  TCGCTCAGCA  GGAAAAAGCT      480

GCAGCTGACG  TGCAATTGCG  TGGCGTTCCG  GCGATGTTTG  TTAACGGTAA  ATATCAGCTG      540

AATCCGCAGG  GTATGGATAC  CAGCAATATG  GATGTTTTTG  TTCAGCAGTA  TGCTGATACA      600

GTGAAATATC  TGTCCGAGAA  AAAATAA                                            627
```

( 2 ) INFORMATION FOR SEQ ID NO:27:

( i ) SEQUENCE CHARACTERISTICS:
        ( A ) LENGTH: 667 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

```
ATGGCTGATG  ACGCGGCAAT  TCAACAAACG  TTAGCCAAAA  TGGGCATCAA  AAGCAGCGAT       60

ATTCAGCCCG  CGCCTGTAGC  TGGCATGAAG  ACAGTTCTGA  CTAACAGCGG  CGTGTTGTAC      120

ATCACCGATG  ATGGTAAACA  TATCATTCAG  GGGCCAATGT  ATGACGTTAG  TGGCACGGCT      180

CCGGTCAATG  TCACCAATAA  GATGCTGTTA  AAGCAGTTGA  ATGCGCTTGA  AAAAGAGATG      240

ATCGTTTATA  AAGCGCCGCA  GGAAAAACAC  GTCATCACCG  TGTTTACTGA  TATTACCGGT      300

AGCGGTTCTG  GTAAACTGCA  TGAGCAAATG  GCAGACTACA  ACGCGCTGGG  GATCACCGTG      360

CGTTATCTTG  CTTTCCCGCG  CCAGGGGCTG  ACAGCGATG  CAGAGAAAGA  AATGAAAGCT      420

ATCTGGTGTG  CGAAAGATAA  AAACAAAGCG  TTTGATGATG  TGATGGCAGG  TAAAAGCGTC      480

GCACCAGCCA  GTTGCGACGT  GGATATTGCC  GACCATTACG  CACTTGGCGT  CCAGCTTGGC      540

GTTAGCGGTA  CTCCGGCAGT  TGTGCTGAGC  AATGGCACAC  TTGTTCCGGG  TTACCAGCCG      600

AAAGAGATGA  AGAATTCCT  CGACGAACAC  CAAAAAATGA  CCAGCGGTAA  ATCTGGTGGT      660
```

AGCATGC 667

( 2 ) INFORMATION FOR SEQ ID NO:28:

( i ) SEQUENCE CHARACTERISTICS:
        ( A ) LENGTH: 573 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

```
ATGGCGCAGT ATGAAGATGG TAAACAGTAC ACTACCCTGG AAAAACCGGT AGCTGGCGCG      60
CCGCAAGTGC TGGAGTTTTT CTCTTTCTTC TGCCCGCACT GCTATCAGTT TGAAGAAGTT     120
CTGCATATTT CTGATAATGT GAAGAAAAAA CTGCCGGAAG GCGTGAAGAT GACTAAATAC     180
CACGTCAACT TCATGGGTGG TGACCTGGGC AAAGATCTGA CTCAGGCATG GGCTGTGGCG     240
ATGGCGCTGG GCGTGGAAGA CAAAGTGACT GTTCCGCTGT TTGAAGGCGT ACAGAAAACC     300
CAGACCATTC GTTCTGCTTC TGATATCCGC GATGTATTTA TCAACGCAGG TATTAAAGGT     360
GAAGAGTACG ACGCGGCGTG GAACAGCTTC GTGGTGAAAT CTCTGGTCGC TCAGCAGGAA     420
AAAGCTGCAG CTGACGTGCA ATTGCGTGGC GTTCCGGCGA TGTTTGTTAA CGGTAAATAT     480
CAGCTGAATC CGCAGGGTAT GGATACCAGC AATATGGATG TTTTGTTCA GCAGTATGCT      540
GATACAGTGA AATATCTGTC CGAGAAAAAA TAA                                   573
```

( 2 ) INFORMATION FOR SEQ ID NO:29:

( i ) SEQUENCE CHARACTERISTICS:
        ( A ) LENGTH: 619 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

```
ATGGCGCAGT ATGAAGATGG TAAACAGTAC ACTACCCTGG AAAAACCGGT AGCTGGCGCG      60
CCGCAAGTGC TGGAGTTTTT CTCTTTCTTC TGCCCGCACT GCTATCAGTT TGAAGAAGTT     120
CTGCATATTT CTGATAATGT GAAGAAAAAA CTGCCGGAAG GCGTGAAGAT GACTAAATAC     180
CACGTCAACT TCATGGGTGG TGACCTGGGC AAAGATCTGA CTCAGGCATG GGCTGTGGCG     240
ATGGCGCTGG GCGTGGAAGA CAAAGTGACT GTTCCGCTGT TTGAAGGCGT ACAGAAAACC     300
CAGACCATTC GTTCTGCTTC TGATATCCGC GATGTATTTA TCAACGCAGG TATTAAAGGT     360
GAAGAGTACG ACGCGGCGTG GAACAGCTTC GTGGTGAAAT CTCTGGTCGC TCAGCAGGAA     420
AAAGCTGCAG CTGACGTGCA ATTGCGTGGC GTTCCGGCGA TGTTTGTTAA CGGTAAATAT     480
CAGCTGAATC CGCAGGGTAT GGATACCAGC AATATGGATG TTTTGTTCA GCAGTATGCT      540
GATACAGTGA AATATCTGTC CGAGAAAAAA CATCATCACC ATCATCACAG CATGCCCGGG     600
CTCGAGTAAG CTTATGCAT                                                   619
```

( 2 ) INFORMATION FOR SEQ ID NO:30:

( i ) SEQUENCE CHARACTERISTICS:
        ( A ) LENGTH: 456 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

```
ATGGCGCAGT ATGAAGATGG TAAACAGTAC ACTACCCTGG AAAAACCGGT AGCTGGCGCG      60
CCTTCTGGTT CTTTCATGGG TGGTGACCTG GGCAAAGATC TGACTCAGGC ATGGGCTGTG     120
```

| GCGATGGCGC | TGGGCGTGGA | AGACAAAGTG | ACTGTTCCGC | TGTTTGAAGG | CGTACAGAAA | 180 |
| ACCCAGACCA | TTCGTTCTGC | TTCTGATATC | CGCGATGTAT | TTATCAACGC | AGGTATTAAA | 240 |
| GGTGAAGAGT | ACGACGCGGC | GTGGAACAGC | TTCGTGGTGA | AATCTCTGGT | CGCTCAGCAG | 300 |
| GAAAAAGCTG | CAGCTGACGT | GCAATTGCGT | GGCGTTCCGG | CGATGTTTGT | TAACGGTAAA | 360 |
| TATCAGCTGA | ATCCGCAGGG | TATGGATACC | AGCAATATGG | ATGTTTTTGT | TCAGCAGTAT | 420 |
| GCTGATACAG | TGAAATATCT | GTCCGAGAAA | AAATAA | | | 456 |

( 2 ) INFORMATION FOR SEQ ID NO:31:

( i ) SEQUENCE CHARACTERISTICS:
        ( A ) LENGTH: 1032 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

| ATGGCGCAGT | ATGAAGATGG | TAAACAGTAC | ACTACCCTGG | AAAAACCGGT | AGCTGGCGCG | 60 |
| CCGCAAGTGC | TGGAGTTTTT | CTCTTTCTTC | TGCCCGCACT | GCTATCAGTT | TGAAGAAGTT | 120 |
| CTGCATATTT | CTGATAATGT | GAAGAAAAAA | CTGCCGGAAG | CGTGAAGAT | GACTAAATAC | 180 |
| CACGTCAACT | TCATGGGTGG | TGACCTGGGC | AAAGATCTGA | CTCAGGCATG | GGCTGTGGCG | 240 |
| ATGGCGCTGG | GCGTGGAAGA | CAAAGTGACT | GTTCCGCTGT | TGAAGGCGT | ACAGAAACC | 300 |
| CAGACCATTC | GTTCTGCTTC | TGATATCCGC | GATGTATTTA | TCAACGCAGG | TATTAAAGGT | 360 |
| GAAGAGTACG | ACGCGGCGTG | GAACAGCTTC | GTGGTGAAAT | CTCTGGTCGC | TCAGCAGGAA | 420 |
| AAAGCTGCAG | CTGACGTGCA | ATTGCGTGGC | GTTCCGGCGA | TGTTTGTTAA | CGGTAAATAT | 480 |
| CAGCTGAATC | CGCAGGGTAT | GGATACCAGC | AATATGGATG | TTTTGTTCA | GCAGTATGCT | 540 |
| GATACAGTGA | AATATCTGTC | CGAGAAAAAA | CATCATCACC | ATCATCACAG | CATGCAGATT | 600 |
| TCGTCAAGA | CTTTGACCGG | TAAAACCATA | ACATTGGAAG | TTGAATCTTC | CGATACCATC | 660 |
| GACAACGTTA | AGTCGAAAAT | TCAAGACAAG | GAAGGTATCC | CTCCAGATCA | ACAAAGATTG | 720 |
| ATCTTTGCCG | GTAAGCAGCT | AGAAGACGGT | AGAACGCTGT | CTGATTACAA | CATTCAGAAG | 780 |
| GAGTCCACCT | TACATCTTGT | GCTAAGGCTC | CGCGGTGGTG | GTCCGGAAAC | CCTGTGCGGT | 840 |
| GCTGAACTGG | TTGACGCTCT | GCAGTTCGTT | TGCGGTGACC | GTGGTTTCTA | CTTCAACAAA | 900 |
| CCGACCGGTT | ACGGTTCCTC | CTCCCGTCGT | GCTCCGCAGA | CCGGTATCGT | TGACGAATGC | 960 |
| TGCTTCCGGT | CCTGCGACCT | GCGTCGTCTG | GAAATGTACT | GCGCTCCGCT | GAAACCGGCT | 1020 |
| AAATCCGCTT | AA | | | | | 1032 |

( 2 ) INFORMATION FOR SEQ ID NO:32:

( i ) SEQUENCE CHARACTERISTICS:
        ( A ) LENGTH: 1104 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

| ATGGCTGATG | ACGCGGCAAT | TCAACAAACG | TTAGCCAAAA | TGGGCATCAA | AAGCAGCGAT | 60 |
| ATTCAGCCCG | CGCCTGTAGC | TGGCATGAAG | ACAGTTCTGA | CTAACAGCGG | CGTGTTGTAC | 120 |
| ATCACCGATG | ATGGTAAACA | TATCATTCAG | GGGCCAATGT | ATGACGTTAG | TGGCACGGCT | 180 |
| CCGGTCAATG | TCACCAATAA | GATGCTGTTA | AAGCAGTTGA | ATGCGCTTGA | AAAAGAGATG | 240 |
| ATCGTTTATA | AAGCGCCGCA | GGAAAAACAC | GTCATCACCG | TGTTTACTGA | TATTACCTGT | 300 |

```
GGTTACTGCC  ACAAACTGCA  TGAGCAAATG  GCAGACTACA  ACGCGCTGGG  GATCACCGTG       360

CGTTATCTTG  CTTTCCCGCG  CCAGGGGCTG  GACAGCGATG  CAGAGAAAGA  AATGAAAGCT       420

ATCTGGTGTG  CGAAAGATAA  AAACAAAGCG  TTTGATGATG  TGATGGCAGG  TAAAAGCGTC       480

GCACCAGCCA  GTTGCGACGT  GGATATTGCC  GACCATTACG  CACTTGGCGT  CCAGCTTGGC       540

GTTAGCGGTA  CTCCGGCAGT  TGTGCTGAGC  AATGGCACAC  TTGTTCCGGG  TTACCAGCCG       600

AAAGAGATGA  AGAATTCCT   CGACGAACAC  CAAAAAATGA  CCAGCGGTAA  ATCTGGTGGT       660

AGCATGCAGA  TTTTCGTCAA  GACTTTGACC  GGTAAAACCA  TAACATTGGA  AGTTGAACCT       720

TCCGATACCA  TCGAGAACGT  TAAGGCGAAA  ATTCAAGACA  AGGAAGGTAT  CCCTCCAGAT       780

CAACAAAGAT  TGATCTTTGC  CGGCAAGCAG  CTAGAAGACG  GTAGAACGCT  GTCTGATTAC       840

AACATTCAGA  AGGAGTCCAC  CTTACATCTT  GTGCTAAGGC  TCCGCGGTGG  TGGTCCGGAA       900

ACCCTGTGCG  GTGCTGAACT  GGTTGACGCT  CTTCAGTTCG  TTTGCGGTGA  CCGTGGTTTC       960

TACTTCAACA  AACCGACCGG  TTACGGTTCC  TCCTCCCGTC  GTGCTCCGCA  GACCGGTATC      1020

GTTGACGAAT  GCTGCTTCCG  GTCCTGCGAC  CTGCGTCGTC  TGGAAATGTA  CTGCGCTCCG      1080

CTGAAACCGG  CTAAATCCGC  TTAA                                                1104
```

( 2 ) INFORMATION FOR SEQ ID NO:33:

( i ) SEQUENCE CHARACTERISTICS:
        ( A ) LENGTH: 891 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

```
ATGGCTGATG  ACGCGGCAAT  TCAACAAACG  TTAGCCAAAA  TGGGCATCAA  AAGCAGCGAT        60

ATTCAGCCCG  CGCCTGTAGC  TGGCATGAAG  ACAGTTCTGA  CTAACAGCGG  CGTGTTGTAC       120

ATCACCGATG  ATGGTAAACA  TATCATTCAG  GGGCCAATGT  ATGACGTTAG  TGGCACGGCT       180

CCGGTCAATG  TCACCAATAA  GATGCTGTTA  AAGCAGTTGA  ATGCGCTTGA  AAAAGAGATG       240

ATCGTTTATA  AAGCGCCGCA  GGAAAAACAC  GTCATCACCG  TGTTTACTGA  TATTACCGGT       300

AGCGGTTCTG  GTAAACTGCA  TGAGCAAATG  GCAGACTACA  ACGCGCTGGG  GATCACCGTG       360

CGTTATCTTG  CTTTCCCGCG  CCAGGGGCTG  GACAGCGATG  CAGAGAAAGA  AATGAAAGCT       420

ATCTGGTGTG  CGAAAGATAA  AAACAAAGCG  TTTGATGATG  TGATGGCAGG  TAAAAGCGTC       480

GCACCAGCCA  GTTGCGACGT  GGATATTGCC  GACCATTACG  CACTTGGCGT  CCAGCTTGGC       540

GTTAGCGGTA  CTCCGGCAGT  TGTGCTGAGC  AATGGCACAC  TTGTTCCGGG  TTACCAGCCG       600

AAAGAGATGA  AGAATTCCT   CGACGAACAC  CAAAAAATGA  CCAGCGGTAA  ATCTGGTGGT       660

AGCATGCACC  GCGGTGGTGG  TCCGGAAACC  CTGTGCGGTG  CTGAACTGGT  TGACGCTCTT       720

CAGTTCGTTT  GCGGTGACCG  TGGTTTCTAC  TTCAACAAAC  CGACCGGTTA  CGGTTCCTCC       780

TCCCGTCGTG  CTCCGCAGAC  CGGTATCGTT  GACGAATGCT  GCTTCCGGTC  CTGCGACCTG       840

CGTCGTCTGG  AAATGTACTG  CGCTCCGCTG  AAACCGGCTA  AATCCGCTTA  A                891
```

( 2 ) INFORMATION FOR SEQ ID NO:34:

( i ) SEQUENCE CHARACTERISTICS:
        ( A ) LENGTH: 891 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

```
ATGGCTGATG ACGCGGCAAT TCAACAAACG TTAGCCAAAA TGGGCATCAA AAGCAGCGAT        60
ATTCAGCCCG CGCCTGTAGC TGGCATGAAG ACAGTTCTGA CTAACAGCGG CGTGTTGTAC       120
ATCACCGATG ATGGTAAACA TATCATTCAG GGGCCAATGT ATGACGTTAG TGGCACGGCT       180
CCGGTCAATG TCACCAATAA GATGCTGTTA AAGCAGTTGA ATGCGCTTGA AAAAGAGATG       240
ATCGTTTATA AAGCGCCGCA GGAAAAACAC GTCATCACCG TGTTTACTGA TATTACCTGT       300
GGTTACTGCC ACAAACTGCA TGAGCAAATG GCAGACTACA ACGCGCTGGG GATCACCGTG       360
CGTTATCTTG CTTTCCCGCG CCAGGGGCTG GACAGCGATG CAGAGAAAGA AATGAAAGCT       420
ATCTGGTGTG CGAAAGATAA AAACAAAGCG TTTGATGATG TGATGGCAGG TAAAAGCGTC       480
GCACCAGCCA GTTGCGACGT GGATATTGCC GACCATTACG CACTTGGCGT CCAGCTTGGC       540
GTTAGCGGTA CTCCGGCAGT TGTGCTGAGC AATGGCACAC TTGTTCCGGG TTACCAGCCG       600
AAAGAGATGA AGAATTCCT CGACGAACAC CAAAAAATGA CCAGCGGTAA ATCTGGTGGT        660
AGCATGCACC GCGGTGGTGG TCCGGAAACC CTGTGCGGTG CTGAACTGGT TGACGCTCTT       720
CAGTTCGTTT GCGGTGACCG TGGTTTCTAC TTCAACAAAC CGACCGGTTA CGGTTCCTCC       780
TCCCGTCGTG CTCCGCAGAC CGGTATCGTT GACGAATGCT GCTTCCGGTC CTGCGACCTG       840
CGTCGTCTGG AAATGTACTG CGCTCCGCTG AAACCGGCTA AATCCGCTTA A                891
```

(2) INFORMATION FOR SEQ ID NO:35:

(i) SEQUENCE CHARACTERISTICS:
  (A) LENGTH: 667 base pairs
  (B) TYPE: nucleic acid
  (C) STRANDEDNESS: single
  (D) TOPOLOGY: linear (xi) SEQUENCE DESCRIPTION: SEQ ID NO:35:

```
ATGGCTGATG ACGCGGCAAT TCAACAAACG TTAGCCAAAA TGGGCATCAA AAGCAGCGAT        60
ATTCAGCCCG CGCCTGTAGC TGGCATGAAG ACAGTTCTGA CTAACAGCGG CGTGTTGTAC       120
ATCACCGATG ATGGTAAACA TATCATTCAG GGGCCAATGT ATGACGTTAG TGGCACGGCT       180
CCGGTCAATG TCACCAATAA GATGCTGTTA AAGCAGTTGA ATGCGCTTGA AAAAGAGATG       240
ATCGTTTATA AAGCGCCGCA GGAAAAACAC GTCATCACCG TGTTTACTGA TATTACCTGT       300
GGTTACTGCC ACAAACTGCA TGAGCAAATG GCAGACTACA ACGCGCTGGG GATCACCGTG       360
CGTTATCTTG CTTTCCCGCG CCAGGGGCTG GACAGCGATG CAGAGAAAGA AATGAAAGCT       420
ATCTGGTGTG CGAAAGATAA AAACAAAGCG TTTGATGATG TGATGGCAGG TAAAAGCGTC       480
GCACCAGCCA GTTGCGACGT GGATATTGCC GACCATTACG CACTTGGCGT CCAGCTTGGC       540
GTTAGCGGTA CTCCGGCAGT TGTGCTGAGC AATGGCACAC TTGTTCCGGG TTACCAGCCG       600
AAAGAGATGA AGAATTCCT CGACGAACAC CAAAAAATGA CCAGCGGTAA ATCTGGTGGT        660
AGCATGC                                                                 667
```

(2) INFORMATION FOR SEQ ID NO:36:

(i) SEQUENCE CHARACTERISTICS:
  (A) LENGTH: 702 base pairs
  (B) TYPE: nucleic acid
  (C) STRANDEDNESS: single
  (D) TOPOLOGY: linear (xi) SEQUENCE DESCRIPTION: SEQ ID NO:36:

```
ATGGCACCTG TACGATCACT GAACTGCACG CTCCGGGACT CACAGCAAAA AAGCTTGGTG        60
ATGTCTGGTC CATATGAACT GAAAGCTCTC CACCTCCAGG GACAGGATAT GGAGCAACAA       120
```

```
GTGGTGTTCT  CCATGTCCTT  TGTACAAGGA  GAAGAAAGTA  ATGACAAAAT  ACCTGTGGCC        180

TTGGGCCTCA  AGGAAAAGAA  TCTGTACCTG  TCCTGCGTGT  TGAAAGATGA  TAAGCCCACT        240

CTACAGCTGG  AGAGTGTAGA  TCCCAAAAAT  TACCCAAAGA  AGAAGATGGA  AAAGCGATTT        300

GTCTTCAACA  AGATAGAAAT  CAATAACAAG  CTGGAATTTG  AGTCTGCCCA  GTTCCCCAAC        360

TGGTACATCA  GCACCTCTCA  AGCAGAAAAC  ATGCCCGTCT  TCCTGGGAGG  GACCAAAGGC        420

GGCCAGGATA  TAACTGACTT  CACCATGCAA  TTTGTGTCTT  CCGACCGCGG  TGGCATGCAC        480

CGCGGTGGTG  GTCCGGAAAC  CCTGTGCGGT  GCTGAACTGG  TTGACGCTCT  GCAGTTCGTT        540

TGCGGTGACC  GTGGTTTCTA  CTTCAACAAA  CCGACCGGTT  ACGGTTCCTC  CTCCCGTCGT        600

GCTCCGCAGA  CCGGTATCGT  TGACGAATGC  TGCTTCCGGT  CCTGCGACCT  GCGTCGTCTG        660

GAAATGTACT  GCGCTCCGCT  GAAACCGGCT  AAATCCGCTT  AA                           702
```

( 2 ) INFORMATION FOR SEQ ID NO:37:

( i ) SEQUENCE CHARACTERISTICS:
        ( A ) LENGTH: 465 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

```
ATGGCACCTG  TACGATCACT  GAACTGCACG  CTCCGGGACT  CACAGCAAAA  AAGCTTGGTG         60

ATGTCTGGTC  CATATGAACT  GAAAGCTCTC  CACCTCCAGG  GACAGGATAT  GGAGCAACAA        120

GTGGTGTTCT  CCATGTCCTT  TGTACAAGGA  GAAGAAAGTA  ATGACAAAAT  ACCTGTGGCC        180

TTGGGCCTCA  AGGAAAAGAA  TCTGTACCTG  TCCTGCGTGT  TGAAAGATGA  TAAGCCCACT        240

CTACAGCTGG  AGAGTGTAGA  TCCCAAAAAT  TACCCAAAGA  AGAAGATGGA  AAAGCGATTT        300

GTCTTCAACA  AGATAGAAAT  CAATAACAAG  CTGGAATTTG  AGTCTGCCCA  GTTCCCCAAC        360

TGGTACATCA  GCACCTCTCA  AGCAGAAAAC  ATGCCCGTCT  TCCTGGGAGG  GACCAAAGGC        420

GGCCAGGATA  TAACTGACTT  CACCATGCAA  TTTGTGTCTT  CCTAA                        465
```

( 2 ) INFORMATION FOR SEQ ID NO:38:

( i ) SEQUENCE CHARACTERISTICS:
        ( A ) LENGTH: 478 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

```
ATGGCACCTG  TACGATCACT  GAACTGCACG  CTCCGGGACT  CACAGCAAAA  AAGCTTGGTG         60

ATGTCTGGTC  CATATGAACT  GAAAGCTCTC  CACCTCCAGG  GACAGGATAT  GGAGCAACAA        120

GTGGTGTTCT  CCATGTCCTT  TGTACAAGGA  GAAGAAAGTA  ATGACAAAAT  ACCTGTGGCC        180

TTGGGCCTCA  AGGAAAAGAA  TCTGTACCTG  TCCTGCGTGT  TGAAAGATGA  TAAGCCCACT        240

CTACAGCTGG  AGAGTGTAGA  TCCCAAAAAT  TACCCAAAGA  AGAAGATGGA  AAAGCGATTT        300

GTCTTCAACA  AGATAGAAAT  CAATAACAAG  CTGGAATTTG  AGTCTGCCCA  GTTCCCCAAC        360

TGGTACATCA  GCACCTCTCA  AGCAGAAAAC  ATGCCCGTCT  TCCTGGGAGG  GACCAAAGGC        420

GGCCAGGATA  TAACTGACTT  CACCATGCAA  TTTGTGTCTT  CCGACCGCGG  TGGCATGC         478
```

( 2 ) INFORMATION FOR SEQ ID NO:39:

( i ) SEQUENCE CHARACTERISTICS:
        ( A ) LENGTH: 469 base pairs ( B ) TYPE: nucleic acid
( C ) STRANDEDNESS: single
( D ) TOPOLOGY: linear ( x i ) SEQUENCE DESCRIPTION: SEQ ID NO:39:

| | | | | | |
|---|---|---|---|---|---|
| ATGGCACCTG | TACGATCACT | GAACTGCACG | CTCGGGGACT | CACAGCAAAA | AAGCTTGGTG | 60 |
| ATGTCTGGTC | CATATGAACT | GAAAGCTCTC | CACCTCCAGG | GACAGGATAT | GGAGCAACAA | 120 |
| GTGGTGTTCT | CCATGTCCTT | TGTACAAGGA | GAAGAAAGTA | ATGACAAAAT | ACCTGTGGCC | 180 |
| TTGGGCCTCA | AGGAAAAGAA | TCTGTACCTG | TCCTGCGTGT | TGAAAGATGA | TAAGCCCACT | 240 |
| CTACAGCTGG | AGAGTGTAGA | TCCCAAAAAT | TACCCAAAGA | AGAAGATGGA | AAAGCGATTT | 300 |
| GTCTTCAACA | AGATAGAAAT | CAATAACAAG | CTGGAATTTG | AGTCTGCCCA | GTTCCCCAAC | 360 |
| TGGTACATCA | GCACCTCTCA | AGCAGAAAAC | ATGCCCGTCT | TCCTGGGAGG | GACCAAAGGC | 420 |
| GGCCAGGATA | TAACTGACTT | CACCATGCAA | TTTGTGTCTT | CCAGCATGC | | 469 |

( 2 ) INFORMATION FOR SEQ ID NO:40:

( i ) SEQUENCE CHARACTERISTICS:
( A ) LENGTH: 717 base pairs
( B ) TYPE: nucleic acid
( C ) STRANDEDNESS: single
( D ) TOPOLOGY: linear ( x i ) SEQUENCE DESCRIPTION: SEQ ID NO:40:

| | | | | | |
|---|---|---|---|---|---|
| ATGCGGCCGT | CTGGGAGAAA | ATCCAGCAAG | ATGCAAGCCT | TCAGAATCTG | GATGTTAAC | 60 |
| CAGAAGACCT | TCTATCTGAG | GAACAACCAA | CTAGTTGCTG | GATACTTGCA | AGGACCAAAT | 120 |
| GTCAATTTAG | AAGAAAAGAT | AGATGTGGTA | CCCATTGAGC | CTCATGCTCT | GTTCTTGGGA | 180 |
| ATCCATGGAG | GGAAGATGTG | CCTGTCCTGT | GTCAAGTCTG | GTGATGAGAC | CAGACTCCAG | 240 |
| CTGGAGGCAG | TTAACATCAC | TGACCTGAGC | GAGAACAGAA | AGCAGGACAA | GCGCTTCGCC | 300 |
| TTCATCCGCT | CAGACAGTGG | CCCCACCACC | AGTTTTGAGT | CTGCCGCCTG | CCCCGGTTGG | 360 |
| TTCCTCTGCA | CAGCGATGGA | AGCTGACCAG | CCCGTCAGCC | TCACCAATAT | GCCTGACGAA | 420 |
| GGCGTCATGG | TCACCAAATT | CTACTTCCAG | GAGGACGAGT | CTGGTTCTGG | TGACGATGAC | 480 |
| GATAAGAGCA | TGCACCGCGG | TGGTGGTCCG | GAAACCCTGT | GCGGTGCTGA | ACTGGTTGAC | 540 |
| GCTCTTCAGT | TCGTTTGCGG | TGACCGTGGT | TTCTACTTCA | ACAAACCGAC | CGGTTACGGT | 600 |
| TCCTCCTCCC | GTCGTGCTCC | GCAGACCGGT | ATCGTTGACG | AATGCTGCTT | CCGGTCCTGC | 660 |
| GACCTGCGTC | GTCTGGAAAT | GTACTGCGCT | CCGCTGAAAC | CGGCTAAATC | CGCTTAA | 717 |

( 2 ) INFORMATION FOR SEQ ID NO:41:

( i ) SEQUENCE CHARACTERISTICS:
( A ) LENGTH: 514 base pairs
( B ) TYPE: nucleic acid
( C ) STRANDEDNESS: single
( D ) TOPOLOGY: linear ( x i ) SEQUENCE DESCRIPTION: SEQ ID NO:41:

| | | | | | |
|---|---|---|---|---|---|
| ATGCGGCCGT | CTGGGAGAAA | ATCCAGCAAG | ATGCAAGCCT | TCAGAATCTG | GATGTTAAC | 60 |
| CAGAAGACCT | TCTATCTGAG | GAACAACCAA | CTAGTTGCTG | GATACTTGCA | AGGACCAAAT | 120 |
| GTCAATTTAG | AAGAAAAGAT | AGATGTGGTA | CCCATTGAGC | CTCATGCTCT | GTTCTTGGGA | 180 |
| ATCCATGGAG | GGAAGATGTG | CCTGTCCTGT | GTCAAGTCTG | GTGATGAGAC | CAGACTCCAG | 240 |
| CTGGAGGCAG | TTAACATCAC | TGACCTGAGC | GAGAACAGAA | AGCAGGACAA | GCGCTTCGCC | 300 |
| TTCATCCGCT | CAGACAGTGG | CCCCACCACC | AGTTTTGAGT | CTGCCGCCTG | CCCCGGTTGG | 360 |

| TTCCTCTGCA | CAGCGATGGA | AGCTGACCAG | CCCGTCAGCC | TCACCAATAT | GCCTGACGAA | 420 |
| GGCGTCATGG | TCACCAAATT | CTACTTCCAG | GAGGACGAGT | AAGTACTTGC | TAAAATGTAC | 480 |
| CCTAGGCCTC | CCGGGCTCGA | GTAAGCTTAT | GCAT | | | 514 |

( 2 ) INFORMATION FOR SEQ ID NO:42:

( i ) SEQUENCE CHARACTERISTICS:
        ( A ) LENGTH: 915 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

| ATGGCACCTG | TACGATCACT | GAACTGCACG | CTCCGGGACT | CACAGCAAAA | AAGCTTGGTG | 60 |
| ATGTCTGGTC | CATATGAACT | GAAAGCTCTC | CACCTCCAGG | GACAGGATAT | GGAGCAACAA | 120 |
| GTGGTGTTCT | CCATGTCCTT | TGTACAAGGA | GAAGAAAGTA | ATGACAAAAT | ACCTGTGGCC | 180 |
| TTGGGCCTCA | AGGAAAAGAA | TCTGTACCTG | TCCTGCGTGT | TGAAAGATGA | TAAGCCCACT | 240 |
| CTACAGCTGG | AGAGTGTAGA | TCCCAAAAAT | TACCCAAAGA | AGAAGATGGA | AAAGCGATTT | 300 |
| GTCTTCAACA | AGATAGAAAT | CAATAACAAG | CTGGAATTTG | AGTCTGCCCA | GTTCCCCAAC | 360 |
| TGGTACATCA | GCACCTCTCA | AGCAGAAAAC | ATGCCCGTCT | TCCTGGGAGG | GACCAAAGGC | 420 |
| GGCCAGGATA | TAACTGACTT | CACCATGCAA | TTTGTGTCTT | CCGACCGCGG | TGGCATGCAG | 480 |
| ATTTTCGTCA | AGACTTTGAC | CGGTAAAACC | ATAACATTGG | AAGTTGAATC | TTCCGATACC | 540 |
| ATCGACAACG | TTAAGTCGAA | AATTCAAGAC | AAGGAAGGTA | TCCCTCCAGA | TCAACAAAGA | 600 |
| TTGATCTTTG | CCGGTAAGCA | GCTAGAAGAC | GGTAGAACGC | TGTCTGATTA | CAACATTCAG | 660 |
| AAGGAGTCCA | CCTTACATCT | TGTGCTAAGG | CTCCGCGGTG | GTGGTCCGGA | AACCCTGTGC | 720 |
| GGTGCTGAAC | TGGTTGACGC | TCTGCAGTTC | GTTTGCGGTG | ACCGTGGTTT | CTACTTCAAC | 780 |
| AAACCGACCG | GTTACGGTTC | CTCCTCCCGT | CGTGCTCCGC | AGACCGGTAT | CGTTGACGAA | 840 |
| TGCTGCTTCC | GGTCCTGCGA | CCTGCGTCGT | CTGGAAATGT | ACTGCGCTCC | GCTGAAACCG | 900 |
| GCTAAATCCG | CTTAA | | | | | 915 |

( 2 ) INFORMATION FOR SEQ ID NO:43:

( i ) SEQUENCE CHARACTERISTICS:
        ( A ) LENGTH: 783 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

| ATGGCGCAGT | ATGAAGATGG | TAAACAGTAC | ACTACCCTGG | AAAAACCGGT | AGCTGGCGCG | 60 |
| CCTTCTGGTT | CTTTCATGGG | TGGTGACCTG | GGCAAAGATC | TGACTCAGGC | ATGGGCTGTG | 120 |
| GCGATGGCGC | TGGGCGTGGA | AGACAAAGTG | ACTGTTCCGC | TGTTTGAAGG | CGTACAGAAA | 180 |
| ACCCAGACCA | TTCGTTCTGC | TTCTGATATC | CGCGATGTAT | TTATCAACGC | AGGTATTAAA | 240 |
| GGTGAAGAGT | ACGACGCGGC | GTGGAACAGC | TTCGTGGTGA | ATCTCTGGT | CGCTCAGCAG | 300 |
| GAAAAAGCTG | CAGCTGACGT | GCAATTGCGT | GGCGTTCCGG | CGATGTTTGT | TAACGGTAAA | 360 |
| TATCAGCTGA | ATCCGCAGGG | TATGGATACC | AGCAATATGG | ATGTTTTTGT | TCAGCAGTAT | 420 |
| GCTGATACAG | TGAAATATCT | GTCCGAGAAA | AAACATCATC | ACCATCATCA | CAGCATGCCC | 480 |
| GGCAAGCAGC | TAGAAGACGG | TAGAACGCTG | TCTGATTACA | ACATTCAGAA | GGAGTCCACC | 540 |
| TTACATCTTG | TGCTAAGGCT | CCGCGGTGGT | GGTCCGGAAA | CCCTGTGCGG | TGCTGAACTG | 600 |

-continued

```
GTTGACGCTC  TTCAGTTCGT  TTGCGGTGAC  CGTGGTTTCT  ACTTCAACAA  ACCGACCGGT    660

TACGGTTCCT  CCTCCCGTCG  TGCTCCGCAG  ACCGGTATCG  TTGACGAATG  CTGCTTCCGG    720

TCCTGCGACC  TGCGTCGTCT  GGAAATGTAC  TGCGCTCCGC  TGAAACCGGC  TAAATCCGCT    780

TAA                                                                       783
```

( 2 ) INFORMATION FOR SEQ ID NO:44:

( i ) SEQUENCE CHARACTERISTICS:
        ( A ) LENGTH: 915 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

```
ATGGCGCAGT  ATGAAGATGG  TAAACAGTAC  ACTACCCTGG  AAAAACCGGT  AGCTGGCGCG     60

CCTTCTGGTT  CTTTCATGGG  TGGTGACCTG  GGCAAAGATC  TGACTCAGGC  ATGGGCTGTG    120

GCGATGGCGC  TGGGCGTGGA  AGACAAAGTG  ACTGTTCCGC  TGTTTGAAGG  CGTACAGAAA    180

ACCCAGACCA  TTCGTTCTGC  TTCTGATATC  CGCGATGTAT  TTATCAACGC  AGGTATTAAA    240

GGTGAAGAGT  ACGACGCGGC  GTGGAACAGC  TTCGTGGTGA  AATCTCTGGT  CGCTCAGCAG    300

GAAAAAGCTG  CAGCTGACGT  GCAATTGCGT  GGCGTTCCGG  CGATGTTTGT  TAACGGTAAA    360

TATCAGCTGA  ATCCGCAGGG  TATGGATACC  AGCAATATGG  ATGTTTTTGT  TCAGCAGTAT    420

GCTGATACAG  TGAAATATCT  GTCCGAGAAA  AAACATCATC  ACCATCATCA  CAGCATGCAG    480

ATTTCGTCA   AGACTTTGAC  CGGTAAAACC  ATAACATTGG  AAGTTGAACC  TTCCGATACC    540

ATCGAGAACG  TTAAGGCGAA  AATTCAAGAC  AAGGAAGGTA  TCCCTCCAGA  TCAACAAAGA    600

TTGATCTTTG  CCGGCAAGCA  GCTAGAAGAC  GGTAGAACGC  TGTCTGATTA  CAACATTCAG    660

AAGGAGTCCA  CCTTACATCT  TGTGCTAAGG  CTCCGCGGTG  GTGGTCCGGA  AACCCTGTGC    720

GGTGCTGAAC  TGGTTGACGC  TCTTCAGTTC  GTTTGCGGTG  ACCGTGGTTT  CTACTTCAAC    780

AAACCGACCG  GTTACGGTTC  CTCCTCCCGT  CGTGCTCCGC  AGACCGGTAT  CGTTGACGAA    840

TGCTGCTTCC  GGTCCTGCGA  CCTGCGTCGT  CTGGAAATGT  ACTGCGCTCC  GCTGAAACCG    900

GCTAAATCCG  CTTAA                                                        915
```

EXPRESSION OF FUSION POLYPEPTIDES TRANSPORTED OUT OF THE CYTOPLASM WITHOUT LEADER SEQUENCES

CROSS-REFERENCE APPLICATIONS

This application is a continuation-in-part of U.S. patent application Ser. No. 08/100,744, filed Aug. 2, 1993.

TECHNICAL FIELD

The invention relates to the field of recombinant protein synthesis. In particular, polypeptides of interest are expressed as fusion polypeptides, comprising fusion partners that lack leader sequences, and wherein the fusion partners cause the fusion polypeptides to be secreted from the cytoplasm of host cells.

BACKGROUND ART

Genetic engineering has made it possible to produce large amounts of polypeptides encoded by cloned DNA by means of recombinant expression systems, especially by expression in such prokaryotes as Escherichia coli (E. coli). The expressed heterologous polypeptide, which would otherwise either not be produced at all by the host cell or be produced only in limited amounts, may constitute a significant proportion of the total cellular polypeptide of the host cell.

Several problems are frequently encountered, however. Polypeptides over-expressed in the bacterial cytoplasm often accumulate as insoluble "inclusion bodies" (Williams et al., Science 215:687–688, 1982; Schoner et al., Biotechnology 3:151–154, 1985). Inclusion body formation is not limited to bacterial expression systems. For example, the Krüppel gene product of Drosophila can form inclusion bodies when produced in insect cells using a baculovirus expression system. Polypeptides accumulated in the form of inclusion bodies are relatively useless for screening purposes in biological or biochemical assays, or as pharmaceutical agents. Conversion of this insoluble material into active, soluble polypeptide requires slow and difficult solubilization and refolding protocols which often greatly reduce the net yield of biologically active polypeptide.

Even when heterologous polypeptides are expressed in the cytoplasm of bacteria in soluble form, they often accumulate poorly as a result of degradation by host proteases. Further, the accumulated polypeptides often have a different amino terminus than that which is desired.

One approach to these problems is to fuse a polypeptide of interest to a polypeptide fusion partner such as the lacZ and trpE gene products (Goeddel et al., Proc. Natl. Acad. Sci. USA. 76:106–110, 1979; Furman et al. Biotechnology 5:1047–1051, 1987); maltose-binding polypeptide (Di Guan et al., Gene 67:21–30, 1988); glutathione-S-transferase (Johnson, Nature 338:585–587, 1989); ubiquitin (Miller et al., Biotechnology 2:698–704, 1989); or thioredoxin (LaVallie et al., Biotechnology 11:187–193, 1993). Often the fusion partner confers such desirable characteristics as greater solubility on the polypeptide of interest, especially when the recombinant host is cultured at temperatures below the optimum for growth (LaVallie et al., 1993, op. cit.). Low-temperature culture, however, introduces other practical problems which may make the process less suitable on a commercial scale.

The use of polypeptide fusions also allows the production of polypeptides which might otherwise be too small to accumulate efficiently in the recombinant host (Schultz et al., J. Bacteriol. 169:5385–5392, 1987). Further, appropriate fusion partners may act, e.g., as affinity peptides, facilitating recovery and purification of the fusion polypeptide from cell extracts containing hundreds of other polypeptides (see, e.g., WO 91/11454).

The use of fusion polypeptides has drawbacks, however. It is often necessary to cleave the desired polypeptide away from the fusion partner by enzymatic or chemical means. This can be accomplished by placing an appropriate target sequence for cleavage between that for the fusion partner and for the desired polypeptide. Unfortunately, the enzymes most widely used for polypeptide cleavage are expensive, inefficient, or imprecise in their cleavage, and cannot always be successfully applied to a majority of fusion constructs. For example, while enterokinase and Factor Xa are highly specific endoproteases, these mammalian enzymes are expensive to produce and require that a polypeptide of interest expressed in a prokaryotic host cell be isolated from the host cell before being treated with the mammalian enzyme, adding considerable expense to a large-scale process. In addition, the efficiency and specificity with which some enzymes cleave substrates is highly variable. While an enzyme like subtilisin, for example, may be relatively inexpensive to produce, the precision with which it cleaves substrates is less than acceptable for commercial-scale processes under current "Good Manufacturing Practices" (GMP).

Some yeast ubiquitin hydrolases efficiently cleave fusions in which ubiquitin is the fusion partner and the amino acid immediately downstream of the cleavage site is not proline (Miller et al., op. cit., 1989; Tobias and Varshavsky, J. Biol. Chem. 266:12021–12028, 1991; see also WO 88/02406 and WO 89/09829). One ubiquitin hydrolase gene cloned from the yeast Saccharomyces cerevisiae (S. cerevisiae), YUH-1 (Miller et al., op. cit. 1989), will not efficiently cleave fusions in which the downstream polypeptide is larger than about 25 kD. Another S. cerevisiae ubiquitin hydrolase gene (Tobias and Varshavsky, J. Biol. Chem. 266:12021–12028, 1991) is capable of cleaving ubiquitin fusions in which the polypeptide downstream of the cleavage site is as large as 130 kD. Both ubiquitin hydrolases are active when expressed intracellularly in E. coli, allowing them to be used to cleave fusions in vivo. However, the use of ubiquitin as a fusion partner is hampered by the fact that multi-copy plasmids carrying ubiquitin fusion constructs may cause E. coli host cells, for example, to grow slowly and lose viability.

Cytoplasmic accumulation of fusion polypeptides suffers from the drawback that the heterologous polypeptide moiety may not be able to fold correctly in the strong reducing environment of the cytoplasm, leading to poor yields of biologically active polypeptide. To overcome this problem the polypeptide of interest may be fused to a "signal peptide", a short (15–30 amino acid) sequence present at the amino terminus of precursor polypeptides destined for secretion, i.e. export to non-cytoplasmic locations. In E. coli such locations would include the inner membrane, periplasmic space, cell wall and outer membrane. Typically, at some point just prior to or during transport of polypeptides out of the cytoplasm, the signal sequence is removed by host enzymes to produce the "mature" polypeptide. In these cases in which the signal sequence is removed by host enzymes to produce the "mature" polypeptide, the signal sequences are also known as "leader peptides" (For a recent review of the general secretory pathway in gram-negative bacteria and a discussion of leader peptides, see Pugsley, Microbiol. Rev. 57:50–108, 1993).

Localization of an expressed polypeptide to the periplasmic space is advantageous because simpler methods of polypeptide recovery can be used, including "osmotic shock" and other techniques. Although leader sequences may be used to deliver heterologous polypeptides into the periplasmic space of *E. coli*, few polypeptides are efficiently accumulated in soluble form by this method. Translocation of polypeptides across the lipid bilayer of the inner membrane appears to be inefficient, particularly in the case of fusions comprising leader sequences linked to heterologous polypeptides.

Only a few polypeptides that naturally lack a leader sequence are secreted to non-cytoplasmic (or periplasmic) locations, as demonstrated by their selective release from cells upon treatment with osmotic shock or freeze-thaw protocols. These include thioredoxin (Lunn and Pigiet, op. cit., 1982) and elongation factor-Tu (EF-Tu) (Jacobson et al., *Biochemistry* 15:2297–2302, 1976). IL-1-β expressed in *E. coli* has been extracted by a modified osmotic shock procedure (Joseph-Liauzun et al., op. cit., 1990).

Extracellular localization may also be advantageous and may be accomplished by at least two different strategies: (1) Permeabilization of the outer membrane, allowing periplasmic polypeptides to "leak" out (U.S. Pat. No. 4,595,658; Kato et al., *Gene* 54:197–202, 1987); and (2) fusion to sequences which direct extracellular export (Nagahari et al., *EMBO J.* 4:3589–3592, 1985; U.S. Pat. No. 5,143,830). However, these methods do not work in many cases; and even if they do work, the methods generally are inefficient and often do not produce polypeptides with the desired amino terminus (Holland et al., *Biochimie* 72:131–141, 1990).

In the construction of a fusion polypeptide, the ideal fusion partner would be one which is useful for the production of a wide variety of heterologous polypeptides in a recombinant host cell, e.g., *E. coli*, at optimum growth temperatures. Preferably, such a fusion partner would improve the accumulation of the desired polypeptide in soluble, active form in a cellular location in which it is protected, e.g., from proteolysis, and where the fusion polypeptide may be recovered by simplified procedures. It would also be advantageous if such a fusion partner would allow the use of an efficient, inexpensive and precise cleavage system in vivo.

DISCLOSURE OF INVENTION

The present invention is directed to fusion polypeptides that are selectively transported out from a host cell's cytoplasm comprising a fusion partner that consists essentially of a mature polypeptide or fragment thereof, wherein said fusion partner lacks any leader sequence. Specifically, the invention encompasses fusion polypeptides comprising: (a) a fusion partner capable of directing extracytoplasmic transport, consisting essentially of at least one fragment of a mature polypeptide, wherein the mature polypeptide is selected from the group consisting of interleukin-1-like polypeptides and leader-deleted-translocating polypeptides; and (b) a polypeptide of interest, wherein said polypeptide of interest is positioned distal to the carboxy terminus of said fusion partner. Preferably, the fusion polypeptides of the invention further comprise a linker peptide positioned between said fusion partner and said polypeptide of interest. Most preferably, the linker peptide comprises a cleavage site, e.g. one cleaved by ubiquitin hydrolase.

The fusion polypeptides of the invention may be produced in a wide variety of host cells, e.g., *E. coli*, in soluble, active, and easily recoverable form at temperatures at or close to the physiological optima for host cell growth. A variety of polypeptides of interest may be produced in this manner, including enzymes, growth factors, single-chain antibodies, DNA- or RNA-binding proteins, membrane receptors, and fragments thereof.

Also embodied by the present invention are nucleic acids, preferably expression vectors, encoding the fusion polypeptides of the invention and host cells comprising such nucleic acids. Preferably, such host cells additionally comprise a nucleic acid capable of expressing in the cytoplasm of the host cell a proteolytic enzyme which specifically recognizes a cleavage site in the fusion polypeptide, preferably in the linker. Such a system is useful for in vivo cleavage of the fusion polypeptides, particularly when ubiquitin hydrolase is co-expressed and cleaves the fusion polypeptide at a compatible cleavage site located within a linker positioned between the fusion partner and the polypeptide of interest.

These transformed host cells are useful for the recombinant production of polypeptides of interest as fusion polypeptides, again, preferably using in vivo cleavage to cleave away from the polypeptide of interest other sequences of the fusion polypeptide, e.g., the IL-1-like polypeptide, the leader-deleted-translocating polypeptide, and linker.

The present invention further embodies methods of producing substantially purified fusion polypeptides of the invention that are encoded by a nucleic acid of the invention comprising the steps of: (a) introducing said nucleic acid encoding said fusion polypeptide into a host cell, thereby producing a transformed host cell; (b) culturing said transformed host cell under conditions appropriate for expressing said fusion polypeptide, thereby expressing said fusion polypeptide; and (c) purifying said fusion polypeptide, thereby obtaining a substantially purified fusion polypeptide.

The present invention further embodies methods of producing substantially purified polypeptides of interest comprising the steps of: (a) introducing into a host cell a nucleic acid of the invention encoding one of the fusion polypeptides of the invention which comprises a linker peptide comprising a cleavage site, thereby producing a transformed host cell; (b) culturing said transformed host cell under conditions appropriate for expressing said fusion polypeptide, thereby expressing said fusion polypeptide; (c) cleaving said fusion polypeptide with a proteolytic enzyme or cleavage agent which recognizes said cleavage site, thereby producing said polypeptide of interest; and (d) purifying said polypeptide of interest, thereby obtaining a substantially purified polypeptide of interest.

The present invention further embodies methods of producing substantially purified polypeptides of interest comprising the steps of: (a) introducing into a host cell a nucleic acid of the invention encoding one of the fusion polypeptides of the invention which comprises a linker peptide comprising a cleavage site, wherein said host cell further comprises a nucleic acid capable of expressing in said host cell a proteolytic enzyme which specifically recognizes said cleavage site; thereby producing a transformed host cell; (b) culturing said transformed host cell under conditions appropriate for expressing said fusion polypeptide and said proteolytic enzyme, thereby expressing said fusion polypeptide, causing the in vivo cleavage of said fusion polypeptide, and producing said polypeptide of interest; and (c) purifying said polypeptide of interest, thereby obtaining a substantially purified polypeptide of interest.

The present invention further embodies methods of producing substantially purified polypeptides of interest comprising the steps of: (a) introducing into a host cell a nucleic acid of the invention encoding one of the fusion polypeptides of the invention which comprises a linker peptide comprising a cleavage site, thereby producing a transformed host cell; (b) culturing said transformed host cell under conditions appropriate for expressing said fusion polypeptide, thereby expressing said fusion polypeptide; (c) purifying said fusion polypeptide, thereby producing a substantially purified fusion polypeptide; (d) cleaving said substantially purified fusion polypeptide with a proteolytic enzyme or cleavage agent which recognizes said cleavage site, thereby producing said polypeptide of interest; and (e) purifying said polypeptide of interest, thereby obtaining a substantially purified polypeptide of interest.

BRIEF DESCRIPTION OF DRAWINGS

FIG. 1 (SEQ ID NO: 1, SEQ ID NO: 2, SEQ ID NO: 3, SEQ ID NO: 4, and SEQ ID NO: 5) shows an alignment of the sequences of five members of the IL-1-like protein family: (1) E. coli DsbA (SEQ ID NO: 1), (2) human IL-1-β (SEQ ID NO: 2), (3) human IL-1-α(SEQ ID NO: 3), (4) human basic fibroblast growth factor (FGF)(SEQ ID NO: 4), and (5) human acidic FGF (SEQ ID NO: 5).

FIG. 7, left, shows SDS-PAGE gels of WCL, 0' and 120', and soluble ("S") and insoluble ("T") fractions from E. coli cells transformed with pDJ16920, which encodes ubiquitin-TGF-β2 fusion polypeptide, expected size approximately 20 kD, or plasmid pYZ22096, which encodes a DsbA-ubiquitin-TGF-β2 fusion, expected size approximately 42 kD.

FIG. 8, left: SDS-PAGE gels of WCL, 0' and 120' and soluble ("S") and insoluble ("T") fractions from E. coli cells transformed with pDJ16927, which expresses a ubiquitin-IGF fusion, expected size of about 15 kD, or with pDM16965, which expresses IL-1-β-ubiquitin-IGF, expected size approximately 32 kD. FIG. 8, right shows similar gels of extracts of E. coli cells transformed with pYZ22070, which encodes DsbA-ubiquitin-IGF, with an expected size of approximately 37 kD, or with pDM15426, which encodes DsbA-ubiquitin-IGF in which DsbA has its native signal sequence, expected size of about 37 kD.

FIG. 20 (SEQ ID NO: 22) shows the nucleic acid sequence for native dsbA (with leader)-biotinylation peptide (Plasmid 25453).

FIG. 21 (SEQ ID NO: 23) shows the nucleic acid sequence for leaderless dsbA (3'modified)-biotinylation peptide (Plasmid 25450).

FIG. 22 (SEQ ID NO: 24) shows the nucleic acid sequence for leaderless dsbA (3'modified)-hubi(de145).IGF.new (Plasmid 25477).

FIG. 23 (SEQ ID NO: 25) shows the nucleic acid sequence for leaderless dsbA (3'modified)-hubi.IGF.new (Plasmid 41620).

FIG. 24 (SEQ ID NO: 26) shows the nucleic acid sequence for native dsbA (Plasmid 9205).

FIG. 25 (SEQ ID NO: 27) shows the nucleic acid sequence for leaderless dsbC (3'modified) C>S variant (Plasmid 46805).

FIG. 26 (SEQ ID NO: 28) shows the nucleic acid sequence for leaderless dsbA (Plasmid 9206).

FIG. 27 (SEQ ID NO: 29) shows the nucleic acid sequence for leaderless dsbA (3'modified) (Plasmid 22055).

FIG. 28 (SEQ ID NO: 30) shows the nucleic acid sequence for leaderless mini-dsbA (3'modified) (Plasmid 25452).

FIG. 29 (SEQ ID NO: 31) shows the nucleic acid sequence for leaderless dsbA (3'modified)-y.ubi.IGF.old (Plasmid 22070).

FIG. 30 (SEQ ID NO: 32) shows the nucleic acid sequence for leaderless dsbC (3'modified)-hubi.IGF.new (Plasmid 25498) (Vector pUC18).

FIG. 31 (SEQ ID NO: 33) shows the nucleic acid sequence for leaderless dsbC (3'modified) C>S variant-IGF1 (new) (Plasmid 46806).

FIG. 32 (SEQ ID NO: 34) shows the nucleic acid sequence for leaderless dsbC (3'modified)-IGF1(new) (Plasmid 15486).

FIG. 33 (SEQ ID NO: 35) shows the nucleic acid sequence for leaderless dsbC (3'modified) (Plasmid 25492).

FIG. 34 (SEQ ID NO: 36) shows the nucleic acid sequence for mature human interleukin 1 beta (3'modified)-IGF(old) (Plasmid 16963) (Vector pBR322).

FIG. 35 (SEQ ID NO: 37) shows the nucleic acid sequence for mature human interleukin 1 beta (Plasmid 12151) (Vector pBR322).

FIG. 36 (SEQ ID NO: 38) shows the nucleic acid sequence for mature human interleukin 1 beta (3'modified) (Plasmid 15449).

FIG. 37 (SEQ ID NO: 39) shows the nucleic acid sequence for human interleukin 1 beta R11G mutant (3'modified) (Plasmid 25466).

FIG. 38 (SEQ ID NO: 40) shows the nucleic acid sequence for interleukin-1 receptor antagonist (3'modified)-IGF(new).

FIG. 39 (SEQ ID NO: 41) shows the nucleic acid sequence for leaderless interleukin-1 receptor antagonist (3'modified) (Plasmid 15424).

FIG. 40 (SEQ ID NO: 42) shows the nucleic acid sequence for mature human interleukin 1 beta (3'modified)-yubi.IGF.old (Plasmid 16965).

FIG. 41 (SEQ ID NO: 43) shows the nucleic acid sequence for mini-dsbA (3'modified)-hubi(de145).IGF.new (Plasmid 25499).

FIG. 42 (SEQ ID NO: 44) shows the nucleic acid sequence for leaderless mini-dsbA (3'modified)-hubi.IGF.new (Plasmid 25485) (Vector pUC18).

MODES FOR CARRYING OUT THE INVENTION

Figure 2:
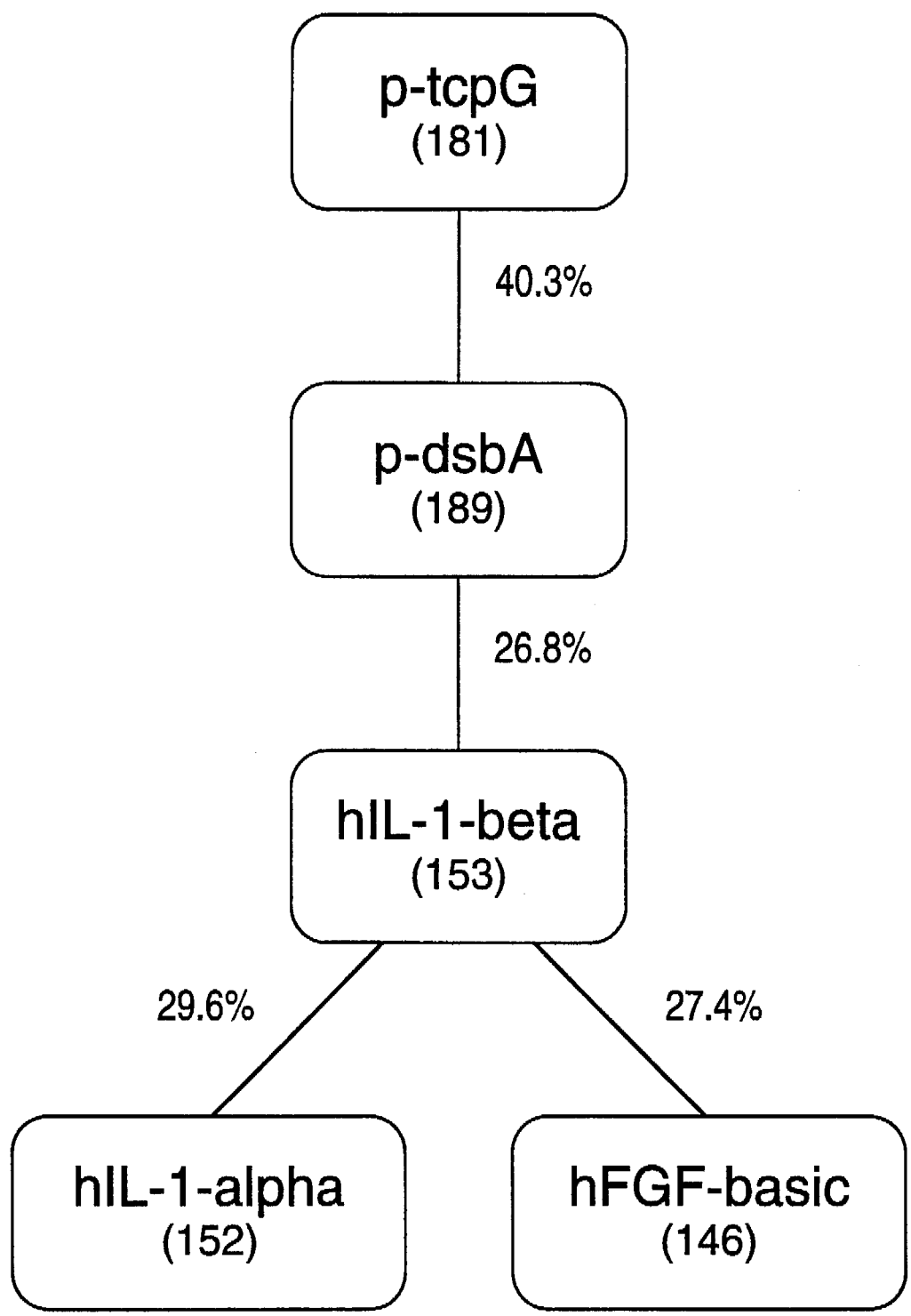
FIG. 2 summarizes the homologies between the mature polypeptides of E. coli DsbA, human IL-1-β, human IL-1-α, human basic fibroblast growth factor (FGF), and the toxin coregulated pilus (TcpG) polypeptide of Vibrio cholerae. The size of each of the mature polypeptides is given in parentheses.

A wide range of polypeptides, when fused to a fusion partner comprising an interleukin-1-like polypeptide ("IL-1-like polypeptide"), a leader-deleted-translocating polypeptide, or fragments thereof, accumulate in large quantities in soluble, active, easily recoverable form in a variety of host cells at temperatures close to or at the physiological optima for host cell growth. If desired, the polypeptide of interest may be cleaved away from the interleukin-1-like polypeptide efficiently and inexpensively either in vivo or in vitro. Both interleukin-1-like polypeptides and leader-deleted-translocating polypeptides are useful as generic fusion partners for the expression of a wide variety of heterologous polypeptides in both prokaryotic and eukaryotic cells, including E. coli, yeast, insect cells and mammalian cells.

Interleukin-1-β (IL-1-β) is one of a unique class of naturally secreted polypeptides which lack signal sequences (Muesch et al., TIBS, March 1990, pp. 86–88, 1990). Members of this class may be found in a wide range of species, from bacteria to humans. In mammalian monocytes IL-1-β transport out of the cytoplasm has been shown to be independent of the general secretory pathway (Rubartelli et al., EMBO J. 9:1503–1510, 1990; Singer et al., J. Exp. Med. 167:389–407, 1988; see also Rubartelli et al., J. Biol. Chem. 267:24161–24164, 1992).

Although IL-1-β does not contain an amino-terminal signal peptide or a significant hydrophobic region which could function as an internal signal sequence, when the gene for IL-1-β is expressed in E. coli host cells, the IL-1-β polypeptide can be released from the host cells by osmotic shock without lysing the cells (Joseph-Liauzun et al., Gene 86:291–295, 1990). Moreover, IL-1-β containing an amino-terminal methionine (Met-IL-1-β) is secreted by yeast cells (G. P. Livi, personal communication, reported in Joseph-Liauzun et al., op. cit., 1990).

It is believed that in mammalian monocytes IL-1 interacts with the cytoplasmic membrane, forms vesicles and is secreted without passing through the endoplasmic reticulum (ER) or Golgi apparatus. Because of this property, consensus glycosylation sites on the polypeptide remain unglycosylated. However, glycosylation of IL-1-β does occur if a cleavable signal sequence is attached to its amino terminus (Baldari et al., *EMBO J.* 6:229–234, 1987). The use of IL-1-like polypeptides as fusion partners can therefore permit production of nonglycosylated polypeptides in mammalian cells. This feature will be especially important in cases in which the glycosylation of a polypeptide of interest would be undesirable. For example, when human proteins are synthesized in other mammalian cells, different glycosylation may occur and may be antigenic to human recipients. This is a major area of concern for those interested in expressing polypeptides useful as human therapeutics in such transgenic animals as goats or sheep.

Moreover, since the alternative route of transport out of the cytoplasm employed by IL-1-like polypeptides avoids the ER, it may be advantageous to express polypeptides with free sulfhydryl groups, e.g., bFGF, PD-ECGF, and ADF (Takahashi et al., *Proc. Natl. Acad. Sci. USA.* 83:8019–8023, 1986), as fusions to IL-1-like polypeptides because IL-1-like fusions avoid the oxidizing milieu of the ER lumen.

Also, IL-1-like fusions appear to be secreted without translocation across a lipid bilayer. Thus, using IL-1-like fusions with heterologous polypeptides which cannot normally be secreted via the general secretory pathway now permits the successful transport out of the cytoplasm of those polypeptides. Examples include but are not limited to polypeptides containing long hydrophobic or other sequences which can interfere with passage through the lipid bilayer.

For the purposes of the present invention, an "interleukin-1-like" (or "IL-1-like") polypeptide is a polypeptide or functional fragment thereof which may be characterized by a three-dimensional structure substantially similar to that of mature human interleukin-1-β (Priestle et al., *Proc. Natl. Acad. Sci. USA.* 86:9667–9671, 1989) When fused to a polypeptide of interest, such an IL-1-like polypeptide is also capable of directing the transport out of the cytoplasm of that fusion polypeptide into a privileged cellular compartment in which the fusion polypeptide is soluble and biologically active but is protected from proteolysis.

In nature, mature IL-1-β is relatively small (about 17 kD) and stable. It is synthesized as a large inactive precursor which is later cleaved to release a mature polypeptide 153 amino acids long. Mature IL-1-β possesses a uniquely stable structure—a so-called beta-trefoil fold—characterized by three similar units arranged around a three-fold axis of symmetry to form a barrel structure, each unit containing two pairs of antiparallel beta strands (Priestle et al., op. cit., 1989). This beta-trefoil fold, a structure which contains no alpha helices, may serve to stabilize the overall structure of a fusion polypeptide of which it is a part. Members of the beta-trefoil structural family include but are not limited to the following: IL-1-α and IL-1-β; members of the fibroblast growth factor (FGF) family including, e.g., acidic FGF and basic FGF, int-2, hst/KS3, FGF-5, FGF-6, and keratinocyte growth factor (Zhang et al., *Proc. Natl. Acad. Sci. USA.* 88:3446–3450, 1991; Zhu et al., *Science* 251:90–93, 1991); hisactophilin (Habazettl et al., Nature 359:855–857, 1992); and soybean trypsin inhibitor (Wolfson et al., *Biochemistry* 32:5327–5331, 1993). See also McDonald and Hendrickson, *Cell* 73:421–424, 1993.

Polypeptides which share the beta-trefoil structure will be considered IL-1-like polypeptides if, like IL-1, they are capable of directing the transport out of the cytoplasm of a fused polypeptide of interest into a privileged cellular compartment from which it can readily be released in active form, e.g., by a selective extraction procedure. Thus, the presence of a beta-trefoil structure may be used to demonstrate that a potential fusion partner is an interleukin-1-like polypeptide. For example, basic FGF, which lacks a leader sequence, is known to be secreted from cells by a process similar to that for IL-1-β (Abraham et al., *Science* 233:545–548, 1986).

"IL-1-like polypeptides" include only mature polypeptides and functional fragments thereof, which: (a) lack an amino-terminal leader sequence recognizable by the method of von Heijne (*Nucl. Acids. Res.* 14:4683–4690, 1986); (b) have an amino acid sequence that is at least 20% homologous with the amino acid sequence of mature human interleukin-1-β (IL-1-β) when optimally aligned; and (c) are capable of directing the translocation of greater than about 20% of a fusion polypeptide into a privileged cellular compartment. Where an IL-1-like polypeptide is naturally synthesized as a precursor with an amino-terminal leader sequence, only the DNA sequence corresponding to the mature polypeptide, i.e., lacking a leader sequence, is considered the nucleic acid encoding the "IL-1-like polypeptide" for the purposes of the present invention. Thus, the "IL-1-like polypeptides" of the present invention include the members of the interleukin-1 gene family, which includes interleukin-1-α and -β and the interleukin-1 receptor antagonist (IL-1ra) from human and nonhuman species, e.g., mouse and rat, (Eisenberg et al., *Nature* 343:341–346, 1990; Eisenberg et al., *Proc. Natl. Acad. Sci. USA.* 88:5232–5236, 1991), as well as DsbA from *E. coli* and related bacteria.

The mature *E. coli* DsbA polypeptide (Bardwell et al., *Cell* 67:581–589, 1991; Kamitani et al., *EMBO J.* 11:57–62, 1992) and its known bacterial homologs (including *Vibrio cholerae* TcpG; Peek and Taylor, *Proc. Natl. Acad. Sci. USA.* 89:6210–6214, 1992) are also examples of IL-1-like polypeptides by these criteria. DsbA is normally secreted to the periplasmic space, presumably with the aid of an amino-terminal leader sequence of 19 amino acids which is removed during translocation. However, a DsbA polypeptide variant in which the leader peptide is replaced by a single methionine displays unexpected behavior: Not only does the polypeptide cross the cell membrane, but transport across the membrane is actually increased. DsbA also can be released from cells by a modified osmotic shock procedure and other simplified methods which do not lyse the cell, as is shown in the Examples below.

FIG. 1 shows the sequence similarity between human IL-1-β DNA and the truncated dsbA gene. To maximize alignment, two regions of the dsbA sequence (corresponding to amino acid residues 21–35 and 126–157) are excluded from the comparison. The first of these segments (21–35) contains an example of a "double cysteine active site loop domain" which exhibits partial homology to the active site regions of other oxidoreductases (Bardwell et al., op. cit., 1991). This region of homology is absent from the other classes of IL-1-like polypeptides, suggesting that this region is not necessary for the properties of the IL-1-like polypeptides of the present invention. These double cysteine active site loop domains, e.g., the domain contained within residues 21–35 of DsbA, may be removed (or replaced) from fusion partners comprising any of the oxidoreductases that fall into the interleukin-1-like polypeptide or leader-deleted-translocating polypeptide classes and may not affect transport of a fusion polypeptide of the invention.

It should be noted that the term "interleukin" embraces a large number of proteins—26 to date—which vary widely in terms of sequence homology and structure. Interleukins other than IL-1 would generally not be considered "IL-1-like polypeptides" as defined above.

Thioredoxin is not considered an IL-1-like polypeptide. Thioredoxin secretion is similar in certain aspects to that of the IL-1-like polypeptides in that E. coli thioredoxin lacks a leader sequence and mammalian thioredoxin appears to be secreted without engaging the ER and Golgi apparatus. However, there is less than 15% sequence homology between IL-1 and thioredoxin, and there is no obvious similarity in their three-dimensional structures. Moreover, the secretion of IL-1-β differs from that of thioredoxin. For example, COS transfectants secrete thioredoxin but not IL-1-β. Moreover, in activated monocytes, some IL-1-β is found within intracellular vesicles, while the thioredoxin is not detected in membrane-bound compartments such as vesicles, suggesting that secreted thioredoxin molecules translocate directly to the plasma membrane (Rubartelli et al., op. cit., 1992). Thioredoxin preferentially resides at sites around the inner periphery of the cytoplasmic membrane in E. coli as adhesion zones, or Bayer's patches (sites at which there are gaps in the peptidoglycan cell wall where the inner and outer cell membranes are fused together). These observed differences in secretion between IL-1-β and thioredoxin indicate that these two polypeptides may employ different secretory pathways.

LaVallie et al. (op. cit., 1993) have proposed the use of thioredoxin as a fusion partner, although some thioredoxin fusions become more soluble as the growth temperature of cells expressing them is lowered (LaVallie et al., op. cit., 1993).

"Leader-deleted-translocating polypeptides" include only mature polypeptides and functional fragments thereof, which: (a) are derived from proteins which in their native states comprise amino-terminal leader sequences when first translated, wherein the amino-terminal leader sequences are subsequently cleaved in the formation of the mature proteins; and (b) are capable of directing the translocation of greater than about 20% of a fusion polypeptide into a privileged cellular compartment. While all proteins from which leader-deleted-translocating polypeptides are derived, naturally are synthesized as precursors with amino-terminal leader sequences, only the DNA sequences corresponding to the mature polypeptides, i.e., those lacking any leader sequence, are considered the nucleic acid encoding the "leader-deleted-translocating polypeptide" for the purposes of the present invention.

Thus, "leader-deleted-translocating polypeptides" of the present invention include the DsbA and DsbC proteins of E. coli and related bacteria, as well as the interleukin-1 receptor antagonist (IL-1ra) from human and nonhuman species, e.g., mouse and rat, (Eisenberg et al., Nature 343:341–346, 1990; Eisenberg et al., Proc. Natl. Acad. Sci. USA. 88:5232–5236, 1991).

Determining the identity of other IL-1-like polypeptides and leader-deleted-translocating polypeptides can readily be performed by one of ordinary skill in the art. For IL-1-like polypeptides, those proteins which meet the 20% sequence homology requirements can serve as lead candidates to be screened for activity, e.g., being subject to transport out of the cytoplasm. For leader-deleted-translocating polypeptides, proteins which are naturally synthesized as precursors with amino-terminal leader sequences and are naturally secreted into a privileged cellular compartment, like the periplasm, can serve as lead candidates, particularly oxidoreductases and most particularly the Dsb proteins of E. coli and related bacteria.

While the present invention includes fusion polypeptides comprising a fusion partner with one or more fragments derived from a single IL-1-like polypeptide or a single leader-deleted-translocating polypeptide, fusion polypeptides comprising fusion partners which are derived from multiple IL-1-like polypeptides, multiple leader-deleted-translocating polypeptides, or a combination of fragments derived from both classes of polypeptides is specifically contemplated in the present invention. In addition, the present invention specifically includes the use of mutant IL-1-like polypeptides or mutant leader-deleted-translocating polypeptides in the fusion partners of the fusion polypeptides of the invention. Such mutations may include deletions, the exchange of amino acids, or the addition of amino acids, particularly mutant polypeptide fragments of mature interleukin-1-β that are "defective with respect to interleukin-1-β biological activity" (having less than 3% of wild type interleukin-1-β biological activity).

Fusion polypeptides comprising the DNA sequence of an IL-1-like polypeptide or leader-deleted-translocating polypeptide fused to the DNA of a selected heterologous polypeptide, or any peptide of interest, may be readily constructed by conventional genetic engineering techniques. The IL-1-like polypeptide is preferably fused to the amino terminus of a selected heterologous polypeptide, although insertion of the selected polypeptide into a site within an IL-1-like polypeptide may also be appropriate. For example, heterologous polypeptidase inhibitor loops have been inserted into IL-1-β at an internal site. See Wolfson et al., op. cit., 1993.

The nucleic acid encoding the fusion polypeptide may optionally contain, in addition to the fusion partner comprising IL-1-like polypeptide or leader-deleted-translocating polypeptide, and the polypeptide of interest, additional "linker" DNA encoding additional amino acids. The linker peptide is positioned between the fusion partner and the peptide of interest.

A linker peptide may serve a number of functions. First, a linker may provide a specific cleavage site between the IL-1-like polypeptide and the polypeptide of interest. Such a cleavage site may contain a target for a proteolytic enzyme such as, for example, Factor Xa, trypsin, collagenase, thrombin, or subtilisin enterokinase, or, preferably, ubiquitin hydrolase; or for such chemical "cleavage agents" as, for example, cyanogen bromide, or hydroxylamine.

The cleaving steps can be performed in vivo by a proteolytic enzyme which is expressed by the host cell and specifically recognizes the proteolytic cleavage site of the linker peptide. Alternatively cleaving steps can be performed on fusion polypeptide samples with or without a prior purification step to remove host cell material, and followed by a purification step to remove the cleavage agent or proteolytic enzyme, and cleaved protein fragments, e.g., fusion partners and linkers. The methods for cleaving the peptide of interest from the fusion proteins of the invention, and the various related purification steps are specific to the cleavage agent or proteolytic enzyme used, and are known in the art. Examples of appropriate methods of cleaving steps and purification steps are described below and exemplified in the Examples section below.

A linker may also encode an "affinity tag" to aid in the purification of the fusion polypeptide away from other cellular polypeptides. For example, multiple histidine residues encoded by the linker allow the use of metal chelate affinity chromatography methods for purification of the fusion polypeptide.

The linker may also serve as a spacer, e.g., to prevent stearic hindrance in a fusion polypeptide between the IL-1-like polypeptide and the polypeptide of interest. Whether a linker is necessary will depend upon the structural and functional characteristics of the polypeptide of interest to be fused to an IL-1-like polypeptide, as will be apparent to those skilled in the art. If the polypeptide of interest is naturally cleaved, no linker may be necessary. The fusion polypeptide itself may be useful without cleavage.

The linker may serve any or all of these purposes or additional functions, or other functions as desired.

The ability of the IL-1-like polypeptide or leader-deleted-translocating polypeptide to target a fusion polypeptide to an extracytoplasmic space in the presence of other sequences within the same host cell (e.g., after permeabilization of the outer membrane, allowing periplasmic polypeptides to "leak" out, as taught in U.S. Pat. No. 4,595,658) simplifies the purification of the fusion polypeptide, since E. coli, for example, secretes few polypeptides to the culture medium. Alternatively, simply treating whole cells expressing the fusion polypeptide with appropriate extraction buffers, as shown in the Examples below, can selectively release the fusion polypeptide without releasing the majority of cytoplasmic polypeptides or nucleic acids. Such selective release greatly simplifies purification of the fusion polypeptide.

A wide variety of polypeptides, including those which are otherwise unstable or largely insoluble, may be expressed as fusions with the IL-1-like polypeptides or leader-deleted-translocating polypeptides of the present invention in prokaryotic or eukaryotic cells by employing appropriate expression systems.

In brief, the present invention provides methods and compositions in which a nucleic acid comprising sequences encoding an IL-1-like-polypeptide or leader-deleted-translocating polypeptide are fused to a polypeptide of interest, preferably in an expression vector. In the Examples, a T7 RNA polymerase-driven expression system (Studier and Moffat, J. Mol. Biol. 189:113–130, 1986), modified by translational coupling (Squires et al., J. Biol. Chem. 263:16297–16302, 1988), has been utilized to express large quantities of fusion polypeptides in which an IL-1-like polypeptide sequence is attached to the amino terminus of a heterologous polypeptide via a linker polypeptide sequence. Several examples of heterologous polypeptides have been used to show the generic properties of this expression system, including two growth factors, two enzymes, a single-chain antibody, a binding polypeptide and the extracellular domain of a membrane-spanning receptor. The Examples show that the methods and compositions of the present invention enable the high-level soluble expression of certain desirable therapeutic polypeptides, e.g. IGF-I, which are otherwise produced at low levels in bacterial host cells.

The production of fusion polypeptides according to this invention reliably improves the solubility of desired heterologous polypeptides and, by promoting the folding of the desired polypeptides into active conformations and sequestering the fusion polypeptides into a privileged compartment inside the host cell or causing transport out of the cytoplasm of the host cell, enhances the stability and accumulation of the heterologous polypeptide products.

Further, the present invention permits the screening of libraries of random polypeptides by assays for their biological function. When fused to an IL-1-like polypeptide, the random polypeptides accumulate in a protected cellular compartment in a soluble, active form. Functional screening of expression libraries containing mammalian DNA has been hampered by the fact that there is no assurance that the desired protein's function is maintained. This problem can easily be obviated by cloning the gene sequences of the library into an expression vector including a sequence for an IL-1-like polypeptide so that the library sequences can be expressed as IL-1 fusions. For example, colonies of E. coli cells transformed with the library are transferred to a solid support such as a nylon membrane. There the cells are gently lysed (e.g., using a mild detergent such as Triton-X 100) to release the expressed fusion polypeptides, and the fusion polypeptides are screened for biological activity which identifies the clone with the gene of interest.

Additionally, the fusion polypeptides of the present invention may be used to develop antibodies, including monoclonal antibodies, by well known methods familiar to those skilled in the art.

Polypeptides

Ordinarily, the IL-1-like polypeptides of the present invention are at least about 20% homologous to the native human IL-1-$\beta$ polypeptide, preferably at least 40–60%, and more preferably at least about 95% homologous. Such homology is considered to be "substantial homology," although the common possession of the three-dimensional structure characteristic of IL-1, while not required, may be used to identify and IL-1-like polypeptide.

Polypeptide homology is typically analyzed using sequence analysis software such as the Sequence Analysis Software Package of the Genetics Computer Group, University of Wisconsin Biotechnology Center (1710 University Avenue, Madison, Wis. 53705). Polypeptide analysis software matches similar sequences using measures of homology assigned to various substitutions, deletions, substitutions, and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

A "fragment" of an IL-1-like polypeptide or a leader-deleted-translocating polypeptide is a portion of a full length IL-1-like or leader-deleted-translocating polypeptide which substantially retains its functional characteristics. That is, an IL-1-like polypeptide fragment or leader-deleted-translocating polypeptide fragment is one capable of directing the translocation of at least about 20% of a fusion polypeptide to an appropriate privileged cellular compartment of the host cell in which it is expressed. Also the phrase "capable of directing extracytoplasmic transport" is used to mean that the polypeptide or fragment so described is one that is capable of being targeted to an appropriate protected cellular compartment of the host cell in which it is expressed.

In addition, The terms "leader peptide", "signal peptide", and "leader" are used interchangeably herein to mean short (15–30 amino acid) sequences present at the amino terminus of precursor polypeptides destined for secretion, i.e. export to non-cytoplasmic locations, which are not present in mature proteins.

"Isolated"

The terms "isolated," "substantially pure," "substantially purified," and "substantially homogeneous" are used interchangeably to describe a polypeptide which has been separated from its natural components including, for example, a linker sequence, etc., which has been chemically or enzymatically cleaved in order to obtain the polypeptide of interest without such components. A monomeric polypeptide is substantially pure when at least about 60 to 75% of a sample exhibits a single polypeptide sequence. A substantially pure polypeptide typically comprises about 60 to 90% W/W of a polypeptide sample, more usually about 95%, and preferably is over about 99% pure. Polypeptide purity or homogeneity may be indicated by a number of means well known in the art, such as polyacrylamide gel electrophoresis of a polypeptide sample, followed by visualizing a single polypeptide band upon staining the gel. For certain purposes higher resolution can be provided by using HPLC or other means well known in the art.

Polypeptide Purification

When expressed in bacterial cells, fusion polypeptides comprising an IL-1-like polypeptide or leader-deleted-translocating polypeptide moiety may be released from the cells by modified osmotic shock, freeze/thaw procedures, or by resuspension in certain extraction buffers, as exemplified below. Further polypeptide purification can be accomplished by various methods well known in the art, e.g., affinity chromatography.

It may be advantageous to cleave the fusion polypeptide in order to isolate a polypeptide of interest away from a fusion partner and/or linker sequence or other sequences comprising the fusion polypeptide of which it is a part. A linker comprising a sequence encoding a polyhistidine stretch, for example, can be purified by binding to a resin such as Ni-NTA resin (QIAGEN, Chatsworth, Calif.) and ProBond resin (Invitrogen, San Diego, Calif.). Other useful methods of polypeptide purification are described, e.g., in Guide to Polypeptide Purification, ed. M. Deutscher, 182 Meth. Enzymol. (Academic Press, Inc.: San Diego, 1990) and R. Scopes, Polypeptide Purification: Principles and Practice, Springer-Verlag: New York, 1982.

Preferably, cleavage of the fusion polypeptide occurs in vivo via the co-expression of a compatible proteolytic enzyme in the cytoplasm of the host cell. In bacterial hosts such as E. coli, ubiquitin hydrolase is preferred. When expressed along with a polypeptide having a ubiquitin hydrolase cleavage site, e.g., as part of a linker in the fusion genes of the present invention, ubiquitin hydrolase cleaves specifically and efficiently, as demonstrated in Example 6.

The intact fusion polypeptide may also be useful. For example, a fusion of human interleukin-1-β, or its analogues, to a second polypeptide may have therapeutic uses.

Polypeptide Modifications; Fragments; Fusion Polypeptides

The present invention also provides for polypeptides or fragments thereof which are substantially homologous to the primary structural sequence of the human IL-1-β polypeptide. The present invention also embraces polypeptides with in vivo or in vitro chemical and biochemical modifications or which incorporate unusual amino acids. Such modifications are well known and include, for example, acetylation, carboxylation, phosphorylation, glycosylation, ubiquitination, labelling, e.g., with radionuclides, various enzymatic modifications. See, e.g., Molecular Cloning: A Laboratory Manual, 2nd ed., Vol. 1–3, ed. Sambrook, et al., Cold Spring Harbor Laboratory Press (1989) or Current Protocols in Molecular Biology, ed. F. Ausubel et al., Greene Publishing and Wiley-Interscience: New York (1987 and periodic updates).

The present invention provides fusion polypeptides comprising an IL-1-like polypeptide or leader-deleted-translocating polypeptide, and any polypeptide of interest. Examples of polypeptides fused to an IL-1-like polypeptide or leader-deleted-translocating polypeptide include any peptide or polypeptide useful for human or veterinary therapy, diagnostic or research applications. Such polypeptides of interest include but are not limited to hormones, cytokines, growth or inhibitory factors, and enzymes.

The IL-1-like polypeptides, leader-deleted-translocating polypeptides, polypeptides of interest and fusion polypeptides are typically made by recombinant methods but may be chemically synthesized. Techniques for synthesis of polypeptides are described, for example, in Merrifield, J. Amer. Chem. Soc. 85:2149–2156, 1963.

Nucleic Acids

The present invention provides nucleic acids which encode a fusion polypeptide comprising an IL-1-like polypeptide or a leader-deleted-translocating polypeptide, and another polypeptide of interest. Such nucleic acids include RNA, cDNA, genomic DNA, synthetic forms, and mixed polymers, both sense and antisense strands. Such nucleic acids can be chemically or biochemically modified and can contain non-natural or derivatized nucleotide bases. The sequence encoding the fusion polypeptide can be interrupted by introns.

The nucleic acid sequences of this invention are of a length sufficient to encode such a fusion polypeptide and, if necessary, any vector sequences. The sequences are usually several hundred nucleotides or nucleotide base pairs in length and may be several kilobases long.

Techniques for nucleic acid manipulation, including the construction of nucleic acids capable of encoding and expressing the fusion polypeptides of the present invention, are well known and are described generally, for example, in Sambrook et al., op. cit., or Ausubel et al., op. cit. Reagents useful in applying such techniques, such as restriction enzymes and the like, are widely known in the art and commercially available.

The recombinant nucleic acid sequences used to produce fusion polypeptides of the present invention may be derived from natural or synthetic sequences. The nucleotide sequences and amino acid sequences and/or fragments thereof may be obtained from GENBANK and/or the Swiss Protein Database, with the database accession numbers as follows:

| Gene | GENBANK | Swiss-Prot |
|---|---|---|
| IGF | HUMIGFI | |
| | SYNHUMGFIS | |
| ubiquitin | YSCUBI1G | UBIQ_YEAST |
| | YSCUBI2G | |
| | YSCUBI3G | |
| | YSCUBI4G | |
| ubiquitin hydrolase | YSCUBP1 | |
| IL-1-β | HUMIL1AA | IL1B_HUMAN |
| IL-1-RA | HSIIRA | |
| IL-1-α | HUMIL1AA | |
| | AGHSIL1A | |
| FGF-β | HUMFGFB | |
| TGF-β | | TGF2_HUMAN |
| TGF-β-receptor II | HUMTGFBIIR | |
| IGFBP-3 | | IBP3_HUMAN |
| TcpG | VCDSBAG | |
| EGF-binding kallikrein | MUSEGFBPB | |

In the case of IGF and IGFBP-3, codon-optimized genes were employed. In all cases only the portions of each sequence coding for the mature gene product were used.

The nucleotide sequences of various IL-1-like and leader-deleted-translocating polypeptides have also been reported, e.g., in: Maliszewski et al., *Mol. Immunol.* 25:429–437, 1988; Auron et al., *Proc. Natl. Acad. Sci. USA.* 81:7907–7911, 1984; March et al., *Nature* (Lond.) 315:641–647, 1985; Lomedico et al., *Nature* (Lond.) 312:458–462, 1984; Gray et al., *J. Immunol.* 137:3644–3648, 1986; Nishida et al. in *Monokines and Other Nonlymphocytic Cytokines*, eds. Powanda et al. (Liss, New York), pp. 73–78, 1988; Furutani et al., *Nucl. Acids Res.* 13:5869–5882, 1985; Mori et al., *Biochem. Biophys. Res. Commun.* 150:1237–1243, 1988 (IL-1-α and IL-1-β from human, mouse, rat, bovine and rabbit); Eisenberg et at., *Proc. Natl. Acad. Sci. USA.* 88:5232–5236, 1991 (human, mouse, and rat IL-1ra); and Bardwell et al., *Cell* 67:581–589, 1991 (*E. coli* DsbA); Lovett and Kolodner, *J. Bacteriol.* 173:353–364, 1991; Missiakas et al., *EMBO J.* 13:2013–2020, 1994 (DsbC). These references are incorporated by reference herein.

Other sequences employed in the construction of the fusion polypeptides of the present invention include the soluble extracellular domain of the Type II TGF-β receptor (Lin et al., *Cell* 68:775–785, 1992) and EGF-binding kallikrein (Blaber et al., *Biochemistry* 26:6742–6749, 1987). Any expression vector compatible with a chosen host cell may be employed in the practice of the present invention.

Construction of the fusion polypeptides of the present invention is readily accomplished using well known methods in recombinant DNA technology, e.g., PCR, automated DNA synthesis, etc.

"Encode"

A nucleic acid is said to "encode" a polypeptide if, in its native state or when manipulated by methods well known to those skilled in the art, it can be transcribed and/or translated to produce the polypeptide. The anti-sense strand of such a nucleic acid is also said to encode the polypeptide.

"Operably Linked"

A nucleic acid sequence is operably linked when it is in a functional relationship with another nucleic acid sequence. For instance, a promoter is operably linked to a coding sequence if the promoter affects its transcription or expression. Generally, operably linked means that the DNA sequences being linked are contiguous and, where necessary to join two polypeptide coding regions, contiguous and in reading frame.

"Recombinant"

The term "recombinant" nucleic acid (and by analogy, a "recombinant" polypeptide produced by the expression of a recombinant nucleic a is one which is not naturally occurring or is made artificial combination of two otherwise separated segments of sequence by chemical synthesis means or artificial manipulation of isolated segments of nucleic acids, e.g., by genetic engineering techniques.

Preparation of Recombinant or Chemically Synthesized nucleic acids; Vectors, Transformation, Host Cells Large amounts of the nucleic acids of the present invention may be produced by replication in a suitable host cell, whether bacterial, yeast, insect, amphibian, avian, mammalian or other eukaryotic cells and expression systems. The natural or synthetic DNA fragments coding for a desired fragment will be incorporated into recombinant nucleic acid constructs, typically DNA constructs. These DNA constructs are introduced into prokaryotic or eukaryotic cells where they replicate. Usually the DNA constructs are suitable for autonomous replication in a unicellular host, such as yeast or bacteria. The constructs also can be introduced to and integrated within the genome of a cultured insect, mammalian, plant or other eukaryotic cell lines. Suitable methods for these purposes are well known in the art and have been described, e.g., in Sambrook et al. (1989) or Ausubel et al. (1987 and periodic updates).

The nucleic acids of the present invention are optionally produced by chemical synthesis, e.g., by the phosphoramidite method described by Beaucage and Carruthers (*Tetra. Letts.* 22:1859–1862, 1981) or the triester method according to Matteucci et al. (*J. Am. Chem. Soc.* 103:3185, 1981) and may be performed on commercial automated oligonucleotide synthesizers.

DNA constructs prepared for introduction into a prokaryotic or eukaryotic host typically comprise a replication system recognized by the host, including the intended DNA fragment encoding the desired polypeptide, and preferably also include transcription and translational initiation regulatory sequences operably linked to the polypeptide encoding segment. Expression vectors include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors are prepared by means of standard recombinant techniques well known in the art and discussed, for example, in Sambrook et al. (1989) or Ausubel et al. (1987).

Appropriate promoter and other necessary vector sequences are selected to function in the host. Examples of functional combinations of cell lines and expression vectors are described in Sambrook et al., 1989 or Ausubel et al., 1987); see also, e.g., Metzger et al., *Nature* 334:31–36, 1988. Many useful vectors are known in the art and are commercially available. For use in prokaryotic hosts, promoters include but are not limited to the trp, lac and phage promoters, tRNA promoters and glycolytic enzyme promoters. Useful yeast promoters include but are not limited to the promoter regions for metallothionein, 3-phosphoglycerate kinase or other glycolytic enzymes such as enolase or glyceraldehyde-3-phosphate dehydrogenase, and enzymes responsible for maltose and galactose utilization. Other suitable vectors and promoters for use in yeast expression are further described in Hitzeman et al. EP 73,657A. Appropriate nonnative mammalian promoters include but are not limited to the early and late promoters from SV40 (Fiers et al. *Nature* 373:113, 1978) or promoters derived from murine molony leukemia virus, mouse mammary tumor virus, avian sarcoma viruses, adenovirus II, bovine papilloma virus and polyoma virus. In addition, the construct can be joined to an amplifiable gene (e.g., DHFR) so that multiple copies of the gene are made.

Such expression vectors can replicate autonomously. In a less preferred mode, the expression vector can replicate by being inserted into the genome of the host cell, by methods well known in the art.

Expression and cloning vectors generally include a selectable marker, which encodes a polypeptide necessary for the survival or growth of its host cells. This gene's presence ensures the growth of only host cells expressing the marker. Typical selection genes encode polypeptides that (a) confer resistance to antibiotics or other toxic substances, e.g. ampicillin, neomycin, methotrexate, etc.; (b) complement auxotrophic deficiencies; or (c) supply critical nutrients not available from complex media. The choice of the proper selectable marker depends on the host cell. Appropriate markers for different hosts are well known in the art.

Vectors with the nucleic acids of interest can be transcribed in vitro, and the resulting RNA are introduced into host cells by well known methods (e.g., by injection). See, T. Kubo et al., FEBS Lett. 241:119, 1988. Alternately, the vectors can be introduced directly into host cells by methods well known in the art, which vary depending on the type of cellular host. These methods include but are not limited to electroporation; transfection employing calcium chloride, rubidium chloride calcium phosphate, DEAE-dextran, or other substances; microprojectile bombardment; lipofection; and infection (where the vector is an infectious agent, such as a retroviral genome). See generally, Sambrook et al. (1989) and Ausubel et al. (1987). The so-transformed cells are also meant to include the progeny of such cells.

Large quantities of the nucleic acids and polypeptides of the present invention are prepared by expressing the nucleic acids or portions thereof in vectors or other expression vehicles in compatible prokaryotic or eukaryotic host cells. The most commonly used prokaryotic hosts are strains of E. coli, although other prokaryotes, such as Bacillus subtilis or Pseudomonas, may also be used. Mammalian or other eukaryotic host cells, such as those of yeast, filamentous fungi, plant, insect, amphibian or avian species, may also be useful for production of the polypeptides of the present invention.

The invention has been disclosed by direct description. The following are examples showing the efficacy of the method in producing soluble, active polypeptides. The examples are only examples and should not be taken in any way as limiting to the scope of the invention.

EXAMPLES

Example 1: Expression and Purification of Fusion Proteins

The following materials and methods used throughout the Examples unless otherwise indicated. Further details can be found in the references cited herein.

Bacterial strains and growth conditions. E. coli JM109 F- traD36 lacIq del(lacZ)M15 proAB/recA1 endA1 gyrA96 thi hsdR17 supE44 relA1 del(lac-proAB).

E. coli W3110 DE3 F- thi (lambda DE3 lysogen; Studier and Moffat, J. Mol. Biol. 189:113–130, 1986).

These strains were grown in L-Broth at 37° C. with aeration unless otherwise indicated. For plasmid-containing strains, antibiotics were added to the growth medium as appropriate.

Plasmids. The expression vectors used in this work are essentially identical to pJU1003 (Squires et al., J. Biol. Chem. 263:16297–16302, 1988), except that sequences were inserted downstream of the translational coupler and initiation codon which code for various configurations of the following genes: mature human IGF-1 (70 aa), IGFBP-3 (264 aa), TGF-β2 (112 aa), TGF-β-receptor (extracellular domain, 136 aa), or mouse EGF-binding kallikrein (237 aa). In each case a termination codon follows these sequences. These plasmids also differ from pJU1003 in that (a) they do not contain the synthetic 16 bp adaptor sequence at the 5' end of the tet gene in pJU1003; and (b) they contain a DNA insertion at the unique PvuII site in the pBR322-derived backbone consisting of a 385 bp fragment containing the par locus of pSC101 (Meacock and Cohen, Cell 20:529–542, 1980). The plasmids also contain a gene encoding a leaderless E. coli periplasmic rotamase downstream of the foreign gene and within the same transcriptional unit. The signal sequence of the rotamase gene was deleted as described by Liu and Walsh, Proc. Natl. Acad. Sci. USA. 87:4028–4032, 1990, and replaced with an initiator methionine codon. The presence of a truncated rotamase gene neutralizes the growth inhibitory effect of ubiquitin fusions in E. coli host cells, as disclosed in co-pending application Ser. No. 08/101,506, filed 2 Aug. 1993 and entitled "Methods and DNA Expression Systems for Over-Expression of Proteins in Host Cells", now U.S. Pat. No. 5,454,051.

Each gene was prepared for expression in four separate configurations to yield the plasmids listed in Table 1: (1) with the 76 codons of yeast ubiquitin ("Ubi") inserted in-frame with and upstream of the gene sequence; (2) with the 153 codons for mature human IL-1-β ("IL1β") fused in-frame between the initiation codon and the gene, and with a linker encoding Asp-Arg-Gly-Gly (SEQ ID NO: 6) inserted between the IL-1-β sequence and the gene sequence; (3) with the 76 codons of yeast ubiquitin inserted between the linker and the gene sequence of configuration (2); and (4) with the 189 codons of mature E. coli DsbA followed by a linker encoding His-His-His-His-His-His-Ser (SEQ ID NO: 7), replacing the IL-1-β plus linker sequences of configuration (3). In addition, vectors 12886 and 12887 in which the gene is deleted and replaced with a linker (5'. . . GGATCCCGTGGAGGATTAAACCATGGAT-GCATAAGCTTCGAATTCTGCCAGGCATG-CAAGCTCAGATCC . . . 3') (SEQ ID NO: 8) are used as controls.

Six plasmids—pYZ22070, pYZ22096, pYZ9205, pYZ9206, pDM15426, and pDM15424—contain the T7 transcriptional unit of the above plasmids in a pACYC184 backbone (Chang and Cohen, J. Bacteriol. 134:1141–1156, 1978). Specifically, in these six plasmids, the ClaI-ScaI fragment carrying the T7 promoter, the translational coupler, the gene construct, the rotamase gene and the T7 terminator replaced the 1.0 kb ClaI-NruI fragment of pACYC184. The pYZ9205 plasmid contains the complete coding sequence for DsbA in the above vector backbone. The pYZ9206 plasmid is identical to pYZ9205 except that the signal sequence of DsbA has been replaced by a methionine codon. The pDM15426 plasmid is identical to pYZ22070 (above) except that it includes the signal sequence of DsbA. The pDM15424 plasmid contains the coding sequence for IL-1-receptor antagonist without its natural signal sequence.

TABLE 1

| Con-fig. | Gene | | | | |
|---|---|---|---|---|---|
| | IGF-I | IGFBP-3 | TGF-β2 | TGFR | EGFBP |
| #1 | pDJ16927 | pDJ12875 | pDJ16920 | pDJ16921 | pDJ9667 |
| #2 | pDM16963 | pDM16964 | pDM16973 | pDM16962 | pDM16972 |
| #3 | pDM16965 | pDM16967 | pDM16977 | — | pDM16976 |
| #4 | pYZ22070 | pDM15427 | pYZ22096 | pDM15428 | pDM15429 |

Yeast ubiquitin and rotamase sequences were obtained using PCR-mediated amplification from the appropriate genomic DNAs. cDNA clones for IGFBP-3 were isolated as described in Spratt et al., Growth Factors 3:63–72, 1990, and further modified by substituting the amino-terminal one-third of the gene with a synthetic DNA sequence encoding the same amino acids as the natural gene (namely, the initial 288 nucleotides of the mature sequence, up to the unique BssHII site), but using codons optimized for expression in E. coli (see, for example, Fiers, Nature 260:500, 1976). The IGF-I sequence was constructed de novo from synthetic DNA and likewise used codons optimized for E. coli.

The TGF-β2 sequence was obtained by PCR-mediated modification of a cDNA clone obtained from Dr. Michael Sporn, National Institutes of Health. The TGF-β-receptor sequence was similarly derived from pH2-3FF, a cDNA clone from Dr. Herb Lin, Massachusetts Institute of Technology, and the mouse EGF-binding kallikrein sequence from pMS2-12A, a cDNA clone from Dr. Ralph Bradshaw, University of California at Riverside. All PCR-derived DNAs were sequenced prior to use.

Each plasmid was introduced into W3110DE3 by calcium chloride-mediated transformation and selection for antibiotic resistance.

Enzymes and Reagents. Enzymes and reagents were purchased from New England Biolabs, Beverly, Mass.; Boehringer Mannheim, Indianapolis, Ind.; Sigma Chemical Co., St. Louis, Mo.; Pharmacia, Piscataway, N.J.; BRL, Gaithersburg, Md.; US Biochemical, Cleveland, Ohio; and Clontech, Palo Alto, Calif.

General Techniques. Restriction digests, agarose gel electrophoresis, ligations, transformations, DNA preparation, DNA sequencing, cell culture, SDS-PAGE, Western Blots, ELISA, and other common molecular biological techniques are described in Maniatis et al., *Molecular Cloning: A Laboratory Manual*, 2d ed., Vols. 1–3, ed. by Sambrook et al., Cold Spring Harbor Laboratory Press, 1989 and *Current Protocols in Molecular Biology*, ed. F. Ausubel et al., Greene Publishing and Wiley-Interscience: New York, 1987 and periodic updates.

Cell growth and harvest. *E. coli* strain W3110 DE3 containing one of the above plasmids was introduced into 5 ml Luria Broth (LB) containing tetracycline (15 µg/ml) or chloramphenicol (20 µg/ml) and grown to saturation overnight with aeration at 37° C. Two ml of fresh overnight culture was diluted into 100 ml of LB supplemented with 0.2% glucose. The culture was grown with aeration for several hours at the same temperature. The optical density of the culture was followed through early logarithmic growth until the optical density (600 nm) reached 0.4. Then a one ml aliquot was removed and the cells were harvested ("0 minutes" time point).

Isopropyl-thiogalactopyranoside (IPTG) was added to a final concentration of 0.4 mM and incubation of the culture continued for two hours. A second aliquot of cells was removed ("120 minutes" time point).

Aliquots from these time points were used to prepare "Whole Cell Lysates" (WCL) as described below. The remainder of the culture was harvested by centrifugation, then treated by (1) the "TEX buffer extraction" protocol or (2) a variant of the TEX protocol without the TEX step, the "simple sonication protocol."

TEX Buffer Extraction Protocol. Cells were resuspended in 1/10th of the original culture volume of TEX buffer (50 mM Tris-Cl, pH 8.0, 2 mM EDTA, 0.1% Triton X-100) and placed on ice for 20–60 minutes. After centrifugation in a Beckman TJ-6 centrifuge at 3,000 rpm for 15 minutes at 4° C., the supernatant ("TEX extract" or "T" in the Figures) was removed, and the cell pellet was resuspended in the same volume of TE (10 mM Tris-Cl, pH 8.0, 1 mM EDTA). Cells were disrupted by sonication using a Branson sonifier (2×30 sec bursts). In some experiments, lysis was enhanced by adding 0.2 mg/ml chicken lysozyme to the disruption buffer, although this step did not appear to be necessary. The disrupted cells were centrifuged in a Beckman TJ-6 centrifuge at 3,000 rpm for 15 min at 4° C. The supernatant ("cytoplasmic fraction", or "C" in the Figures) was removed. The pellet was washed once in TE and further resuspended in an equal volume of TE buffer ("insoluble fraction", or "I" in the Figures) for analysis.

Simple Sonication Protocol. Cells were resuspended in 1/10th of the original culture volume of TE (10 mM Tris-Cl, pH 8.0, 1 mM EDTA), and sonicated. All subsequent steps were the same as for the TEX buffer extraction protocol after sonication. However, the supernatant obtained after sonication in this protocol is referred to as the "soluble" fraction (labelled "S" in the Figures) (and represents the sum of the "TEX" and "cytoplasmic" fractions).

Whole cell extracts were prepared for electrophoresis by resuspending each whole cell aliquot removed from the culture during growth in 100 µl SDS-PAGE sample buffer and boiling for 5 minutes. "Soluble" and "insoluble" fraction samples were prepared by adding one volume of 2× sample buffer (1% SDS, 10% glycerol, 0.1% bromphenol blue) and incubating at 65° C. for 15 minutes.

Example 2: Homology Between IL-1-like Proteins

FIG. 1 shows an alignment of the sequences of five members of the IL-1-like protein family: (1) *E. coli* DsbA, (2) human IL-1-β, (3) human IL-1-α, and (4) human basic and (5) human acidic fibroblast growth factors (FGFs). To maximize the alignment, the appropriate regions of the longer members were excluded from the comparison, notably the oxidoreductase active site loop of DsbA (residues 21–35), and another large loop elsewhere in DsbA (residues 126–157).

When optimally aligned in this fashion, the various members of this group and the toxin coregulated pilus (TcpG) polypeptide, a bacterial homolog of *E. coli* DsbA from *Vibrio cholerae* (Peek and Taylor, op. cit.), exhibit the homologies to IL-1-β shown in FIG. 2. In addition to the noted homologies, several conservative substitutions may be observed at various positions in the sequences shown in FIG. 1, for example, Ile→Val, Phe→Tyr, and Asp→Glu at several positions.

Example 3: Accumulation and Preferential Release of IL-1-like Polypeptides and Fusions Thereof from Bacterial Cells Three representative members of the IL-1-like protein family were chosen to exemplify the widespread applicability of polypeptide fusions to IL-1-like polypeptides in order to achieve the accumulation and preferential release of the fusion proteins from bacterial cells: (1) human IL-1-β, (2) human IL-1-receptor antagonist (IL-1ra), and (3) *E. coli* DsbA. Mature sequences of IL-1ra and *E. coli* DsbA were expressed, i.e., their naturally encoded amino-terminal signal sequences were replaced with a single initiator methionine codon (pDM15424 and pYZ9206; p15433 is identical to pY9206, except that codons V22 to Q35 of DsbA were replaced with codons V22 to P77 of gene III from bacteriophage m13; the expected size of the mutant gene product is approximately 27 kD). For IL-1-β, the 153 codons specifying the mature protein were placed downstream of an initiator methionine codon (pDJ12151).

Figures 3A, 3B, 3C, 3D, 3E:
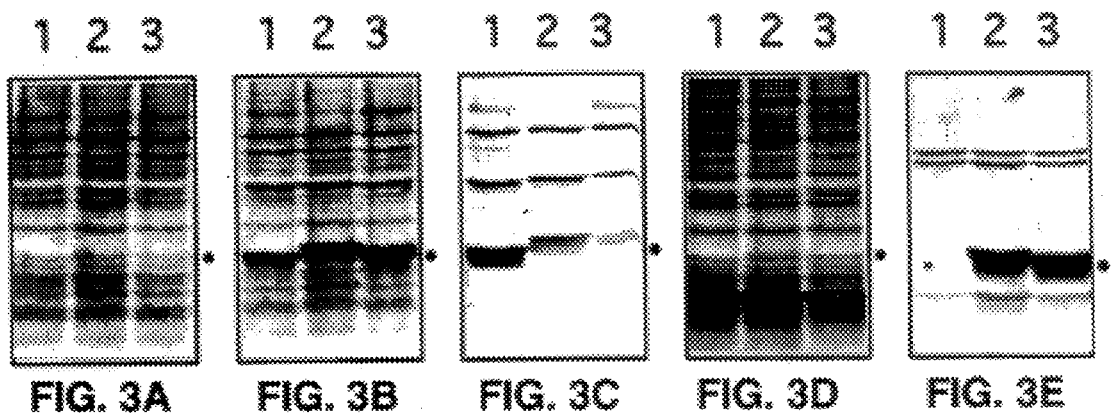
FIG. 3 shows Coomassie stained SDS-PAGE gels of fractions from E. coli cells grown at 37° C. in which IL-1-β is expressed. A: whole cell lysates ("WCL"), at time 0 (0'); B: WCL, 120 min (120'); C: TEX extract; D: "cytoplasmic" fraction; E: "insoluble" fraction. For each gel, lane 1 is wild-type IL-1β, lane 2 is IL-1β triple mutant R4A, L6A, R11G, and lane 3 is IL-1β triple mutant R4D L6A R11G. The expected size of wild-type or mutant IL-1β in each case is approximately 17 kD (●).

FIG. 3 shows the results of the fractionation by SDS-PAGE of *E. coli* cells in which IL-1-β is expressed and grown at 37° C. FIG. 3A shows whole cell lysates ("WCL") from cells at the 0 minute timepoint; FIG. 3B, WCL, 120 minutes; FIG. 3C, TEX extract; FIG. 3D, "cytoplasmic" fraction; and FIG. 3E, "insoluble" fraction. For each gel, lane 1 is wild-type IL-1β, lane 2 is IL-1β triple mutant R4A, L6A, R11G), and lane 3 is IL-1β triple mutant R4D L6A R11G. These two triple mutants are modified at residues which abolish the biological activity of IL-1-β without affecting IL-1-β binding to at least one of its natural receptors (Gehrke et al., J. Biol. Chem. 265:5922–5925, 1990; Labriola-Tomkins et al, Proc. Natl. Acad. Sci. USA. 88:11182–11186, 1991). The expected size of wild-type or mutant IL-1β in each case is approximately 17 kD (indicated with a ● to the right of each gel).

These gels indicate that the majority of the expressed wild-type IL-1-β (lane 1 of FIGS. 3A–E) was found in the TEX fraction, demonstrating that IL-1-β was sequestered to a non-cytoplasmic location in vivo. This was not the case with the two triple mutants (R4A L6A R11G, lane 2; and R4D L6A R11G, lane 3). The majority of the expressed IL-1-β from these mutants was found in the "insoluble" fraction. These data indicate that even subtle modifications affect the ability of IL-1-β to accumulate in a noncytoplasmic, soluble form.

The data in Table 2 (below) confirm these results, showing that an IL-1-β-IGF fusion, like IL-1-β itself, is found almost exclusively in the TEX fraction, along with beta-lactamase, a periplasmic protein. Only a small percentage of the IL-1-β-IGF fusion protein co-localizes with beta-galactosidase, a cytoplasmic marker.

Figures 4A, 4B, 4C, 4D:
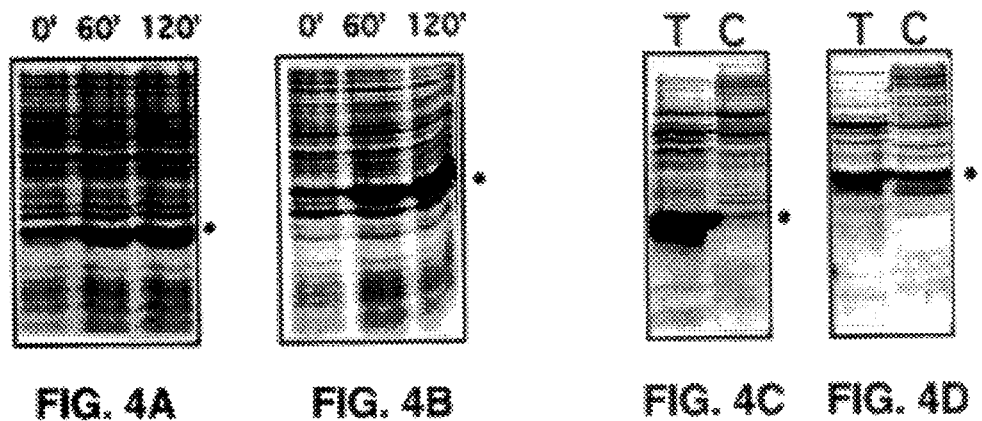
FIG. 4 shows SDS-PAGE of fractions from E. coli cells expressing E. coli DsbA. (a) WCL at 0', 60', and 120' from cells expressing mature DsbA; (b) WCL at 0', 60', and 120' from cells expressing "mutant" DsbA; (c) TEX extract ("T") and "cytoplasmic" ("C") fractions from cells expressing mature DsbA; (d) "T" and "C" fractions from cells expressing "mutant" DsbA. The expected size of the expressed polypeptide is approximately 22 kD (●).

FIG. 4 shows the accumulation and SDS-PAGE fractionation of E. coli DsbA. FIG. 4a shows whole cell lysates ("WCL") at 0, 60, and 120 minute timepoints from cells expressing mature DsbA (i.e., lacking a leader sequence); FIG. 4b, WCL at 0, 60, and 120 minute timepoints from cells expressing a "mutant" mature DsbA with a replacement of the active site loop by approximately 55 amino acids from gene III of bacteriophage m13 (codons V22 to Q35 of DsbA were replaced with codons V22 to P77 of m13 gene III); FIG. 4c, TEX extract ("T") and "cytoplasmic" ("C") fractions from cells expressing wild-type mature DsbA; and FIG. 4d, "T" and "C" fractions from cells expressing "mutant" DsbA. The expected size of the expressed polypeptide is approximately 22 kD.

Again, virtually all the expressed DsbA protein was found in the TEX fraction. The ability to transfer to an extractable compartment was not lost when the "active" site loop of DsbA was replaced by sequences from an unrelated gene.

Figures 5A, 5B, 5C, 5D, 5E, 5F, 5G, 5H:
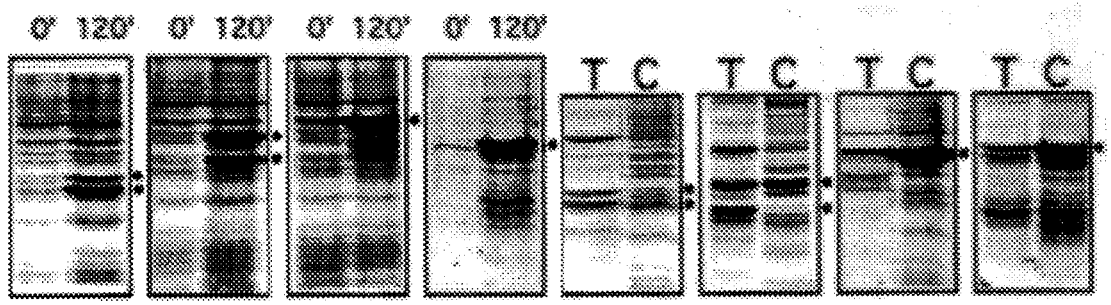
FIG. 5 shows SDS-PAGE gels of fractions from E. coli cells in which various fusions of IL-1-like proteins with human IGF-I or the soluble extracellular domain of the Type II TGF-β receptor were expressed. Left: WCL at 0' and 120' for (1) IL1β-IGF (pDM16963), expected size approximately 24–25 kD; (2) IL1β-Ubi-IGF (pDM16965), expected size approximately 32 kD (●); (3) DsbA-Ubi-IGF (pYZ22070), expected size approximately 37 kD (●); and (4) DsbA-Ubi-TGFR (pDM15428), expected size approximately 46 kD (●). Right: TEX and "cytoplasmic" ("CYT") fractions for the four fusion polypeptides. Where there are two dots, the lower dot represents a lower molecular weight breakdown product of the larger polypeptide.

FIG. 5 shows the fractionation of cells in which various fusions of IL-1-like proteins with human IGF-I or TGF-β receptor were expressed: (1) IL1β-IGF (pDM16963), with an expected size of approximately 24–25 kD); (2) IL1β-Ubi-IGF (pDM16965), with an expected size of approximately 32 kD; (3) DsbA-Ubi-IGF (pYZ22070), with an expected size of approximately 37 kD; and (4) DsbA-Ubi-TGFR (pDM15428), with an expected size of approximately 46 kD.

The four SDS-PAGE gels in FIG. 5, left, show WCL at 0 and 120 minute timepoints of E. coli cells expressing these four fusion polypeptides. The four SDS-PAGE gels in FIG. 5, right, show TEX and "cytoplasmic" fractions for these four fusion polypeptides. Dots are used to denote the band of the fusion polypeptide and when there is a second dot present, the presence of a breakdown product of the fusion polypeptide.

In all four cases substantial proportions of the fusion proteins were found in the TEX fraction. Thus, these fusions of IL-1-like proteins from cells also substantially transferred to the extractable compartment.

Figure 6A:
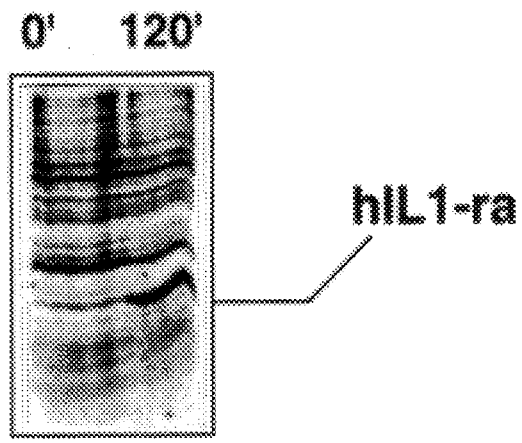
FIG. 6 shows SDS-PAGE of fractions from E. coli cells expressing human IL-1-receptor antagonist with its natural signal sequence deleted (pDM15424). Left: WCL at 0' and 120'; right, TEX ("T") and "cytoplasmic" ("C") fractions ("FXN"). The expected product has a size of approximately 18 kD.
Figure 6B:
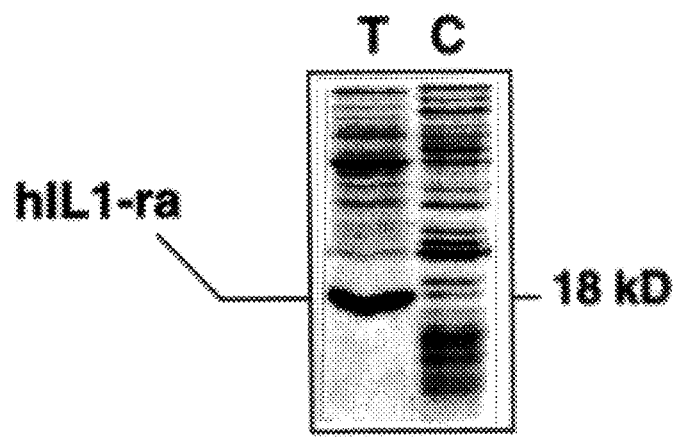

FIG. 6 shows whole cell lysates ("WCL") at 0 and 120 minute timepoints and TEX ("T") and "cytoplasmic" ("C") fractions ("FXN") of human IL-1-receptor antagonist expressed in E. coli with its natural leader sequence deleted (pDM15424). Again, most of the protein was found in the TEX fraction. This result indicates that IL-1-ra lacking a leader sequence is properly secreted.

Table 2 (below) shows that the TEX fractions of E. coli cells expressing IL-1-β or an IL-1-β-IGF fusion contained a periplasmic enzyme marker, β-lactamase, but not a cytoplasmic marker, β-galactosidase. In the same samples, IL-1 immunoreactivity (signifying the presence of the fusion protein) was found almost exclusively in the TEX fraction.

TABLE 2

| | Percent of Total Cell Activity | | | |
|---|---|---|---|---|
| | pDJ12151 (IL-1-β) | | pDM16963 (IL-1-β-IGF) | |
| Assay | TEX | CYT | TEX | CYT |
| Beta-lactamase | 96.4 | 3.6 | 96.1 | 3.9 |
| Beta-galactosidase | 2.3 | 97.7 | 6.5 | 93.5 |
| Interleukin-1-β | 94.1 | 5.9 | 93.2 | 6.8 |

To confirm a similar localization with mature DsbA, oxidoreductase assays were performed on crude extracts as described by Holmgren (J. Biol. Chem. 254:9627–9632, 1979), except for the following modifications: Assays were performed at room temperature; DTT was at 0.1 mM; and insulin substrate was at 1 mg/ml. The results are provided in Table 3. Like IL-1-ra, DsbA lacking a leader sequence is secreted, resulting in its localization in the TEX fraction.

TABLE 3

| Oxidoreductase Activity of DsbA | | | |
|---|---|---|---|
| Leader Sequence | Fraction | Activity (U/min-mg) | Percent Total Cell Activity |
| + | T | 0.089 | 87.3 |
| + | C | 0.013 | 12.7 |
| − | T | 0.100 | 89.3 |
| − | C | 0.012 | 10.7 |

T = TEX fraction;
C = cytoplasmic fraction

Example 4: Accumulation of Soluble Fusion Polypeptides in Bacteria

IL-1-like fusion partners conferred a pronounced and salutary effect on the solubility of a variety of structurally unrelated heterologous proteins expressed in bacteria.

FIGS. 7 through 10 summarize the results obtained when the "soluble" (S) and "insoluble" (I) fractions of induced cells carrying constructs for each of four different human genes were compared.

In FIG. 7, TGF-β2 fusion constructs were analyzed. FIG. 7, left, shows Coomassie-stained SDS-polyacrylamide gels of whole cell lysates ("WCL") from 0 and 120 minute timepoints and soluble ("S") and insoluble ("I") fractions from E. coli cells which are transformed with pDJ16920, which encodes a ubiquitin-TGF-β2 fusion polypeptide with an expected size of approximately 20 kD. Virtually all of this fusion polypeptide was found in the "insoluble" fraction. However, with plasmid pYZ22096 encoding a DsbA-ubiquitin-TGF-β2 fusion of approximately 42 kD, FIG. 7, right, shows the protein was almost entirely soluble. These results are also significant in that they show that soluble TGF-β2 may be obtained at 37° C. Previous attempts to obtain soluble TGF-β2 relied on low temperature growth (e.g., at 30° C.), which is less desirable since lower temperature growth is suboptimal for growth of E. coli host cells and requires expensive reactor cooling.

In FIG. 8 the results obtained with several IGF-I fusions are displayed. FIG. 8, left, shows Coomassie-stained SDS-polyacrylamide gels of whole cell lysates ("WCL") from 0 and 120 minute timepoints and soluble ("S") and insoluble ("I") fractions from E. coli cells transformed with pDJ16927 and pDM16965. pDJ16927 expresses a ubiquitin-IGF fusion with an expected size of approximately 15 kD. pDM16965 expresses IL1β-ubiquitin-IGF with an expected size of approximately 32 kD.

FIG. 8, right, shows similar gels of extracts of E. coli cells transformed with pYZ22070, which expresses mature DsbA-ubiquitin-IGF (i.e., DsbA lacking a signal sequence) with an expected size of approximately 37 kD, or with pDM15426, which expresses DsbA-Ubi-IGF in which DsbA retains its native signal sequence and has an expected size of approximately 37 kD.

Figure 9A:
FIG. 9 shows SDS-PAGE gels of fractions of E. coli cells expressing fusions to IGFBP-3. Panel [i]: WCL at 0' and 120' and "soluble" ("S") and "insoluble" ("T") extracts of E. coli cells expressing pDJ12875, which encodes a ubiquitin-IGFBP-3 fusion having an expected size approximately 38 kD; panel [ii], IL-1-ubiquitin-IGFBP-3 having an expected size of approximately 55 kD (pDM16967); and [iii], DsbA-ubiquitin-IGFBP-3 having an expected size of approximately 60 kD (pDM15427).
Figure 9B:
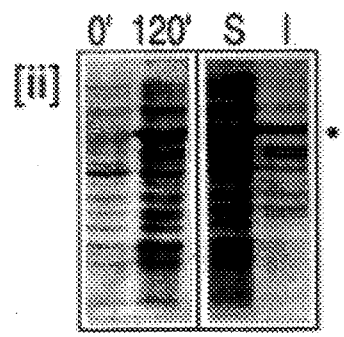
Figure 9C:
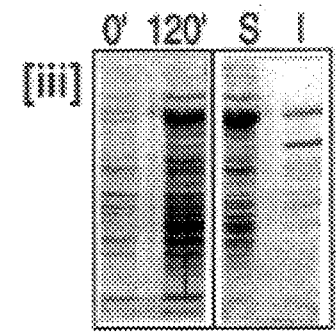

FIG. 9 shows the results obtained with fusions to IGFBP-3. Panel [i] shows the ubiquitin-IGFBP-3 fusion, with an expected size of approximately 38 kD (pDJ12875); panel [ii], IL1-ubiquitin-IGFBP3, with an expected size of approximately 55 kD (pDM16967); and [iii], DsbA-ubiquitin-IGFBP-3, with an expected size of approximately 60 kD (pDM15427). Solubility was markedly higher for the fusion to IL-1.

Figure 10A:
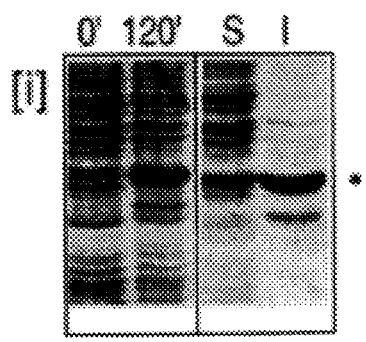
FIG. 10, panel [i], shows SDS-PAGE gels of WCL at 0' and 120' and "soluble" ("S") and "insoluble" ("T") fractions from E. coli cells expressing a ubiquitin-TGF-βR fusion with an expected size of approximately 24 kD (pDJ16921); panel [ii], a DsbA-ubiquitin-TGF-βR fusion with an expected size of approximately 46 kD (pDM15428).
Figure 10B:
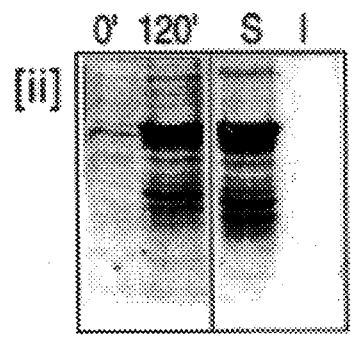

FIG. 10, panel [i], shows whole cell lysates from 0 and 120 minute timepoints and "soluble" ("S") and "insoluble" ("I") fractions from E. coli cells expressing a ubiquitin-TGF-βR fusion with an expected size of approximately 24 kD (pDJ16921), panel [ii], a DsbA-ubiquitin-TGF-βR fusion with an expected size of approximately 46 kD (pDM15428; βR is the extracellular domain of the TGF-β receptor). The ubiquitin-TGF-βR fusion was largely insoluble. In marked contrast, the DsbA-ubiquitin-TGF-βR fusion was virtually completely soluble.

Example 5: Biological Activity of Human IGF-I Obtained from Fusion Proteins in Bacterial Cells grown at 37° C.

FIG. 11 shows the effects of temperature and of fusion to DsbA polypeptide on the in vivo folding of IGF-I into a biologically active conformation.

The fusion proteins were purified from extracts of these cultures by passing "soluble" fractions prepared from 100 ml of induced cells as described above ("simple sonication protocol") over a Q-Sepharose (Pharmacia) column (5 ml bed volume) equilibrated in 50 mM Tris-Cl, pH 8.0, 1 mM EDTA. The column was washed in two column volumes of the same buffer, and the sample was eluted in 8 ml of the same buffer with an additional 0.4M NaCl. The eluate was concentrated on a Centricon-30 membrane (Amicon) to a volume of 0.5 ml.

Ubiquitin Hydrolase Cleavage. To the above concentrate was added 10μl of crude extract of ubiquitin hydrolase enzyme, which was prepared from a strain containing plasmid 23344 as described below in Example 6.

HPLC-reverse Phase Chromatography. HPLC-reverse phase chromatography was performed as follows. After incubation with ubiquitin hydrolase for 60 minutes at 37° C., the digest was directly applied to a C-18 (Vydac) reverse phase column and subjected to HPLC chromatography in a two-buffer system: Buffer A was aqueous 0.1% trifluoroacetic acid (TFA) and Buffer B was 0.1% TFA in acetonitrile. The column was developed as follows: 0–22% B in 4 minutes; wash in 22% B for 6 minutes; elute in a 22–42% B gradient at 0.5% per minute (40 minutes total). The IGF-I standard elutes at 31.4% B under these conditions. Peaks were collected, then diluted for the IGF bioassay (below), or subjected to PAGE analysis. The peak collected from the 31.4% position in all samples contained a single protein band migrating at 7.5 kD as determined by PAGE, with the protein band visualized by silver staining. No contaminating proteins were observed in this fraction. Peak heights were therefore used to estimate the amount of IGF present by comparison with a commercial IGF standard.

IGF Bioassay. In the IGF bioassay, MG63 cells (ATCC CRL #1427, a male osteosarcoma cell line) were plated in 96-well microtiter plates at 5000 cells per well and incubated for 16 hours at 37° C. in a $CO_2$ incubator. The culture medium was aspirated and samples (including commercial IGF standards, such as are available from Imcera, Terre Haute, Ind.) were added to the wells in RPMI medium, 2 mM glutamine, 50 U/ml penicillin, 50 mcg/ml streptomycin, 0.05% bovine serum albumin (BSA).

Serial two-fold dilutions of each sample were tested. Using Cell Proliferation Kit (catalog no. RPN.210, Amersham) cells were incubated for 24 hours at 37° C., the medium was decanted, and 100 μl of the kit's labelling reagent was diluted as directed in the same medium and was added to each well. The plates were then incubated at 37° C. for three hours.

After the reagent was decanted, the cells were washed in cold PBS three times then fixed by the addition of 100 μl 90% ethanol, 5% acetic acid to each well. The fixed cells were incubated for 30 minutes at room temperature, then washed three times each in (a) PBS+0.1% Tween-20; (b) PBS+0.1% Triton X-100, and (c) PBS+0.1% Tween-20. Subsequently, the wells were blocked for 15 minutes at room temperature in PBS+0.1% Tween-20+1% nonfat dry milk (NFDM, Carnation brand) and treated with the antibody label provided in the kit according to the manufacturer's protocol (Amersham). The $A_{405}/A_{490}$ ratio was measured in order to determine 5-bromo-2-dioxyuridine (BRDU) incorporation. The concentration of IGF-I in each sample was determined by comparison with a standard curve. All samples were assayed in triplicate.

Following the binding reaction, samples were chemically cross-linked by addition of 0.3 mM disuccinimidyl suberate at 4° C. for 30 minutes. Crosslinking was terminated by adding Tris-HCl, pH 7.5, to a concentration of 20 mM, followed by boiling for 10 minutes. A portion of the cross-linked sample was enzymatically deglycosylated by incubation with N-glycosidase F at 37° C. for three hours in the presence of 0.2% 2-mercaptoethanol and 2% SDS. Following this incubation, a second aliquot of N-glycosidase F was added, and the sample was incubated further for one hour. The products of the binding reaction were separated by SDS-PAGE under reducing conditions using a 8% gel. The labeled species were visualized after fixation of the gel in 10% acetic acid, 40% methanol by autoradiography.

Figure 11A:
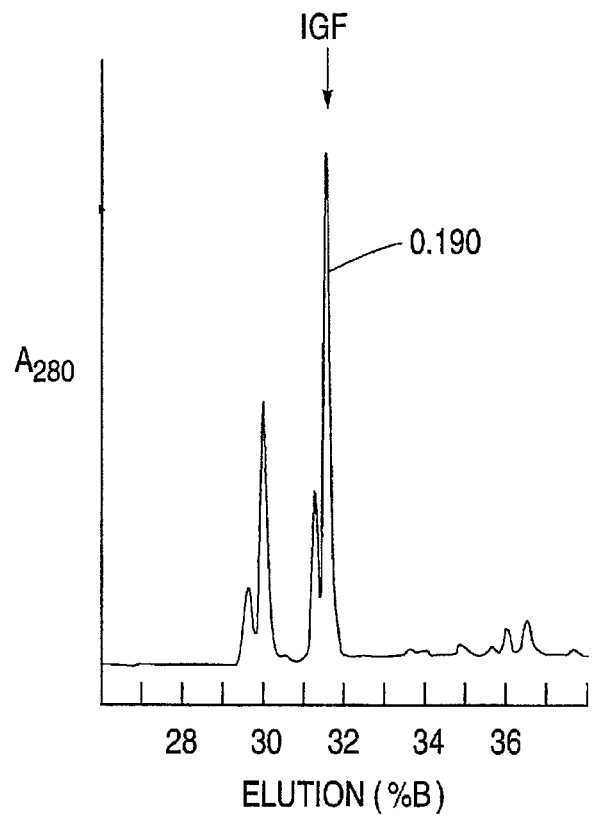
FIG. 11A and B: HPLC-reverse phase elution profiles from ubiquitin hydrolase-cleaved IGF-I derived from cultures of DsbA-ubiquitin-IGF and ubiquitin-IGF constructs, respectively, grown at 30° C. C and D: ubiquitin hydrolase-cleaved DsbA-ubiquitin-IGF and ubiquitin-IGF, respectively, grown at 37° C. The specific activity of the IGF peaks is shown as boxed values, arbitrary units).
Figure 11B:
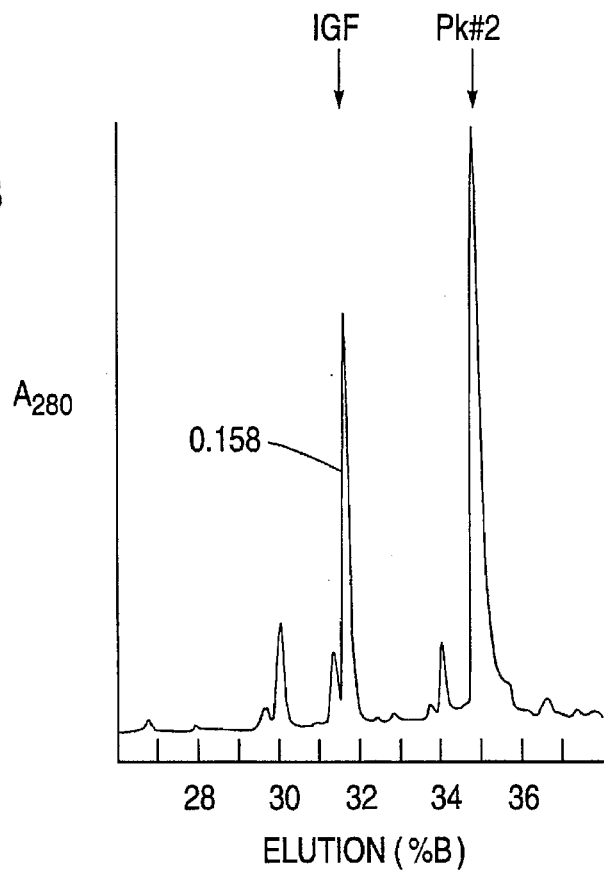
Figure 11C:
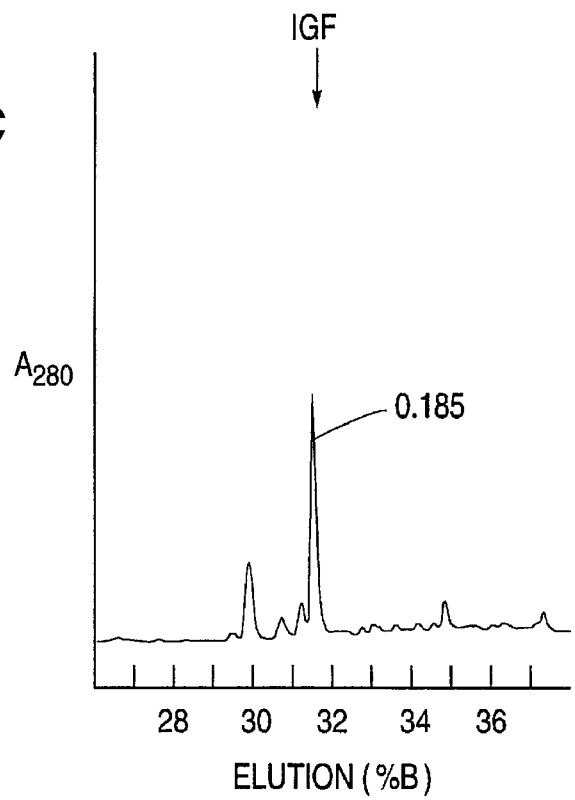
Figure 11D:
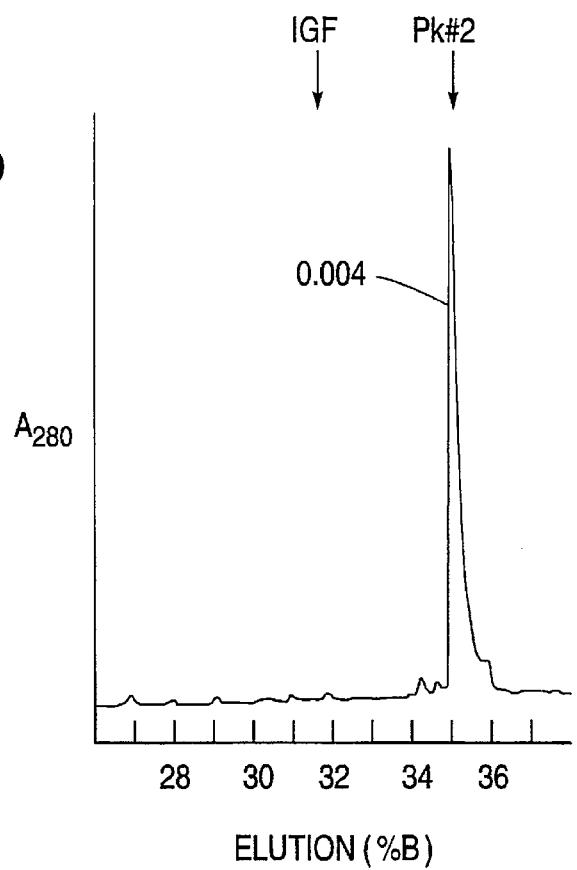

FIG. 11A and 11B show HPLC-reverse phase elution profiles from ubiquitin hydrolase-cleaved IGF-I derived from cultures of DsbA-ubiquitin-IGF and ubiquitin-IGF constructs, respectively, grown at 30° C. FIGS. 11C and 11D show the corresponding data from cultures of DsbA-ubiquitin-IGF and ubiquitin-IGF constructs, respectively, grown at 37° C. The position of IGF-I at 31.4% buffer B was established by comparison with a commercial purified IGF standard. It is clear in FIG. 11D that at 37° C. the ubiquitin fusion did not produce properly folded IGF-I (IGF-I is at about 35% B), but the ubiquitin fusion produced properly folded IGF-I at 30° C. Although the temperature dependence of IGF-I folding per se was not unexpected, the marked effect of a DsbA fusion partner on the recovery of properly folded IGF-I was surprising (compare FIGS. 11C and 11D).

The specific activity of the IGF peaks (shown in FIG. 11 as boxed values, arbitrary units) was established by the IGF bioassay. In this assay the specific activity of authentic IGF-I was 0.206. In contrast, the specific activity of peak #2, the major peak in FIG. 11D (ubiquitin fusion, 37° C.), was 0.004.

The amino-terminal protein sequence for the IGF-I peak in FIG. 11C was established by Edman degradation in an automated sequencer (Applied BioSystems, Foster City, Calif.). A single major species was recovered with the sequence Gly-Pro-Glu-Thr-Leu-X-Gly-Ala-Glu-Leu (SEQ ID NO: 9). This was the expected amino terminal sequence for mature IGF-I and shows, additionally, that ubiquitin hydrolase cleaved as precisely as expected.

To exclude the unlikely possibility that the purification of the IGF-I sample prior to HPLC might have influenced the results, crude extracts ("soluble" fraction) from strains carrying the constructs listed in Table 4 were treated with ubiquitin hydrolase, adjusted for total protein concentration and diluted for the IGF bioassay. Cleavage of the fusion protein was confirmed by SDS-PAGE in each case. The crude bioactivities (in arbitrary units) were:

TABLE 4

Bioactivity of DsbA Fusion Proteins Cleaved With Ubiquitin Hydrolase

| CONSTRUCT | FUSION | BIOACTIVITY |
|---|---|---|
| pDM16927 | Ubiquitin-IGF | 0.113 ± 0.009 |
| pDM15422 | (SS−) DsbA-ubiquitin-IGF | 0.368 ± 0.030 |
| pDM15426 | (SS+) DsbA-ubiquitin-IGF | 0.242 ± 0.018 |

These results confirmed the earlier observation that a DsbA fusion partner substantially increases the recovery of biologically active IGF-I from E. coli. Bioactive IGF-I was also obtained and analyzed in a similar fashion from fusions containing IL-1-β in place of DsbA. The IGF-I-DsbA fusions obtained also displayed the correct amino-terminal sequence (GPETLXGA . . . ) (SEQ ID NO: 10) after cleavage with ubiquitin hydrolase.

Taken together, these results demonstrate the utility of IL-1-like fusion partners in the production, accumulation and recovery of biologically active IGF-I in bacterial cells.

Example 6: Production of Yeast Ubiquitin Hydrolase in Bacterial Cells and Co-expression of Fusion Polypeptides Ubiquitin hydrolase (UH) expression vectors were derived from a cDNA clone of UBP-1 (Tobias and Varshavsky, J. Biol. Chem. 266:12021–12028, 1991) by deleting the amino-terminal 92 codons of the gene upstream of the unique BglII site and replacing this DNA with (a) the first 12 codons of the phi-10 gene of bacteriophage T7, to yield plasmid 23344; (b) the 153 codons of mature human IL-1-β, followed by a linker encoding Asp-Arg-Gly-Asp-Pro-His-His-His-His-His-His-Glu (SEQ ID NO: 11), to produce plasmid 23399; or (c) the 189 codons of E. coli DsbA, followed by a linker encoding His-His-His-His-His-His-Ser (SEQ ID NO: 72), followed by the first 75 codons (after methionine) of yeast ubiquitin, followed by a linker encoding Asp-Pro-His-His-His-His-His-His-Glu (SEQ ID NO: 12), to yield plasmid 27246. In each case, the in-frame fusions resulted in a fusion gene under the control of the T7 promoter. The vector backbone and other details of the transcriptional unit used in these experiments are described in Example 1.

Cells of E. coli strain W3110 DE3 were transformed with combinations of compatible plasmids as follows:

TABLE 5

In vivo cleavage of IGF fusions by Ubiquitin Hydrolase (UH)

| STRAIN | PLASMIDS | DESCRIPTION | RESULTS |
|---|---|---|---|
| #1 | 23999 + 15426 | IL-1-UH + (SS+)DsbA-ubi-IGF | Minimal cleavage of IGF fusion |
| #2 | 27246 + 15426 | DsbA-ubi-UH + (SS+)DsbA-ubi-IGF | No cleavage |
| #3 | 27246 + 22070 | DsbA-ubi-UH + (SS−)DsbA-ubi-IGF | Cleavage virtually complete |
| #4 | 23344 + 15422 | phi 10-UH + (SS−)DsbA-ubi-IGF | Cleavage virtually complete |

After induction with IPTG as described in Example 1, major bands appeared on Coomassie-stained SDS-polyacrylamide gels which corresponded to the expected sizes of IGF fusion protein and the product of its cleavage with UH.

The results shown in Table 5 clearly demonstrate that a protein fusion targeted to the periplasmic space via the general secretion pathway is relatively immune to cleavage by UH enzyme fused to either IL-1-β or DsbA, but the identical fusion protein sequestered via the alternative pathway used by mature DsbA (i.e., lacking a signal sequence) is effectively cleaved by either cytoplasmic or DsbA-fused UH enzyme. Despite the selective extraction observed for IL-1-like polypeptides and their fusions when expressed in E. coli (Example 3), these polypeptides appear to be sequestered in a manner that is different from that of classical periplasmic proteins. These results also show that co-expressed ubiquitin hydrolase genes can efficiently cleave in vivo a fusion polypeptide comprising an IL-1-like polypeptide separated from a polypeptide of interest, such as IGF, by a linker containing a ubiquitin hydrolase cleavage site.

Example 7: Purification of TGF Receptor Fragment and Cross-linking Assay

The "soluble" fraction prepared from induced cells (100 ml culture volume) containing plasmid pDM15428 was passed over a 1 ml bed volume Ni-NTA affinity column (QIAGEN Inc., Chatsworth, Calif.), equilibrated, washed and developed according to the manufacturer's recommendations. The eluate was dialysed against the original loading buffer, digested with a partially pure preparation of ubiquitin hydrolase, and passed over an Ni-NTA column identical to that described above. The pass-through was concentrated on a Centricon-10 membrane (Amicon) to a final volume of 0.5 ml. and used for crosslinking assays as follows: 20 µl of this sample was incubated overnight with 100 pM $^{125}$I-TGF-β1 (250 nM). The sample was cross-linked with 0.3 mM disuccinimidyl suberate (Pierce Chemical, Rockford, Ill.) for 15 minutes at 4° C. The reaction was quenched by the addition of one-third volume of 4× Laemmli gel sample buffer containing 50 mM dithiothreitol. The sample was boiled for two minutes (100° C.) and subjected to SDS-PAGE. The gel was dried and visualized by autoradiography with overnight exposure at −80° C.

Figure 12:
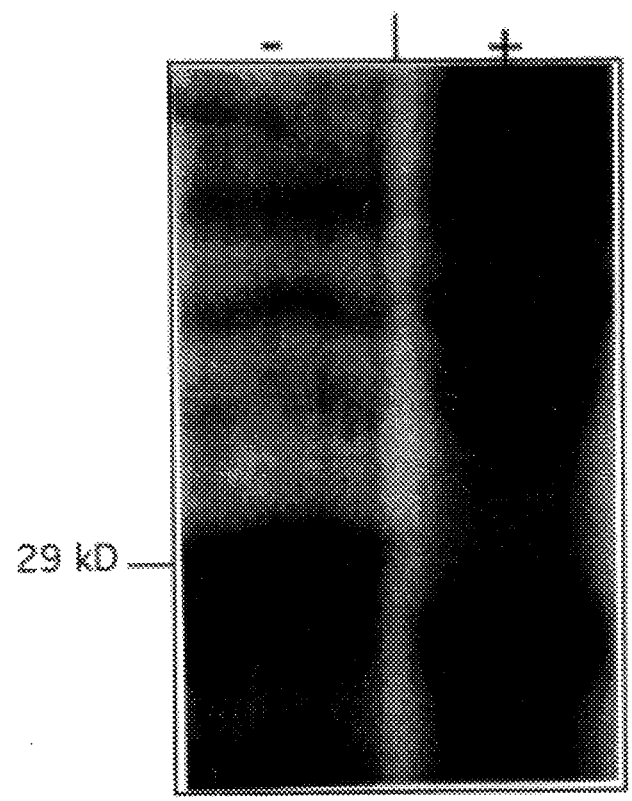
FIG. 12 shows SDS-PAGE gels of partially purified TGF-βR (136 amino acid extracellular domain, pDM15428) cross-linked with $^{125}$I-radiolabeled TGF-β1. The size of the expected cross-linked product is approximately 30 kD. Left (−): no added cold TGF-β1. Right (+): excess cold TGF-β1 (2500-fold molar).

FIG. 12 shows the result of crosslinking experiments using $^{125}$I-radiolabeled TGF-β1 and partially purified TGF-βR (136 amino acid extracellular domain). The expected crosslinked product is observed migrating at about 30 kD.

This product is formed by a specific binding interaction, because its appearance is completely abolished by the addition of (1000-fold molar) excess cold TGF-β1. These data show that with the aid of an IL-1-like fusion partner, functional TGF-β receptor can be produced in bacteria.

Example 8: IGFBP-3 Dot Blot Assay

For the IGFBP-3 dot blot assay, pre-cut Immobilon-P membrane (Millipore) was soaked in methanol for 5 seconds, rinsed with Tris-buffered saline (TBS), and then soaked in TBS for 10 minutes. The membrane was mounted on a dot blot apparatus and 50 µl TBS was applied to each well. The samples were applied to the membrane by vacuum suction. The membrane was then blocked in TBS+3% non-fat dry milk (CARNATION brand) at room temperature for two hours. $^{125}$I-radiolabelled IGF-I (1 µl per ml blocking buffer) was added, followed by incubation at room temperature for two hours. The buffer was discarded and the filter washed in TBS (2×15 minute washes at room temperature). The membrane was then air dried for ten minutes then exposed to Kodak XR-Omat film overnight at −80° C.

Figures 13A, 13B:
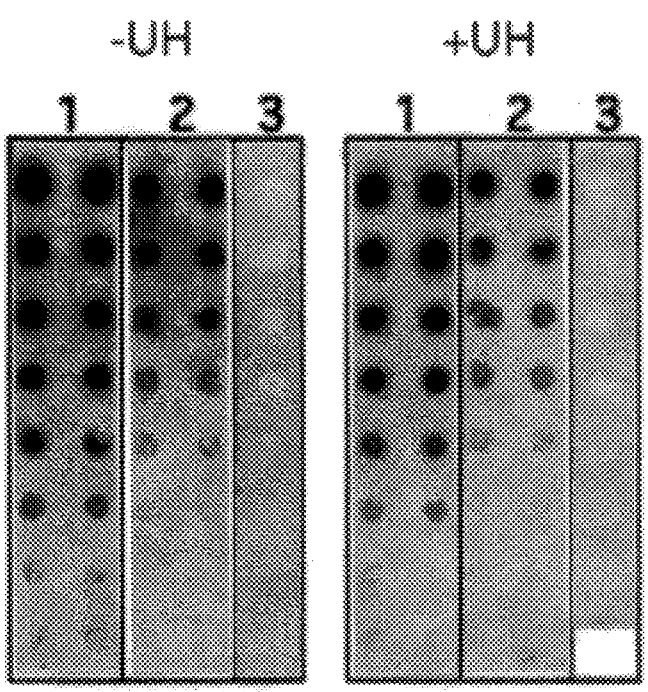
FIG. 13 shows results of dot-blot assays using $^{125}$I-radiolabeled IGF-I to measure binding activity in crude extracts ("soluble" fraction) of E. coli cells expressing (1) pDM15427, which encodes a DsbA-ubiquitin-IGFBP-3 fusion; (2) pDJ12875, which encodes a ubiquitin-IGFBP-3 fusion; or (3) pDJ12887, a "vector only" control. Samples were untreated (−UH) or cleaved with ubiquitin hydrolase (+UH).

FIG. 13 shows the results of a dot-blot binding assay using $^{125}$I-radiolabeled IGF-I to measure binding activity in crude extracts ("soluble" fraction) of strains expressing (1) a DsbA-ubiquitin-IGFBP-3 fusion (pDM15427), (2) a ubiquitin-IGFBP-3 fusion (pDJ12875), or (3) a "vector only" control (pDJ12887). Similar results were obtained whether the samples were pretreated with ubiquitin hydrolase (+UH) or were not treated (−UH), indicating that the intact fusion proteins can bind the ligand as efficiently as the cleaved IGFBP-3 protein. In this case, no ubiquitin cleavage is necessary to obtain an active protein.

The results clearly show that the DsbA fusion partner increases the recovery of bioactive IGFBP-3 by about 16-fold (4-fold serial dilutions are used on the blot).

Example 9: Expression of IL-1-β-IGFBP-3 Fusion Protein in Mammalian Cells

Expression plasmid pDM15430, which encodes an IL-1-β-IGFBP3 fusion protein in mammalian cells, was constructed by inserting a fusion sequence from plasmid pDM16964 into pDJ12147, a deletion derivative of pRc-CMV (InVitrogen Corp, La Jolla, Calif.) which utilizes a human cytomegalovirus promoter and enhancer and bovine growth hormone polyadenylation signal. The fusion sequence from plasmic pDM16964 comprises codons for an initiator methionine, the 153 amino acids of mature human IL-1-β and the 264 amino acids of mature human IGFBP-3.

This construct and the corresponding non-recombinant plasmid ("vector") were used to transiently transfect COS-M6 cells using the DEAE-dextran method (Seed and Aruffo, Proc. Natl. Acad. Sci. USA 84:3365–3369, 1987). Cell extracts were made 72 hours after transfection by lysing the cell layer with phosphate buffered saline (PBS) containing 0.2% NP-40 at 4° C. for 30 minutes. The extract was centrifuged to remove insoluble debris, and the supernatant was used for binding assays.

Figure 14:
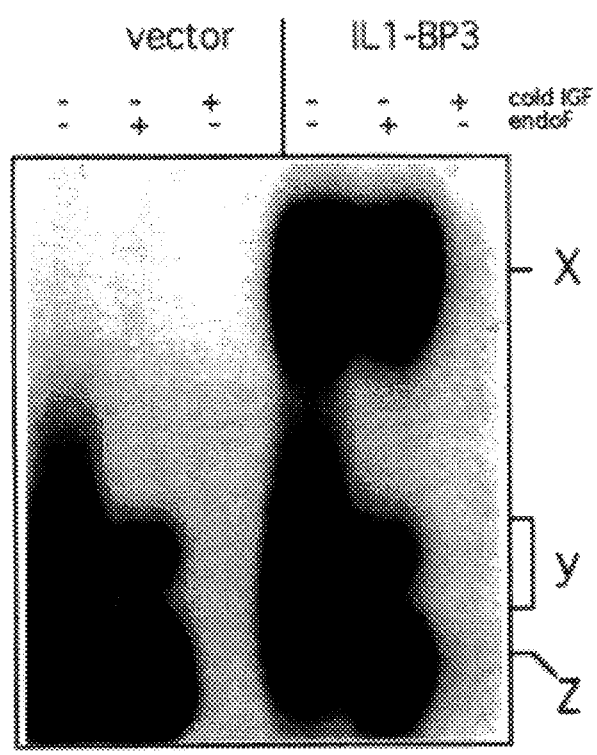
FIG. 14 shows SDS-PAGE gels of cross-linked samples from COS cells transiently transfected pDM15430, which encodes IL-1-β-IGFBP-3 ("IL1-BP3") or the vector alone ("vector"), with (+) or without (−) treatment of the crosslinked sample with endoglycosidase F, and with or without competition with "cold" IGF. On the right side of the figure are labels for the 55 kD fusion polypeptide (X), a native, glycosylated IGF binding protein (Y) and the native, deglycosylated IGF binding protein (Z).

FIG. 14 shows that endogenous IGF-binding activity was found in COS cell extracts in a broad band in the 45–50 kD size range (Y). FIG. 14, right, shows SDS-PAGE of crosslinked samples from COS cells transiently transfected as described above with pDM15430, which encodes IL1β-IGFBP3 ("IL1-BP3"). FIG. 14, left, shows SDS-PAGE of cross-linked samples from COS cells transfected with the vector, alone ("vector"). Each set of gels has a left lane with no endoglycosidase F treatment or "cold" IGF competition. The middle lane shows results after treatment with endoglycosidase F, and the right lane shows the results of competition with an excess of "cold" IGF. After treatment of the crosslinked sample with endoglycosidase F as described above, the endogenous IGF binding band was reduced to a sharper band migrating at about 40 kD. In cells transfected with an IL-1-β-IGFBP-3 fusion construct, a crosslinked band in the expected size range (approximately 55 kD+, "X" in FIG. 14) was observed. However, treatment with endoglycosidase F did not alter the mobility of the X band. This demonstrates that the IL1β-IGFBP-3 fusion protein that accumulated in these cells was not glycosylated. All of the binding observed was specific, as it was successfully competed away with cold IGF (see right lanes of FIG. 14).

In parallel experiments, cells transfected with Met-IGFBP-3 constructs lacking the IL-1 fusion partner did not show any detectable IGF binding by the above criteria (data not shown). Other experiments have shown that the natural form of the IGFBP-3 gene (i.e., with its own signal sequence) produces a glycosylated product in mammalian cells (Spratt et al., *Growth Factors* 3:63–72, 1990). Thus, the IL-1 fusion of the present example is likely to be sequestered in the mammalian cell (as is IL-1-β itself), but not by virtue of passage through the ER and Golgi, the normal route taken by secreted proteins which would result in glycosylation of the IGFBP-3 protein.

Example 10: Expression of Leader-deleted DsbC, Mutants and Fusions

A recently identified member of the Dsb family of proteins in *E. coli*, DsbC, bears no obvious primary sequence homology to other previously-described oxidoreductases. This gene had been earlier named xprA (Missiakas et al., *EMBO J.* 13:2013–2020, 1994; Lovett and Kolodner, *J.Bacteriol.* 173:353–364, 1991). A leader-deleted version of this gene was cloned into a T7 expression vector which has been described (see, for instance, pYZ22070 in Example 1, above) by PCR using *E. coli* DNA as the template and the primers 5' . . . GGTGGATCC GATCGTGGAGGATGAT-TAAATGGCTGATGACGCGGCAATTCAACAAAC . . . 3' (SEQ ID NO: 13) and 5' . . . GGGAAGCTTACTCGAG-CATGCTACCACCAGATTTACCGCTGGTCA TTTTTTGG . . . 3'(SEQ ID NO: 14). The resulting plasmid, pDM25492, was further modified as follows: The DNA sequence surrounding the presumed double cysteine active site loop was changed from 5' . . . ACCTGTGGTTACTGC-CACAAA . . . 3' (SEQ ID NO: 15) to 5' . . . ACCGG-TAGCGGTTCTGGTAAA . . . 3' (SEQ ID NO: 16) using methods of site-directed mutagenesis well known to those skilled in the art. The resulting plasmid was named pDM46805. Fusions of leader-deleted DsbC (with or without the double cysteine active site loop) to IGF-I were constructed to produce plasmids pDM15486 and pDM46806, respectively.

The DNA sequences of the leader-deleted DsbC variants present in these four plasmids, pDM15486, pDM25492, pDM46805 and pDM46806, are listed in FIGS. 32, 33, 25, 31, respectively.

Figures 15A, 15B, 15C, 15D:
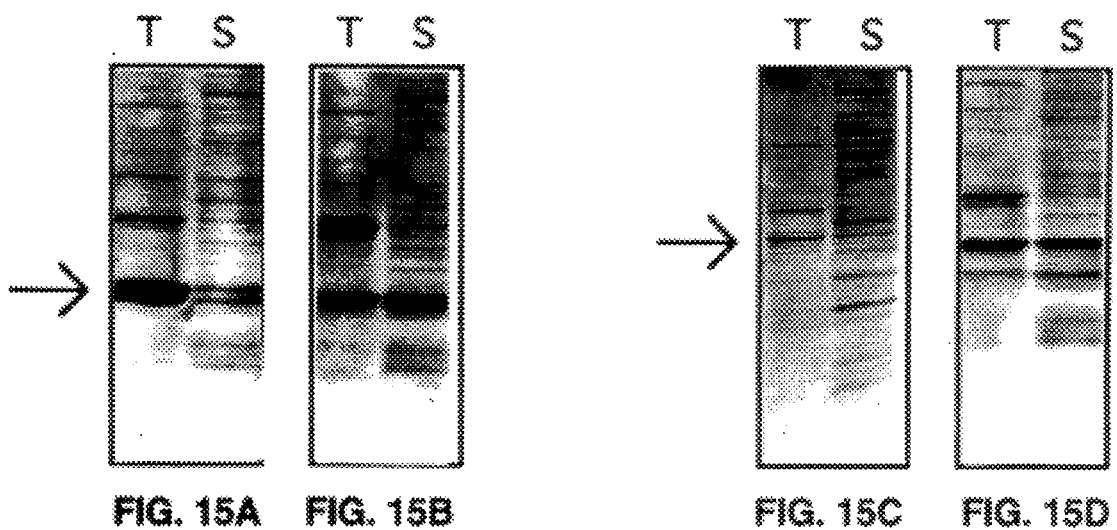
FIG. 15 shows the proteins expressed by plasmids pDM15486, pDM25492, pDM46805 and pDM46806 when they are introduced into W3110DE3. Panels "A" and "B" of FIG. 15 show the TEX extracts (T) and the remaining soluble fraction (S) after sonication of strains carrying pDM25492 and pDM46805 respectively. The corresponding samples for the IGF-I fusion constructs, pDM15486 and pDM46806, are shown in panels "C" and "D" of FIG. 15. The expected position of the DsbC protein is marked by an arrow in each case.

FIG. 15 shows the proteins expressed by these plasmids when they are introduced into W3110DE3. After induction and selective extraction as described in Example 1 above, samples were separated on 4–20% acrylamide gradient gels, stained with Coomassie Blue and photographed. Panels "A" and "B" of FIG. 15 show the TEX extracts (T) and the remaining soluble fraction (S) after sonication of strains carrying pDM25492 and pDM46805 respectively. The corresponding samples for the IGF-I fusion constructs, pDM15486 and pDM46806, are shown in panels "C" and "D" of FIG. 15. The expected position of the DsbC protein is marked by an arrow in each case.

These results clearly indicate that leader-deleted DsbC is efficiently translocated out of the cytoplasm, as are fusions of DsbC to IGF-I. The presence of the double cysteine active site loop is apparently not required for transport.

Example 11: Expression of Mini-DsbA and Fusions

In order to test the effect of removing the entire region surrounding the double cysteine active site loop of DsbA, the DsbA expression vector pYZ9206 (described in Example 1 above) was modified by replacing the DNA between the unique BssHII and BglII sites of this plasmid with synthetic DNA of the sequence: 5' . . . GCGCGCCTTCTGGT-TCTTTCATGGGTGGTGACCTGGGCAAAGATCT . . . 3' (SEQ ID NO: 17). The effect of this replacement (hereinafter referred to as "mini-DsbA") is to substitute the amino acids Ser-Gly-Ser for amino acids #21–62 of the original (mature) DsbA. The double cysteine active site loop, located at #30–33, is deleted by this procedure. The resulting plasmid, pDM25452, was further modified by fusing ubiquitin and IGF sequences to the carboxy-terminal end of the mini-DsbA to produce pDM25486. pDM25499 is a variant of pDM25486 in which the DNA coding for the aminoterminal 45 amino acids of ubiquitin have been further deleted.

The DNA sequences of the leader-deleted mini-DsbAs encoded by pDM25452, pDM25486 and pDM25499 are listed in FIGS. 28, 42 and 41, respectively.

Figures 16A, 16B, 16C:
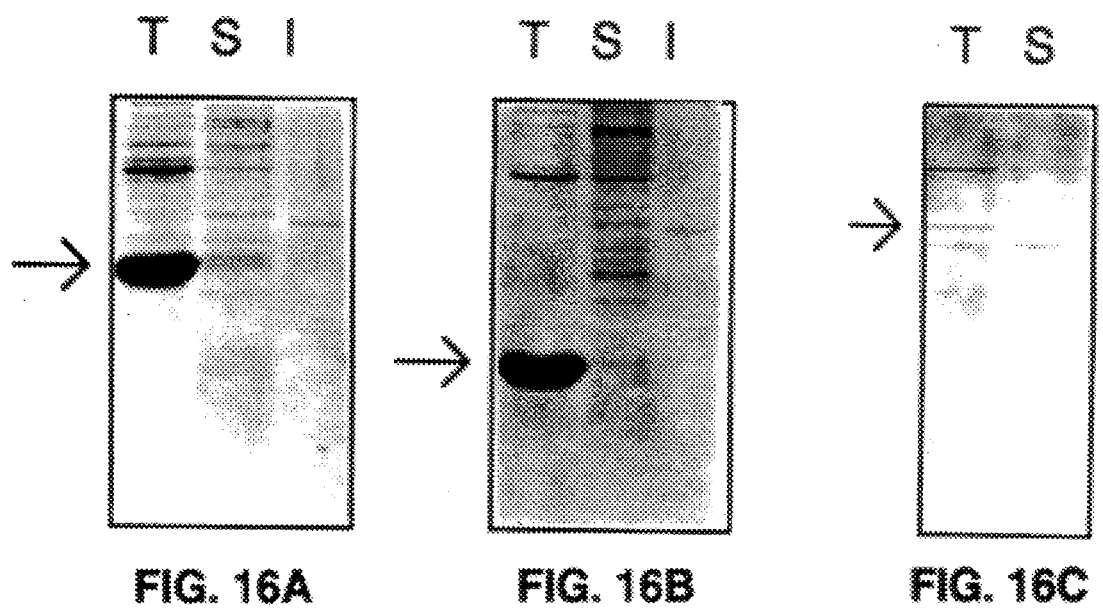
FIG. 16 shows the proteins expressed by plasmids pDM15486, pDM25492, pDM46805 and pDM46806 when they are tested as described for the constructs in Example 10 above. Panels "A" and "B" show a comparison of pYZ9206 (leader-deleted DsbA) and pDM25452 (leader-deleted mini-DsbA). In each case the induced samples have been fractionated into TEX (T), remainder soluble (S), and insoluble (I) fractions. Panel "C" shows the results obtained with pDM25499.

FIG. 16 shows the proteins expressed by these plasmids when they are tested as described for the constructs in Example 10 above. Panels "A" and "B" show a comparison of pYZ9206 (leader-deleted DsbA) and pDM25452 (leader-deleted mini-DsbA). In each case the induced samples have been fractionated into TEX (T), remainder soluble (S), and insoluble (I) fractions. Panel "C" shows the results obtained with pDM25499.

The results show that mini-DsbA is readily translocated out of the cytoplasm and accumulates in soluble form. The presence of the double cysteine active site loop is apparently irrelevant to the transport function of leader-deleted DsbA.

Table 6 below describes the plasmids used in the Examples contained herein.

TABLE 6

| Plasmid | Figure | Seq.ID No. | Description |
|---|---|---|---|
| 25453 | 20 | | Native dsbA with leader) biotinylation peptide |
| 25450 | 21 | | Leaderless dsbA (3' modified)-biotinylation peptide |
| 25477 | 22 | | Leaderless dsbA (3' modified)-hubi (de145).IGF.new |
| 41620 | 23 | | Leaderless dsbA (3' modified)-hubi.IGF.new |
| 9205 | 24 | | Native dsbA |
| 46805 | 25 | | Leaderless dsbC (3' modified)C−>S variant |
| 9206 | 26 | | Leaderless dsbA |
| 22055 | 27 | | Leaderless dsbA (3' modified) |
| 25452 | 28 | | Leaderless mini-dsbA |

TABLE 6-continued

| Plasmid | Figure | Seq.ID No. | Description |
|---|---|---|---|
| | | | (3' modified) |
| 22070 | 29 | | Leaderless dsbA (3' modified)-y.ubi.IGF.old |
| 25498[a] | 30 | | Leaderless dsbC (3' modified)-hubi.IGF.new |
| 46806 | 31 | | Leaderless dsbC (3' modified) C > S variant IGF1 (new) |
| 15486 | 32 | | Leaderless dsbC (3' modified)-IGF1 (new) |
| 25492 | 33 | | Leaderless dsbC (3' modified) |
| 16963[b] | 34 | | Mature human interleukin 1 beta (3' modified-IGF old) |
| 12151[b] | 35 | | Mature human interleukin 1 beta |
| 15449 | 36 | | Mature human interleukin 1 beta (3' modified) |
| 25466 | 37 | | Human interleukin 1 beta R11G mutant (3' modified) |
| 99999 | 38 | | Interleukin-1 receptor antagonist (3' modified)-IGF1 (new) |
| 15424 | 39 | | Leaderless interleukin-1 receptor |
| 16965 | 40 | | Mature human interleukin 1 beta (3' modified)-yubi.IGF.old |
| 25499 | 41 | | Mini-dsbA (3' modified)-hubi (de145).Igf.new |
| 25485[a] | 42 | | Leaderless mini-dsbA (3' modified)-hubi.IGF.new |

[a]in pUC18 vector
[b]in pBR322 vector

Example 12: Expression of in vivo-biotinylated DsbA and IL1-beta

A recent report (Schatz, Bio/Technology 11:1138–1143, 1993) identifies a consensus 13-mer peptide sequence which apparently mimics the target substrate for E. coli biotin holoenzyme synthetase. To investigate the effect of adding this sequence to the carboxy-terminus of DsbA and IL1-beta, the leader-deleted DsbA gene in the vector pYZ22055 (similar to pYZ9206, above, except that the sequence downstream of the carboxy-terminal Lysine codon 189 is synthetic: 5' . . . CATCATCACCATCATCACAGCATGCCCG GGCTCGAGTAAGCTTATGCAT . . . 3'(SEQ ID NO: 18); termination codon underlined) was modified by inserting the synthetic sequence: 5' . . . GCATGGGTTCTCTGAAAC-CTATCTTTGACGCTCAGAAGATTGAGTGGCGTCA TAGCATGCACCGCGGTCTCGAG . . . 3' between the unique SphI and XhoI sites within the carboxyterminal linker of the dsbA sequence in pYZ22055. This manipulation fuses the biotinylation substrate peptide sequence immediately downstream of the leader-deleted DsbA sequence. The resulting plasmid is pDM25450. The control plasmid pDM25453 is identical to pDM25450 except that the native DsbA leader sequence has been restored in pDM25453.

pDM15457 was constructed in a manner analogous to pDM25450 above. It codes for a biotinylation substrate peptide immediately downstream of IL1-beta. pDM15449 is the parent vector expressing unmodified IL1-beta.

The DNA sequences present in pYZ22055, pDM25450, pDM25453 and pDM15449 are listed in FIGS. 27, 21, 20 and 35, respectively.

Figures 17A, 17B:
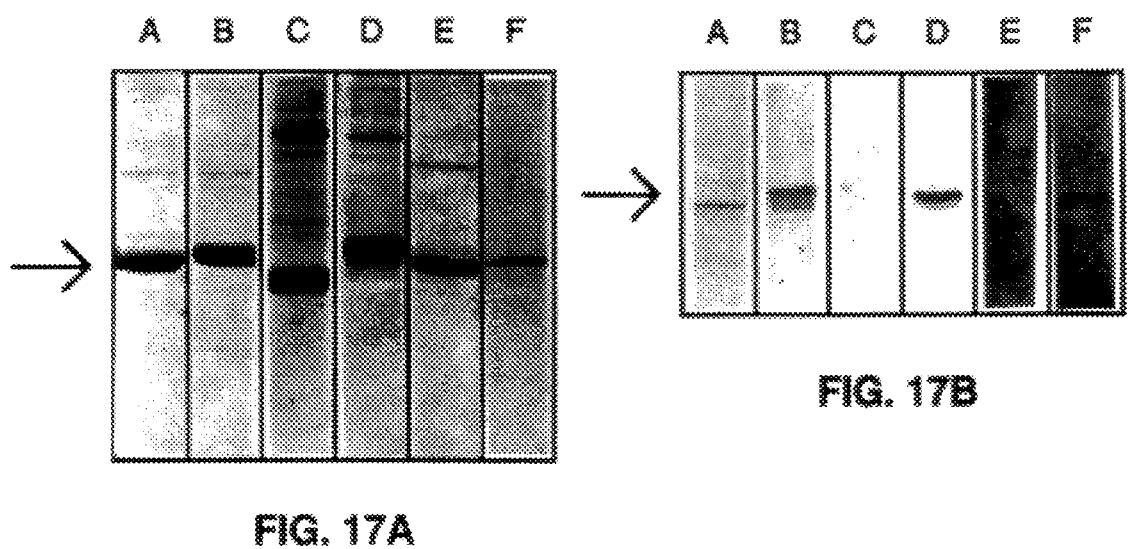
FIG. 17 shows the results obtained when the proteins expressed by plasmids pYZ22055, pDM25450, pDM25453 and pDM15449 are analyzed. Lanes "A", "B", "C" and "D" in each panel were loaded with extracts corresponding to pYZ22055, pDM25450, pDM15449 and pDM15457. The two constructs expressing the 13-mer biotinylation substrate peptide (pDM25450 and pDM15457) provide clear positive signals on the Western blot, whereas the controls do not.
Figures 18A, 18B:
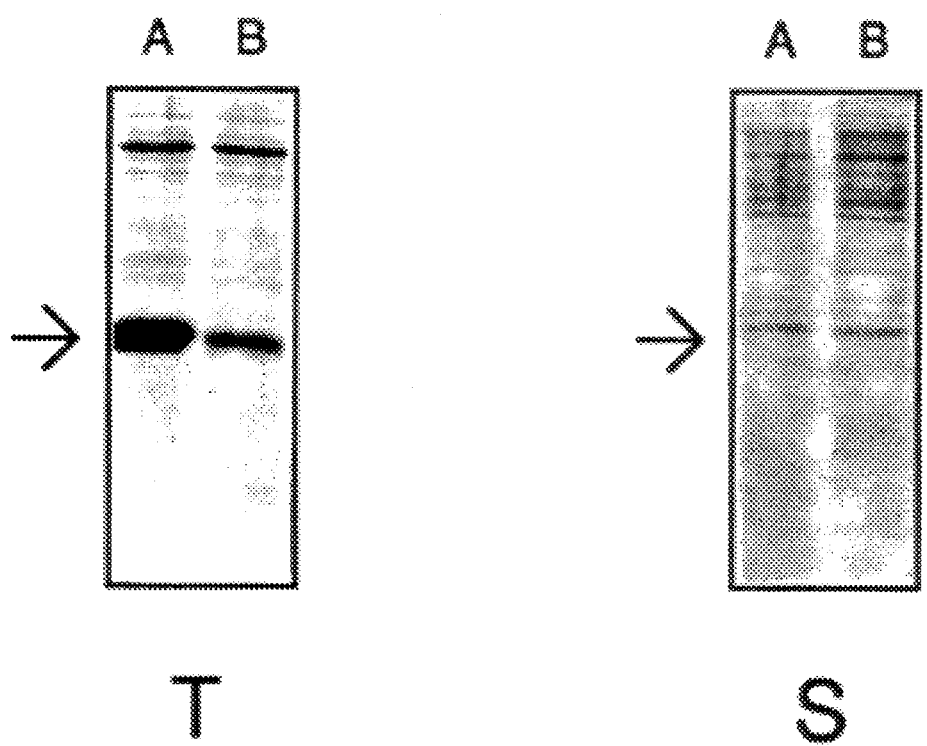
FIG. 18 shows the fractionation of samples taken from induced cells carrying pDM15449 (panels "A") or pDM25466 (panels "B").
Figure 19A:
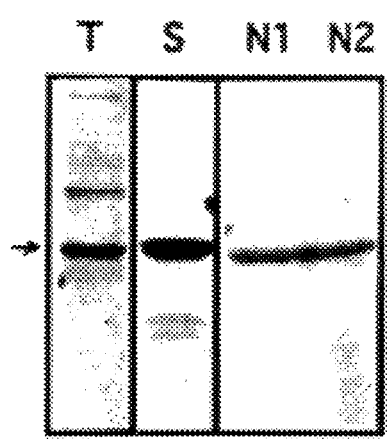
FIG. 19A shows the expression of the fusion protein and its partial fractionation into TEX (T) and remainder soluble (S) fractions.
Figure 19B:
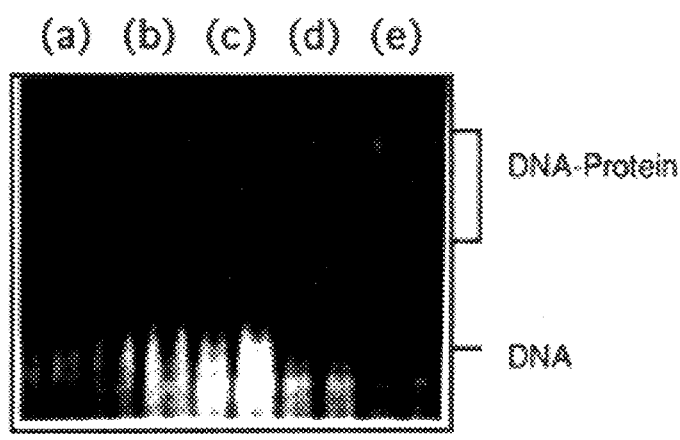
FIG. 19B shows that both purified fractions show DNA-binding activity.

FIG. 17 shows the results obtained when the proteins expressed by these plasmids are analyzed as described in the preceding examples (see Examples 1, 10 & 11 above). Only the TEX fractions were subjected to analysis. Gels were stained with Coomassie Blue and photographed, or Western-blotted and treated with a reagent kit designed to detect biotinylated protein (Clontech's GENE-TECT Cat.#K1035-1; Palo Alto, Calif.).

Lanes "A", "B", "C" and "D" in each panel were loaded with extracts corresponding to pYZ22055, pDM25450, pDM15449 and pDM15457. The two constructs expressing the 13-mer biotinylation substrate peptide (pDM25450 and pDM15457) provide clear positive signals on the Western blot, whereas the controls do not.

To further test this detection system, TEX extracts from pDM25450 and pDM25453 (both coding for the biotinylation substrate13-mer) were subjected to Ni-NTA affinity chromatography (QUIAGEN, Inc. Chatsworth, Calif.) according to the manufacturer's instructions. The modified carboxy-terminus of the DsbA protein encoded by these two plasmids contains a run of six histidine residues which facilitate binding to the Ni-NTA resin. After secretion of the pDM25453 protein (when the leader is cleaved off by leader peptidase) the protein should be identical to the leader-deleted version encoded by pDM25450. Thus the only nominal difference between the two DsbA proteins purified in this experiment is the route by which they have been transported out of the cytoplasm: The pDM25453 product by the general secretory pathway, and the pDM25450 product by (presumably) some novel mechanism. When they are tested (panels "E" and "F" respectively) these purified proteins show at least a ten-fold difference in the efficiency with which they have been biotinylated.

Separate tests show no difference in the specific enzymatic activity (oxidoreductase) of the two proteins, when assayed as described in Example 3. This suggests that both proteins are folded correctly.

Taken together, these data provide strong evidence for an independent mode of extracytoplasmic transport for leader-deleted DsbA protein.

Example 13: Expression and Transport of IL1-beta R11G Mutant

The effect of substitution mutations at several positions within the interleukin-1-beta sequence has been evaluated with respect to biological activity. The R11G (Arg-11 to Gly) mutant shows normal binding to one IL1 receptor but no biological activity. Receptor-binding suggests normal conformational folding of the protein. Thus, it might be reasonable to suppose that the R11G mutant might be unaffected with respect to its transport function in *E. coli.* pDM25466 is analogous to pDM15449 (see example 12 above) except that codon #11 has been changed from CGG (Arg) to GGG (Gly) by site-directed mutagenesis methods well-known to those skilled in the art. The DNA sequence of the IL1 gene in pDM25466 is listed in FIG. 37.

FIG. 18 shows the fractionation of samples taken from induced cells carrying pDM15449 (panels "A") or pDM25466 (panels "B"). Although the level of accumulation of the mutant protein is reduced, transport clearly occurs.

Example 14: Expression of DsbA-yeast MAT alpha-2 Homeodomain

Approximately 60 amino acids of the yeast alpha-2 homeodomain are sufficient to bind DNA (Wolberger et al., *Cell* 67:517–528, 1991). Using the primers 5' . . . GGCGGGCATGCACGGTTCAAGTACTAAACCTTACAGAGGA . . . 3' (SEQ ID NO: 20) and 5' . . . GGGGAATTCATGCATTATATTGTTTTTTCTTTACGACGACGATTCGAAACCC AGTTTTTGA . . . 3' (SEQ ID NO: 21) and *S. cerevisiae* genomic DNA (Sigma Chem. Co., St. Louis, Mo.) as a substrate, a 0.22 kb PCR fragment was generated, cleaved with SphI+NsiI and cloned into pYZ22055 vector (above) cut with the same enzymes. The resulting plasmid, pDM15478, carries an in-frame fusion between the carboxy-terminal end of DsbA and the amino-terminal end of the alpha-2 homeodomain. Strains carrying this plasmid were tested as described in the preceding examples.

FIG. 19A shows the expression of the fusion protein and its partial fractionation into TEX (T) and remainder soluble (S) fractions. Using the Ni-NTA method described in Example 12, purified fusion protein was prepared from (T) and (S) fractions. These purified fractions are shown in panels N1 and N2 of FIG. 19A.

FIG. 19B shows that both purified fractions show DNA-binding activity. The oligonucleotides are exactly as described in Wolberger et al (ibid.) and the control panels are (a) no protein (b) DsbA standard (purchased from Epicentre Technologies, Madison, Wis.) and (c) biotinylated DsbA; see example 12, above. (d) and (e) are the purified fusion protein samples N1 and N2. All samples are loaded in duplicate on a TBE acrylamide gradient gel (4–20%). After electrophoresis, the gel is stained with ethidium bromide (1 microgram per milliliter) and photographed.

The results clearly show DNA binding activity from the fusion protein samples, but not in the controls.

All publications and patent applications mentioned in this specification are incorporated herein by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

We claim:

1. A nucleic acid encoding a fusion polypeptide, said fusion polypeptide comprising:
   a) a fusion partner capable of directing extracytoplasmic transport, comprising at least one fragment of a mature polypeptide, wherein the mature polypeptide is selected from the group consisting of a mutant mature DsbA lacking a double cysteine active site loop domain, mature DsbC and a mutant mature DsbC lacking a double cysteine active site loop domain, said fusion partner lacking a signal sequence and comprising a carboxy terminus; and
   b) a polypeptide of interest, wherein said polypeptide of interest is positioned distal to the carboxy terminus of said fusion partner.

2. The nucleic acid of claim 1, wherein the fusion polypeptide further comprises a linker peptide positioned between said fusion partner and said polypeptide of interest.

3. The nucleic acid of claim 2, wherein said linker peptide comprises a polypeptide cleavage site.

4. The nucleic acid of claim 3, wherein said cleavage site is a ubiquitin molecule.

5. The nucleic acid of claim 1, wherein said polypeptide of interest is a heterologous polypeptide.

6. An expression vector comprising the nucleic acid of claim 1.

7. A host cell comprising the nucleic acid of claim 1.

8. A nucleic acid encoding a fusion polypeptide, said fusion polypeptide comprising:
   a) a fusion partner comprising a polypeptide selected from the group consisting of mature DsbC, a mutant polypeptide variant of mature DsbC lacking a double cysteine active site loop domain and a mutant polypeptide variant of mature DsbA lacking a double cysteine active site loop domain, said fusion partner lacking a signal sequence;
   b) a linker peptide comprising a ubiquitin molecule; and
   c) a polypeptide of interest, wherein said polypeptide of interest is positioned distal to the carboxy terminus of said fusion partner, and further wherein said linker peptide is positioned between said fusion partner and said polypeptide of interest.

9. A host cell comprising:
   a) an expression vector capable of expressing in said host cell a fusion polypeptide, said fusion polypeptide comprising, i) a fusion partner comprising a polypeptide selected from the group consisting of mature DsbC, a mutant polypeptide variant of mature *E. coli* DsbC lacking a double cysteine active site loop domain and a mutant polypeptide variant of mature DsbA lacking a double cysteine active site loop domain, said fusion partner lacking a signal sequence and comprising a carboxy terminus, ii) a linker peptide comprising a cleavage site, and iii) a polypeptide of interest, wherein said polypeptide of interest is positioned distal to the carboxy terminus of said fusion partner, and further wherein said linker peptide is positioned between said fusion partner and said polypeptide of interest; and b) a nucleic acid capable of expressing in said host cell a proteolytic enzyme which specifically recognizes said cleavage site.

10. The host cell of claim 9, wherein said proteolytic enzyme is ubiquitin hydrolase and said cleavage site is a ubiquitin molecule.

11. A fusion polypeptide comprising:

a) a fusion partner capable of directing extracytoplasmic transport, comprising at least one fragment of a polypeptide, wherein the polypeptide is selected from the group consisting of DsbC, a mutant DsbC lacking a double cysteine active site loop domain and a mutant mature DsbA lacking a double cysteine active site loop domain, said fusion partner lacking a signal sequence and comprising a carboxy terminus; and b) a polypeptide of interest, wherein said polypeptide of interest is positioned distal to the carboxy terminus of said fusion partner.

12. The fusion polypeptide of claim 11, further comprising a linker peptide positioned between said fusion partner and said polypeptide of interest.

13. The fusion polypeptide of claim 12, wherein said linker peptide comprises a cleavage site.

14. The fusion polypeptide of claim 13, wherein said cleavage site is a ubiquitin molecule.

15. The fusion polypeptide of claim 11 wherein said polypeptide of interest comprises a protein selected from the group consisting of an enzyme, a growth factor, an antibody polypeptide, a DNA-binding protein, an RNA binding protein, and a membrane receptor.

16. The fusion polypeptide of claim 11 wherein said polypeptide of interest is a heterologous polypeptide.

17. A fusion polypeptide comprising:

a) a fusion partner comprising a polypeptide selected from the group consisting of DsbC, mature DsbC, a mutant polypeptide variant of DsbC lacking a double cysteine active site loop domain and a mutant polypeptide variant of mature DsbA lacking a double cysteine active site loop domain, said fusion partner lacking a signal sequence and comprising a carboxy terminus;

b) a linker peptide comprising a ubiquitin molecule; and c) a polypeptide of interest, wherein said polypeptide of interest is positioned distal to the carboxy terminus of said fusion partner, and further wherein said linker peptide is positioned between said fusion partner and said polypeptide of interest.

18. A method of producing a substantially purified fusion polypeptide encoded by a nucleic acid, wherein said fusion polypeptide comprises, a fusion partner capable of directing extracytoplasmic transport, comprising at least one fragment of a mature polypeptide, wherein the mature polypeptide is selected from the group consisting of DsbC, a mutant DsbC lacking a double cysteine active site loop domain, and a mutant DsbA lacking a double cysteine active site loop domain, said fusion partner lacking a signal sequence and comprising a carboxy terminus, and a polypeptide of interest, wherein said polypeptide of interest is positioned distal to the carboxy terminus of said fusion partner; said method comprising the steps of:

a) introducing said nucleic acid encoding said fusion polypeptide into a host cell, thereby producing a transformed host cell;

b) culturing said transformed host cell under conditions appropriate for expressing said fusion polypeptide; and c) purifying said fusion polypeptide, thereby obtaining a substantially purified fusion polypeptide.

19. A method of producing a substantially purified polypeptide of interest, said method comprising the steps of:

a) introducing into a host cell a nucleic acid encoding a fusion polypeptide, said fusion polypeptide comprising:

i) a fusion partner capable of directing extracytoplasmic transport, comprising at least one fragment of a mature polypeptide, wherein the mature polypeptide is selected from the group consisting of DsbC, a mutant DsbC lacking a double cysteine active site loop domain, and a mutant DsbA lacking a double Cysteine active site loop domain, said fusion partner lacking a signal sequence and comprising a carboxy terminus, ii) a polypeptide of interest, wherein said polypeptide of interest is positioned distal to the carboxy terminus of said fusion partner, and iii) a linker peptide encoding a cleavage site, wherein said linker peptide is positioned between said fusion partner and said polypeptide of interest; thereby producing a transformed host cell;

b) culturing said transformed host cell under conditions appropriate for expressing said fusion polypeptide, thereby expressing said fusion polypeptide;

c) cleaving said fusion polypeptide with a proteolytic enzyme or cleavage agent which recognizes said proteolytic cleavage site, thereby producing said polypeptide of interest; and d) purifying said polypeptide of interest, thereby obtaining a substantially purified polypeptide of interest.

20. The method of claim 19, wherein said proteolytic enzyme is ubiquitin hydrolase and said cleavage site is a ubiquitin molecule.

21. A method of producing a substantially purified polypeptide of interest, said method comprising the steps of:

a) introducing into a host cell a nucleic acid encoding a fusion polypeptide, said fusion polypeptide comprising, i) a fusion partner capable of directing extracytoplasmic transport, comprising at least one fragment of a mature polypeptide, wherein the mature polypeptide is selected from the group consisting of DsbC, a mutant DsbC lacking a double cysteine active site loop domain, and a mutant DsbA lacking a double cysteine active site loop domain, said fusion partner lacking a signal sequence and comprising a carboxy terminus, ii) a polypeptide of interest, wherein said polypeptide of interest is positioned distal to the carboxy terminus of said fusion partner, and iii) a linker peptide encoding a cleavage site, wherein said linker peptide is positioned between said fusion partner and said polypeptide of interest; thereby producing a transformed host cell;

b) culturing said transformed host cell under conditions appropriate for expressing said fusion polypeptide, thereby expressing said fusion polypeptide;

c) purifying said fusion polypeptide, thereby producing a substantially purified fusion polypeptide;

d) cleaving said substantially purified fusion polypeptide with a proteolytic enzyme or cleavage agent which recognizes said proteolytic cleavage site, thereby producing said polypeptide of interest; and e) purifying said polypeptide of interest, thereby obtaining a substantially purified polypeptide of interest.

22. A method of producing a substantially purified polypeptide of interest comprising the steps of:

a) introducing into a host cell a nucleic acid encoding a fusion polypeptide, said fusion polypeptide comprising, i) a fusion partner capable of directing extracytoplasmic transport, comprising at least one fragment of a mature polypeptide, wherein the mature polypeptide is selected from the group consisting of DsbC, a mutant DsbC lacking a double cysteine active site loop domain, and a mutant DsbA lacking a double cysteine active site loop domain, said fusion partner lacking a signal sequence and comprising a carboxy terminus, ii) a polypeptide of interest, wherein said polypeptide of interest is positioned distal to the carboxy terminus of said fusion partner, and iii) a linker peptide encoding a cleavage site, wherein said linker peptide is positioned between said fusion partner and said polypeptide of interest;

and further wherein said host cell comprises a nucleic acid capable of expressing in said host cell a proteolytic enzyme which specifically recognizes said cleavage site, thereby producing a transformed host cell;

b) culturing said transformed host cell under conditions appropriate for expressing said fusion polypeptide and said proteolytic enzyme, thereby expressing said fusion polypeptide, causing the in vivo cleavage of said fusion polypeptide, and producing said polypeptide of interest; and c) purifying said polypeptide of interest, thereby obtaining a substantially purified polypeptide of interest.

23. The method of claim 22, wherein said proteolytic enzyme is ubiquitin hydrolase and said cleavage site is a ubiquitin molecule.

* * * * *